(12) United States Patent
Unger et al.

(10) Patent No.: US 7,105,151 B2
(45) Date of Patent: *Sep. 12, 2006

(54) OXYGEN DELIVERY AGENTS AND USES FOR THE SAME

(75) Inventors: Evan C. Unger, Tucson, AZ (US);
Thomas McCreery, Tucson, AZ (US);
Yunqiu Wu, Tucson, AZ (US)

(73) Assignee: ImaRx Therapeutics, Inc., Tucson, AZ (US)

(*) Notice: Subject to any disclaimer, the term of this patent is extended or adjusted under 35 U.S.C. 154(b) by 336 days.

This patent is subject to a terminal disclaimer.

(21) Appl. No.: 10/336,906

(22) Filed: Jan. 6, 2003

(65) Prior Publication Data

US 2003/0120204 A1    Jun. 26, 2003

Related U.S. Application Data

(62) Division of application No. 08/877,826, filed on Jun. 18, 1997, now Pat. No. 6,537,246.

(51) Int. Cl.
*A61B 8/00* (2006.01)

(52) U.S. Cl. .................. 424/9.52; 424/9.51; 424/450; 424/489

(58) Field of Classification Search ............... 424/9.52, 424/9.51, 450, 489
See application file for complete search history.

(56) References Cited

U.S. PATENT DOCUMENTS

| | | | |
|---|---|---|---|
| 3,015,128 A | 1/1962 | Sommerville et al. | 18/2.6 |
| 3,291,843 A | 12/1966 | Fritz et al. | 260/614 |
| 3,293,114 A | 12/1966 | Kenaga et al. | 162/168 |
| 3,401,475 A | 9/1968 | Morehouse et al. | 40/306 |
| 3,479,811 A | 11/1969 | Walters | 57/153 |
| 3,488,714 A | 1/1970 | Walters et al. | 161/161 |
| 3,532,500 A | 10/1970 | Priest et al. | 96/91 |
| 3,557,294 A | 1/1971 | Dear et al. | 424/342 |
| 3,594,326 A | 7/1971 | Himmel et al. | 252/316 |
| 3,615,972 A | 10/1971 | Morehouse et al. | 156/79 |
| 3,650,831 A | 3/1972 | Jungermann et al. | |
| 3,732,172 A | 5/1973 | Herbig et al. | 252/316 |
| 3,873,564 A | 3/1975 | Schneider et al. | 270/309.6 |
| 3,945,956 A | 3/1976 | Garner | 270/2.5 B |
| 3,960,583 A | 6/1976 | Netting et al. | 106/122 |
| 3,968,203 A | 7/1976 | Spitzer et al. | 424/47 |
| 4,027,007 A | 5/1977 | Messina | 424/46 |
| 4,044,757 A | 8/1977 | McWhorter et al. | 128/2 A |
| 4,089,801 A | 5/1978 | Schneider | 252/316 |
| 4,108,806 A | 8/1978 | Cohrs et al. | 521/54 |
| 4,138,383 A | 2/1979 | Rembaum et al. | 270/29.7 H |
| 4,162,282 A | 7/1979 | Fulwyler et al. | 274/9 |
| 4,179,546 A | 12/1979 | Garner et al. | 521/56 |
| 4,192,859 A | 3/1980 | Mackaness et al. | 424/5 |
| 4,224,179 A | 9/1980 | Schneider | 252/316 |
| 4,229,360 A | 10/1980 | Schneider et al. | 270/403 |
| 4,229,360 A | 10/1980 | Schneider et al. | 270/403 |
| 4,265,251 A | 5/1981 | Tickner | 128/660 |
| 4,276,885 A | 7/1981 | Tickner et al. | 128/660 |
| 4,303,736 A | 12/1981 | Torobin | 428/403 |
| 4,310,505 A | 1/1982 | Baldeschwieler et al. | 424/1 |
| 4,310,506 A | 1/1982 | Baldeschwieler et al. | 424/1 |
| 4,315,514 A | 2/1982 | Drewes et al. | 128/653 |
| 4,331,654 A | 5/1982 | Morris | 424/38 |
| 4,342,826 A | 8/1982 | Cole | 435/7 |
| 4,344,929 A | 8/1982 | Bonsen et al. | 424/15 |
| 4,420,442 A | 12/1983 | Sands | 274/13 |
| 4,421,562 A | 12/1983 | Sands et al. | 106/75 |
| 4,426,330 A | 1/1984 | Sears | 270/403 |
| 4,427,649 A | 1/1984 | Dingle et al. | 424/38 |
| 4,428,924 A | 1/1984 | Millington | 424/4 |
| 4,442,843 A | 4/1984 | Rasor et al. | 128/660 |
| 4,466,442 A | 8/1984 | Hilmann et al. | 128/653 |
| 4,485,193 A | 11/1984 | Rubens et al. | 521/58 |
| 4,512,764 A | 4/1985 | Wunsch | 604/80 |
| 4,530,360 A | 7/1985 | Duarte | 128/419 F |
| 4,533,254 A | 8/1985 | Cook et al. | 366/176 |
| 4,534,899 A | 8/1985 | Sears | 270/403 |
| 4,540,629 A | 9/1985 | Sands et al. | 428/402 |
| 4,544,545 A | 10/1985 | Ryan et al. | 424/1.1 |
| 4,549,892 A | 10/1985 | Baker et al. | 65/21.4 |
| 4,569,836 A | 2/1986 | Gordon | 424/1.1 |
| 4,572,203 A | 2/1986 | Feinstein | 128/661 |
| 4,582,756 A | 4/1986 | Niinuma et al. | 428/327 |
| 4,586,512 A | 5/1986 | Do-huu et al. | 128/660 |
| 4,603,044 A | 7/1986 | Geho et al. | 424/9 |
| 4,615,879 A | 10/1986 | Runge et al. | 424/9 |

(Continued)

FOREIGN PATENT DOCUMENTS

AU                641363          3/1990

(Continued)

OTHER PUBLICATIONS

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568-574 (1974).

(Continued)

*Primary Examiner*—Dameron L. Jones
(74) *Attorney, Agent, or Firm*—DLA Piper Rudnick Gray Cary US LLP

(57) ABSTRACT

The present invention describes, inter alia, oxygen delivery agents or blood substitutes comprising a fluorinated gas and a stabilizing material, uses for the oxygen delivery agents or blood substitutes, and apparatus for making and delivering the oxygen delivery agents or blood substitutes.

38 Claims, 9 Drawing Sheets

U.S. PATENT DOCUMENTS

| | | | |
|---|---|---|---|
| 4,620,546 A | 11/1986 | Aida et al. | 128/660 |
| 4,621,023 A | 11/1986 | Redziniak et al. | 428/402.2 |
| 4,625,494 A | 12/1986 | Iwatschenko et al. | 53/432 |
| 4,646,756 A | 3/1987 | Watmough et al. | 128/804 |
| 4,657,756 A | 4/1987 | Rasor et al. | 424/9 |
| 4,658,828 A | 4/1987 | Dory | 128/660 |
| 4,663,161 A | 5/1987 | Mannino et al. | 424/89 |
| 4,675,310 A | 6/1987 | Chapman et al. | 514/6 |
| 4,681,119 A | 7/1987 | Rasor et al. | 128/660 |
| 4,684,479 A | 8/1987 | D'Arrigo | 252/307 |
| 4,689,986 A | 9/1987 | Carson et al. | 73/19 |
| 4,693,999 A | 9/1987 | Axelsson et al. | 514/174 |
| 4,718,433 A | 1/1988 | Feinstein | 128/660 |
| 4,728,575 A | 3/1988 | Gamble et al. | 428/402.2 |
| 4,728,578 A | 3/1988 | Higgins et al. | 428/462 |
| 4,731,239 A | 3/1988 | Gordon | 424/9 |
| 4,737,323 A | 4/1988 | Martin et al. | 274/4.3 |
| 4,774,958 A | 10/1988 | Feinstein | 128/660.01 |
| 4,775,522 A | 10/1988 | Clark, Jr. | 424/9 |
| 4,776,991 A | 10/1988 | Farmer et al. | 274/4.3 |
| 4,781,871 A | 11/1988 | West, III et al. | 274/4.3 |
| 4,789,501 A | 12/1988 | Day et al. | 252/645 |
| 4,790,891 A | 12/1988 | Halliday et al. | 149/2 |
| 4,822,534 A | 4/1989 | Lencki et al. | 274/4.3 |
| 4,830,858 A | 5/1989 | Payne et al. | 424/450 |
| 4,834,964 A | 5/1989 | Rosen | 424/9 |
| 4,844,882 A | 7/1989 | Widder et al. | 424/9 |
| 4,863,717 A | 9/1989 | Keana | 424/9 |
| 4,865,836 A | 9/1989 | Long, Jr. | 424/5 |
| 4,877,561 A | 10/1989 | Iga et al. | 274/4.3 |
| 4,893,624 A | 1/1990 | Lele | 128/399 |
| 4,895,719 A | 1/1990 | Radhakrishnan | 424/45 |
| 4,898,734 A | 2/1990 | Mathiowitz et al. | 424/427 |
| 4,900,540 A | 2/1990 | Ryan et al. | 424/9 |
| 4,918,065 A | 4/1990 | Stindl et al. | 514/179 |
| 4,919,895 A | 4/1990 | Heldebrant et al. | 422/129 |
| 4,921,706 A | 5/1990 | Roberts et al. | 424/450 |
| 4,927,623 A | 5/1990 | Long, Jr. | 424/5 |
| 4,933,121 A | 6/1990 | Law et al. | 264/4.3 |
| 4,938,947 A | 7/1990 | Nicolau et al. | 424/1.1 |
| 4,957,656 A | 9/1990 | Cerny et al. | 252/311 |
| 4,972,002 A | 11/1990 | Volkert | 521/120 |
| 4,981,692 A | 1/1991 | Popescu et al. | 424/422 |
| 4,984,573 A | 1/1991 | Leunbach | 128/6.53 |
| 4,985,550 A | 1/1991 | Charpiot et al. | 536/18.4 |
| 4,987,154 A | 1/1991 | Long, Jr. | 514/772 |
| 4,993,415 A | 2/1991 | Long | 128/653 A |
| 4,996,041 A | 2/1991 | Arai et al. | 424/9 |
| 5,000,960 A | 3/1991 | Wallach | 424/450 |
| 5,004,611 A | 4/1991 | Leigh | 424/450 |
| 5,008,050 A | 4/1991 | Cullis et al. | 274/4.3 |
| 5,008,109 A | 4/1991 | Tin | 424/422 |
| 5,013,556 A | 5/1991 | Woodle et al. | 424/450 |
| 5,019,370 A | 5/1991 | Jay et al. | 424/4 |
| 5,045,304 A | 9/1991 | Schneider et al. | 424/9 |
| 5,049,388 A | 9/1991 | Knight et al. | 424/450 |
| 5,078,994 A | 1/1992 | Nair et al. | 424/501 |
| 5,088,499 A | 2/1992 | Unger | 128/662.2 |
| 5,107,842 A | 4/1992 | Levene et al. | 128/662.02 |
| 5,114,703 A | 5/1992 | Wolf et al. | 424/5 |
| 5,123,414 A | 6/1992 | Unger | 128/654 |
| 5,135,000 A | 8/1992 | Akselrod et al. | 128/662.02 |
| 5,137,928 A | 8/1992 | Erbel et al. | 521/56 |
| 5,141,738 A | 8/1992 | Rasor et al. | 424/2 |
| 5,147,631 A | 9/1992 | Glajch et al. | 424/9 |
| 5,149,319 A | 9/1992 | Unger | 604/22 |
| 5,171,755 A | 12/1992 | Kaufman | 514/759 |
| 5,186,922 A | 2/1993 | Shell et al. | 128/654 |
| 5,190,766 A | 3/1993 | Ishihara | 424/489 |
| 5,190,982 A | 3/1993 | Erbel et al. | 521/56 |
| 5,192,549 A | 3/1993 | Barenolz et al. | 424/450 |
| 5,194,188 A | 3/1993 | Guitierrez | 264/4.1 |
| 5,194,266 A | 3/1993 | Abra et al. | 424/450 |
| 5,195,520 A | 3/1993 | Schlief et al. | 128/660.02 |
| 5,196,183 A | 3/1993 | Yudelson et al. | 424/9 |
| 5,196,348 A | 3/1993 | Schweighardt et al. | 436/173 |
| 5,198,225 A | 3/1993 | Meybeck et al. | 424/450 |
| 5,205,287 A | 4/1993 | Erbel et al. | 128/632 |
| 5,205,290 A | 4/1993 | Unger | 128/653.4 |
| 5,209,720 A | 5/1993 | Unger | 604/22 |
| 5,213,804 A | 5/1993 | Martin et al. | 424/450 |
| 5,215,680 A | 6/1993 | D'Arrigo | 252/307 |
| 5,219,538 A | 6/1993 | Henderson et al. | 428/402.2 |
| 5,228,446 A | 7/1993 | Unger et al. | 128/662.02 |
| 5,230,882 A | 7/1993 | Unger | 424/9 |
| 5,234,680 A | 8/1993 | Rogers, Jr. et al. | 424/9 |
| 5,247,935 A | 9/1993 | Cline et al. | 128/653.2 |
| 5,271,928 A | 12/1993 | Schneider et al. | 424/9 |
| 5,276,146 A | 1/1994 | Breillatt, Jr. et al. | 530/513 |
| 5,281,408 A | 1/1994 | Unger | 424/4 |
| 5,283,255 A | 2/1994 | Levy et al. | 514/410 |
| 5,305,757 A | 4/1994 | Unger et al. | 128/662.02 |
| 5,310,540 A | 5/1994 | Giddey et al. | 424/9 |
| 5,312,617 A | 5/1994 | Unger et al. | 424/9 |
| 5,315,997 A | 5/1994 | Widder et al. | 128/653.3 |
| 5,315,998 A | 5/1994 | Tachibana et al. | 128/660.01 |
| 5,316,771 A | 5/1994 | Barenholz et al. | 424/450 |
| 5,334,381 A | 8/1994 | Unger | 424/9 |
| 5,339,814 A | 8/1994 | Lasker | 128/653.4 |
| 5,344,930 A | 9/1994 | Riess et al. | 544/84 |
| 5,350,571 A | 9/1994 | Kaufman et al. | 424/9 |
| 5,352,435 A | 10/1994 | Unger | 424/9 |
| 5,354,549 A | 10/1994 | Klaveness et al. | 424/3 |
| 5,358,702 A | 10/1994 | Unger | 424/9 |
| 5,362,477 A | 11/1994 | Moore et al. | 424/9 |
| 5,362,478 A | 11/1994 | Desai et al. | 424/9 |
| 5,380,411 A | 1/1995 | Schlief | 204/157.15 |
| 5,380,519 A | 1/1995 | Schneider et al. | 424/9 |
| 5,393,524 A | 2/1995 | Quay | 424/9 |
| 5,409,688 A | 4/1995 | Quay | 424/9 |
| 5,410,516 A | 4/1995 | Uhlendorf et al. | 367/7 |
| 5,413,774 A | 5/1995 | Schneider et al. | 424/9.51 |
| 5,425,366 A | 6/1995 | Reinhardt et al. | 128/662.02 |
| 5,433,204 A | 7/1995 | Olson | 128/661.08 |
| 5,445,813 A | 8/1995 | Schneider et al. | 424/9.51 |
| 5,456,900 A | 10/1995 | Unger | 424/9.4 |
| 5,460,800 A | 10/1995 | Walters | 429/9.6 |
| 5,469,854 A | 11/1995 | Unger et al. | 128/662.02 |
| 5,470,582 A | 11/1995 | Supersaxo et al. | 424/489 |
| 5,485,839 A | 1/1996 | Aida et al. | 128/653.1 |
| 5,487,390 A | 1/1996 | Cohen et al. | 128/662.02 |
| 5,496,535 A | 3/1996 | Kirkland | 424/9.37 |
| 5,498,421 A | 3/1996 | Grinstaff et al. | 424/450 |
| 5,501,863 A | 3/1996 | Rössling et al. | 424/489 |
| 5,502,094 A | 3/1996 | Moore et al. | 524/145 |
| 5,505,932 A | 4/1996 | Grinstaff et al. | 424/9.3 |
| 5,508,021 A | 4/1996 | Grinstaff et al. | 424/9.322 |
| 5,512,268 A | 4/1996 | Grinstaff et al. | 424/9.322 |
| 5,527,521 A | 6/1996 | Unger | 424/93 |
| 5,529,766 A | 6/1996 | Klaveness et al. | 424/9.52 |
| 5,531,980 A | 7/1996 | Schneider et al. | 424/9.52 |
| 5,536,489 A | 7/1996 | Lohrmann et al. | 424/9.52 |
| 5,536,490 A | 7/1996 | Klaveness et al. | 424/9.52 |
| 5,539,814 A | 7/1996 | Shoji | 379/215 |
| 5,540,909 A | 7/1996 | Schutt | 424/9.52 |
| 5,542,935 A | 8/1996 | Unger et al. | 604/190 |
| 5,545,396 A | 8/1996 | Albert et al. | 424/93 |
| 5,547,656 A | 8/1996 | Unger | 424/9.4 |
| 5,552,133 A | 9/1996 | Lambert et al. | 424/9.52 |
| 5,552,155 A | 9/1996 | Bailey et al. | 424/450 |
| 5,556,372 A | 9/1996 | Talish et al. | 601/2 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |

| | | | | | | |
|---|---|---|---|---|---|---|
| 5,558,853 A | 9/1996 | Quay ........................ 424/9.5 | DE | 38 03 972 A1 | 8/1989 |
| 5,558,854 A | 9/1996 | Quay ........................ 424/9.52 | EP | 0 052 575 | 5/1982 |
| 5,558,855 A | 9/1996 | Quay ........................ 424/9.5 | EP | 0 107 559 | 5/1984 |
| 5,558,856 A | 9/1996 | Klaveness et al. ......... 424/9.37 | EP | 0 077 752 B1 | 3/1986 |
| 5,560,364 A | 10/1996 | Porter .................. 128/662.02 | EP | 0 224 934 A2 | 6/1987 |
| 5,562,608 A | 10/1996 | Sekins et al. ................. 604/20 | EP | 0 231 091 | 8/1987 |
| 5,562,893 A | 10/1996 | Lohrmann ................. 424/9.52 | EP | 0 243 947 | 11/1987 |
| 5,565,215 A | 10/1996 | Gref et al. .................. 424/501 | EP | 0 272 091 | 6/1988 |
| 5,567,413 A | 10/1996 | Klaveness et al. ......... 424/9.51 | EP | 0 274 431 | 7/1988 |
| 5,567,414 A | 10/1996 | Schneider et al. ......... 424/9.52 | EP | 0 324 938 | 1/1989 |
| 5,567,415 A | 10/1996 | Porter ....................... 424/9.52 | EP | 0 320 433 A2 | 6/1989 |
| 5,567,765 A | 10/1996 | Moore et al. ................ 524/801 | EP | 0 338 971 | 10/1989 |
| 5,569,448 A | 10/1996 | Wong et al. ............... 424/9.45 | EP | 0 359 246 A2 | 3/1990 |
| 5,569,449 A | 10/1996 | Klaveness et al. ......... 424/9.51 | EP | 357163 A1 | 3/1990 |
| 5,571,797 A | 11/1996 | Ohno et al. ................... 514/44 | EP | 0 361 894 | 4/1990 |
| 5,573,751 A | 11/1996 | Quay ........................ 424/9.52 | EP | 0 216 730 | 1/1991 |
| 5,578,292 A | 11/1996 | Schneider et al. ......... 424/9.51 | EP | 441468 A2 | 8/1991 |
| 5,580,575 A | 12/1996 | Gamble et al. .......... 428/402.2 | EP | 0 357 164 B1 | 10/1991 |
| 5,585,112 A | 12/1996 | Unger et al. ................. 424/450 | EP | 0 458 745 A1 | 11/1991 |
| 5,593,680 A | 1/1997 | Bara et al. .................. 424/401 | EP | 0 467 031 A2 | 1/1992 |
| 5,595,723 A | 1/1997 | Quay ........................ 424/9.5 | EP | 0 314 764 B1 | 9/1992 |
| 5,605,673 A | 2/1997 | Schutt et al. ............... 424/9.51 | EP | 0 554 213 A1 | 8/1993 |
| 5,606,973 A | 3/1997 | Lambert et al. ....... 128/662.02 | EP | 0 586 875 | 3/1994 |
| 5,612,057 A | 3/1997 | Lanza et al. ................. 424/450 | EP | 0 614 656 A1 | 9/1994 |
| 5,612,318 A | 3/1997 | Weichselbaum et al. ...... 514/44 | EP | 0 633 030 A1 | 1/1995 |
| 5,614,169 A | 3/1997 | Klaveness et al. ......... 424/9.52 | EP | 0 727 225 A2 | 8/1996 |
| 5,620,689 A | 4/1997 | Allen et al. ............... 424/178.1 | EP | 0 901 793 A1 | 3/1999 |
| 5,626,833 A | 5/1997 | Schutt et al. ............... 424/9.52 | FR | 2 700 952 | 8/1994 |
| 5,639,443 A | 6/1997 | Schutt et al. ............... 424/9.52 | GB | 1044680 | 10/1966 |
| 5,639,473 A | 6/1997 | Grinstaff et al. ............. 424/450 | GB | 2193095 A | 2/1988 |
| 5,643,553 A | 7/1997 | Schneider et al. ......... 424/9.52 | JP | 62 286534 | 12/1987 |
| 5,648,095 A | 7/1997 | Illum et al. .................. 424/489 | JP | SHO 63-60943 | 3/1988 |
| 5,648,098 A | 7/1997 | Porter ........................ 424/490 | WO | WO 80/02365 | 11/1980 |
| 5,672,585 A | 9/1997 | Pierschbacher et al. ....... 514/11 | WO | WO 82/01642 | 5/1982 |
| 5,676,928 A | 10/1997 | Klaveness et al. ......... 424/9.32 | WO | WO 84/02909 | 8/1984 |
| 5,679,459 A | 10/1997 | Riess et al. .............. 428/402.2 | WO | WO 85/01161 | 3/1985 |
| 5,686,060 A | 11/1997 | Schneider et al. ......... 424/9.52 | WO | WO 85/02772 | 7/1985 |
| 5,686,102 A | 11/1997 | Gross et al. .................. 424/450 | WO | WO 86/01103 | 2/1986 |
| 5,695,460 A | 12/1997 | Siegel et al. ................. 604/21 | WO | WO 89/05040 | 6/1989 |
| 5,701,899 A | 12/1997 | Porter .................. 428/662.02 | WO | WO 90/01952 | 3/1990 |
| 5,707,352 A | 1/1998 | Sekins et al. ................. 604/56 | WO | WO 90/04384 | 5/1990 |
| 5,707,606 A | 1/1998 | Quay ........................ 424/9.52 | WO | WO 90/04943 | 5/1990 |
| 5,707,607 A | 1/1998 | Quay ........................ 424/9.52 | WO | WO 91/00086 | 1/1991 |
| 5,711,933 A | 1/1998 | Bichon et al. .............. 424/9.52 | WO | WO 91/03267 | 3/1991 |
| 5,716,597 A | 2/1998 | Lohrmann et al. ............ 424/9.5 | WO | WO 91/09629 | 7/1991 |
| 5,732,707 A | 3/1998 | Widder et al. ......... 128/661.08 | WO | WO 91/12823 | 9/1991 |
| 5,733,527 A | 3/1998 | Schutt ........................ 424/9.52 | WO | WO 91/15244 | 10/1991 |
| 5,736,121 A | 4/1998 | Unger ........................ 424/9.4 | WO | WO 91/18612 | 12/1991 |
| 5,740,807 A | 4/1998 | Porter .................. 128/662.02 | WO | WO 92/05806 | 4/1992 |
| 5,770,222 A | 6/1998 | Unger et al. ................. 424/450 | WO | WO 92/10166 | 6/1992 |
| 5,804,162 A | 9/1998 | Kabalnov et al. .......... 424/9.51 | WO | WO 92/11873 | 7/1992 |
| 5,830,430 A | 11/1998 | Unger et al. ................. 424/1.21 | WO | WO 92/15284 | 9/1992 |
| 5,840,023 A | 11/1998 | Oraevsky et al. ............. 600/407 | WO | WO 92/17212 | 10/1992 |
| 5,846,517 A | 12/1998 | Unger ....................... 424/9.52 | WO | WO 92/17213 | 10/1992 |
| 5,849,727 A | 12/1998 | Porter et al. ................. 514/156 | WO | WO 92/17436 | 10/1992 |
| 5,855,865 A | 1/1999 | Lambert et al. ........... 424/9.52 | WO | WO 92/17514 | 10/1992 |
| 5,858,399 A | 1/1999 | Lanza et al. ................. 424/450 | WO | WO 92/21382 | 12/1992 |
| 5,874,062 A | 2/1999 | Unger ........................ 424/9.4 | WO | WO 92/22247 | 12/1992 |
| 5,897,851 A | 4/1999 | Quay et al. ................. 424/9.52 | WO | WO 92/22249 | 12/1992 |
| 5,925,011 A | 7/1999 | Faict et al. .................... 604/29 | WO | WO 92/22298 | 12/1992 |
| 5,935,437 A | 8/1999 | Whitmore ............... 210/321.6 | WO | WO 93/00933 | 1/1993 |
| 5,976,501 A | 11/1999 | Jablonski ................... 424/9.52 | WO | WO 93/05819 | 1/1993 |
| 5,997,898 A | 12/1999 | Unger ........................ 424/450 | WO | WO 93/06869 | 4/1993 |
| 6,056,938 A | 5/2000 | Unger et al. ................. 424/1.21 | WO | WO 93/09762 | 5/1993 |
| 6,068,857 A | 5/2000 | Weitschies et al. ........... 424/489 | WO | WO 93/13809 | 7/1993 |
| 6,159,445 A | 12/2000 | Klaveness et al. ........... 424/9.6 | WO | WO 93/17718 | 9/1993 |
| 6,261,537 B1 | 7/2001 | Klaveness et al. ......... 424/9.52 | WO | WO 93/20802 | 10/1993 |
| 6,331,289 B1 | 12/2001 | Klaveness et al. ......... 424/9.52 | WO | WO 94/00110 | 1/1994 |
| | | | WO | WO 94/06477 | 3/1994 |
| | FOREIGN PATENT DOCUMENTS | | WO | WO 94/07539 | 4/1994 |
| AU | B-30351/89 | 3/1993 | WO | WO 94/09829 | 5/1994 |
| DE | 25 21 003 | 8/1976 | WO | WO 94/16739 | 8/1994 |
| | | | WO | WO 94/18954 | 9/1994 |

| | | |
|---|---|---|
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 94/28874 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/32005 | 11/1995 |
| WO | WO 95/32006 | 11/1995 |
| WO | WO 96/04018 | 2/1996 |
| WO | WO 96/08234 | 3/1996 |
| WO | WO 96/09793 | 4/1996 |
| WO | WO 96/25942 | 8/1996 |
| WO | WO 96/36286 | 11/1996 |
| WO | WO 96/39197 | 12/1996 |
| WO | WO 96/40281 | 12/1996 |
| WO | WO 96/40285 | 12/1996 |
| WO | WO 86/00238 | 1/1998 |
| WO | WO 98/00172 | 1/1998 |
| WO | WO 98/04292 | 2/1998 |
| WO | WO 98/16203 | 4/1998 |
| WO | WO 98/42384 | 10/1998 |
| WO | WO 99/13919 | 3/1999 |
| WO | WO 99/33940 | 7/1999 |
| WO | WO 99/39738 | 8/1999 |
| WO | WO 99/52505 | 10/1999 |
| WO | WO 01/15742 A1 | 3/2001 |

OTHER PUBLICATIONS

Hope, et al., "Production of large unilamellar vesicles by a rapid extrusion procedure. Characterization of size distribution, trapped volume, and ability to maintain a membrane potential," *Biochimica et Biophysica Acta*, 812, 55-65.

Cheng, et al., "The production and evaluation of contrast-carrying liposomes made with an automatic high pressure system," *Investigative Radiology*, 1987, 22(1), 47-55.

Jain, et al., "Facilitated Transport", *Introduction to Biological Membranes*, Ch. 9, pp. 192-231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long-chain Saturated Phosphatidylcholines by Extrusion Technique", *Biochimica et Biophysica Acta*, vol. 986, pp. 200-206 (1989).

Hope et al., "Generation of Multilamellar and Unilamellar Phospholipid Vesicles", *Chemistry and Physics of Lipids*, vol. 40, pp. 89-107 (1986).

Mattrey et al., "Perfluorochemicals as US Contrast Agents for Tumor Imaging and Hepatosplenography: Preliminary Clinical Results", *Radiology*, vol. 163, No. 2, pp. 339-343 (1987).

Mattrey et al., "Perfluroctylbromide: A Liver/Spleen-Specific and Tumor-Imaging Ultrasound Contrast Material", *Radiology*, vol. 145, pp. 759-762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570-575 (1987).

Feinstein et al., "Two-Dimensional Contrast Echocardiography. I. In Vitro Development and Quantitative Analysis of Echo Contrast Agents", *JACC*, vol. 3, No. 1, pp. 14-20 (1984).

Ten Cate et al., "Two-Dimensional Contrast Echocardiography. II: Transpulmonary Studies", *JACC*, vol. 3, No. 1, pp. 21-27 (1984).

Unger et al., "Hepatic Metastases: Liposomal Gd-DTPA-enhanced MR Imaging", *Radiology*, vol. 171, No. 1, pp. 81-85 (1989).

Deamer et al., "Permeability of Lipid Bilayers to Water and Ionic Solutes", *Chemistry and Physics of Lipids*, vol. 40, pp. 167-188 (1986).

Gutknecht et al., "Diffusion of carbon dioxide through lipid bilayer membranes. Effects of carbonic anhydrase, bicarbonate, and unstirred layers", *Chemical Abstracts*, vol. 87, 34772q, p. 136 (1977).

Scarpa et al., "Cation Permeability of Liposomes as a Function of the Chemical Composition of the Lipid Bilayers", *Biochimica et Biophysica Acta*, vol. 241, pp. 789-797 (1971).

MacNaughton et al., "Effects of Gaseous Anaesthietics and Inert Gases on the Phase Transition in Smectic Mesophases of Dipalmitoyl Phosphatidylcholine", *Biochimica et Biophysica Acta*, vol. 597, pp. 193-198 (1980).

Tilcock et al., "Liposomal Gd-DTPA: Preparation and Characterization of Relaxivity", *Radiology*, vol. 171, No. 1, pp. 77-80 (1989).

Mann et al., "Formaiton of Iron Oxides in Unilamellar Vesicles" *Journal of Colloid and Interface Science*, vol. 122, No. 2, pp. 326-335 (1988).

Anderson et al., "Manganese (III) Complexes in Oxidative Decarboxylation of Acids", *J. Am. Chem. Soc.*, vol. 92, No. 8, pp. 2450-2460 (1970).

Muhlradt et al., "Vitamin B6 Analogs: An Improved Synthesis of 5-Deoxypyridoxal", *New Compounds*, vol. 10, pp. 129-130 (1967).

Chapman, "Physiochemical Properties of Phospholipids and Lipid-Water Systems", *Liposome Technology*, Gregoriadis, G., ed., Chapter 1, vol. 1, pp. 1-18 (CRC Press, Boca Raton, FL, 1984).

Violante et al., "Particulate Suspensions as Ultrasonic Contrast Agents for Liver and Spleen", *Inv. Rad.*, vol. 23, pp. S294-S297, Sep. 1988.

Fritzsch et al., "Preclinical and Clinical Results with an Ultrasonic Contrast Agent", *Inv. Rad.*, vol. 23, pp. S302-S305, Sep. 1988.

Brochure, *Experience*, Sonicator™, Heat Systems-Ultrasonics, Inc. (1987).

M. Ostro, "Liposomes", Marcel Dekker, New York, pp. 102-103 (1983).

Fukuda et al., "Polymer-Encased Vesicles Derived from Dioctadecyldimethylammonium Methacrylate", *J. Am. Chem. Soc.*, vol. 108, pp. 2321-2327 (1986).

Regen, "Polymerized Vesicles", *J. Am. Chem. Soc.*, vol. 102, pp. 6638-6640 (1980).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322-326 (1981) (abstract).

J. Vion-Dury et al., *J. Pharmacol. Exper. Ther.*, vol. 250(3), pp. 1113-1118 (1989) (abstract).

M.R. Zalutsky et al., *Invest. Radiol.*, vol. 22(2), pp. 141-147 (1987) (abstract).

Crowe et al., "Preservation of Freeze-Dried Liposomes by Trehalose", *Archives of Biochemistry and Biophysics*, vol. 242, pp. 240-247 (1985).

Crowe et al., "Preservation of Structural and Functional Activity in Lyophilized Sarcoplasmic Reticulum", *Archives of Biochemistry and Biophysics*, vol. 220, pp. 477-484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1-18, 30-35, 51-65 and 79-107 (CRC Press Inc., Boca Raton, FL, (1984).

Madden et al., "The accumulation of drugs within large unilamellar vesicles exhibiting a proton gradient: a survey", *Chemistry and Physics of Lipids*, vol. 53, pp. 37-46 (1990).

Sinkula et al., "Rationale for Design of Biologically Reversible Drug Derivatives: Prodrugs", *J. Pharm. Sci.*, vol. 64, No. 2, pp. 181-210 (1975).

Shiina et al., "Hyperthermia by Low-frequency Synthesized Ultrasound", *IEEE Engineering*, pp. 879-880, vol. 2 (1988) (abstract).

McAvoy et al., *IEEE Engineering, Ultrasonics Symposium Proceedings*, vol. 2, pp. 677-1248 (1989) (abstract).

Chapman et al., "Biomembrane Phase Transitions", *J. Biol. Chem.*, vol. 249, pp. 2512-2521 (1974).

Hug et al., "Liposomes for the Transformation of Eukaryotic Cells", *Biochimica et Biophysica Acta*, 1991, 1097:1-17.

Acoustic Imaging; AI5200; Convex Curved Linear Array Ultrasound Transducers Operator's Manual, Nov. 20, 1989, 4700-0003-1C, p. 4.

Bangham et al., "Diffusion of Univalent Ions across the Lamellae of Swollen Phospholipids", *J. Mol. Biol.*, 1965, 13:238-252.

Carson et al., "Ultrasound Power and Intensities Produced By Diagnostic Ultrasound Equipment", *Ultrasound in Med & Biol.*, vol. 3, pp. 341-350 (1978).

Kost et al., *Polymers in Medicine II: Biomedical and Pharmaceutical Applications*, "Ultrasonic Modulated Drug Delivery Systems", Chiellini et al., eds., (Plenum Press, New York and London), pp. 387-396 (1985).

deGier et al., "Relations Between Liposomes and Biomembranes", *Annals of New York Academy of Sciences*, vol. 308, pp. 85-99 (1978).

Felgner et al., "Lipofection: A highly efficient, lipid-mediated DNA-transfection procedure", *Proc. Natl. Acad. Sci.*, vol. 84, pp. 7413-7417 (1987).

Gabizon et al., "Liposome formulations with prolonged circulation time in blood and enhanced uptake by tumors", *Proc. Natl. Acad. Sci.*, vol. 85, pp. 6949-6953 (1988).

Garelli, et al., "Incorporation of new amphiphilic perfluoroalkylated bipyridine platinum and palladium complexes into liposomes: stability and . . . " *Biochimica et Biophysica Acta*, vol. 1127, pp. 41-48 (1992).

Kawai et al., "New Procedure for DNA Transfection with Polycation and Dimethyl Sulfoxide", *Molecular and Cellular Biology*, vol. 4, No. 6, pp. 1172-1174 (1984).

Kuo et al., "Metallocene Antitumor Agents. Solution and Solid-State Molybdenocene Coordination . . . ", *J. Am. Chem. Soc.*, vol. 113, No. 24, pp. 9027-9045 (1991).

MacDonald, *Mammalian Cell Biotechnology: A Practical Approach*, M. Butler, ed., (Oxford University Press, New York), Chapter 4, pp. 57-70 (1991).

Mathiowitz et al., "Photochemical Rupture of Microcapsules: A Model System", *Journal of Applied Polymer Science*, vol. 26, pp. 809-822 (1981).

May et al., "Cationic Liposomes Enable Bovine Herpesvirus Type 2 DNA to Infect Cells", *Acta virol.*, 1991, 35:107.

Poznansky et al., "Biological Approaches to the Controlled Delivery of Drugs: A Critical Review", *Pharmacol. Rev.*, vol. 36, No. 4, pp. 277-336 (1984).

Sato et al., "Recent Aspects In The Use Of Liposomes In Biotechnology And Medicine", *Prog. Lipid Res.*, vol. 31, No. 4, pp. 345-372 (1992).

Simons et al., "Antisense c-myb oligonucleotides inhibit intimal arterial smooth muscle cell accumulation in vivo", *Nature*, vol. 359, pp. 67-70 (1992).

Thompson, "At Age 2, Gene Therapy Enters a Growth Phase", *Science*, vol. 258, pp. 744-746 (1992).

Trubetskoy et al., "Cationic liposomes enhance targeted delivery and expression of exogenous DNA . . . " *Biochimica et Biophysica Acta*, vol. 1131, pp. 311-313 (1992).

Umemura et al., "Studies on Sonodynamic Cancer Therapy", *IEEE*, O-7803-0785, pp. 354-355 (1992).

Williams, "Human Gene Therapy: Searching for Better Vectors", *ASM News* [American Society for Microbiology] vol. 58, pp. 67-69 (1992).

Woodle et al., "Versatility in lipid compositions showing prolonged circulation . . .", *Biochimica et Biophysica Acta* 1992, 1105:193-200.

Zhou et al., "Targeted delivery of DNA by liposomes and polymers", *J. of Controlled Release*, vol. 19, pp. 269-274 (1992).

Mathiowitz et al., "Polyanhydride Microspheres as Drug Carriers. II. Microencapsulation by Solvent Removal", *Journal of Applied Polymer Science*, vol. 35, pp. 755-774 (1988).

Sankaram et al., "Cholesterol-Induced Fluid-Phase Immiscibility in Membranes", *Proc. Natl. Acad. Sci.*, vol. 88, pp. 8686-8690 (1991).

*Scientific Apparatus Catalog 92/93* (VWR Scientific, 1991), "Syringes", pp. 1511-1513; "Filtration, Syringe Filters", pp. 766-768; "Filtration, Membranes", pp. 750-753; "Filtration, Filter Holders", p. 744.

Gramiak et al., "Detection of Intracardiac Blood Flow by Pulsed Echo-Ranging", *Radiology*, vol. 100, pp. 415-418 (1971).

Feigenbaum et al., *Circulation*, "Identification of Ultrasound Echoes from the Left Ventricle by Use of Intracardiac Injections of Indocyanine Green", vol. XL1, pp. 615-621 (Apr. 1970).

Santaella, et al., "Extended In Vivo Blood Circulation Time of Fluorinated Liposomes", *FEBS 13463*, vol. 336, No. 3, pp. 481-484 (1993).

Brown and Langer, *Annual Review Medicine*, 1988, 39:221 29, Annual Review, Inc., "Transdermal Delivery of Drugs", pp. 221-229.

Moseley, et al., *Microbubbles: A Novel MR Susceptibility Contrast Agent*, abstract, 1991 Napa, California Meeting of the Society for Magnetic Resonance in Medicine.

Ter-Pogossian, "Physical Principles and Instrumentation", *Computed Body Tomography*, Lee, et al., eds., Raven Press, New York, Chapter 1, pp. 1-7 (1988).

Aronberg, "Techniques", *Computed Body Tomography*, Lee, et al., eds., Raven Press, New York, Chapter 2, pp. 9-36 (1988).

Miller, *Ultrasonics* (Sep. 1981), "Ultrasonic detection of resonant cavitation bubbles in a flow tube by their second-harmonic emissions", pp. 217-224.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Deasy, Microencapsulation and Related Drug Processes, vol. 20, Chs. 9 and 10, pp. 195-239 (1983) (Marcel Dekker, Inc., NY).

Yeung et al., "Preparation of Microencapsulated Liposomes", *J. Microencapsulation*, 1988, 5, 331-337.

Pantely, "Intravenous Contrast Echocardiography-Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188-S190 (Aug. 1996).

Frézard, et al., "Permeability and stability in buffer and in human serum of fluorinated phospholipid-based liposomes", *Biochimica et Biophysica Acta*, 1192, pp. 61-70 (1994).

Frézard, et al., "Fluorinated Phospholipid-Based Vesicles as Potential Drug Carriers: Encapsulation/Sustaining of Drugs and Stability in Human Serum", *Art, Cells, Blood Subs., and Immob. Biotech.*, 22(4), pp. 1403-1408 (1994).

Chang, "Semipermeable Aqueous Microcapsules", *Canadian J. Of Phys. And Pharm.*, 1966, vol. 44, pp. 115-128 (1978).

Chang, "Semipermeable Microcapsules", *Science*, 1964, 146, 524-525.

Lincoff et al., "Intravitreal Longevity of Three Perfluorocarbon Gases", *Arch. Ophthalmol.*, vol. 98, pp. 1610-1611, Sep. 1980.

Lincoff et al., "The Perfluorocarbon Gases in the Treatment of Retinal Detachment", *Ophthalmology*, vol. 90, No. 5, pp. 546-551, May 1983.

Mattrey et al., *Gas Emulsions as Ultrasound Contrast Agents: Preliminary Results in Rabbits and Dogs, Investigative Radiology*, vol. 29, Jun. Supp. 2, pp. S139-S141, 1994.

Meltzer et al., *Transmission of Ultrasonic Contrast Through the Lungs*, Ultrasound in Med. & Biol., vol. 7, No. 4, 377-384, 1981. PR Newswire, Apr. 1, 1986.

Swanson et al., "Enhancement Agents for Ultrasound: Fundamentals", *Pharmaceuticals In Medical Imaging*, Chapter 22, pp. 682-687 (1990).

Ophir et al., "Contrast Agents in Diagnostic Ultrasound", *Ultrasound in Med & Biol.*, vol. 15, No. 4, pp. 319-333 (1989).

Jacobs, "Intraocular gas measurement using A-scan ultrasound", *Current Eye Research*, vol. 5, No. 8, pp. 575-578 (1986).

Lincoff et al., "Intravitreal Expansion of Perfluorocarbon Bubbles", *Arch. Ophthalmol.*, vol. 98, p. 1646, Sep. 1980.

Miller et al., "Physiochemical Approaches to the Mode of Action of General Anesthehics", *J. Amer. Soc. Anesthesiologists*, 36(4):339-351 (1972).

"Properties and Applications of the 'Freon' Fluorocarbons" in DuPont Freon Technical Bulletin B-2 (E.I. DuPont de Nemours and Company, Wilmington, DE), pp. 1-11 (1964).

Gardner et al., "A Survey of Intraocular Gas Use in North America", *Arch. Ophthalmol.*, vol. 106, pp. 1188-1189, Sep. 1988.

Unger et al., "Liposomal MR Contrast Agents", *J. Liposome Research*, 4(2), pp. 811-834 (1994).

Feinstein, Steven B., "Myocardial Perfusion Imaging: Contrast Echocardiography Today and Tomorrow", *Journal of the American College of Cardiology*, 8(1):251-253 (1986).

Keller et al., "The Behavior of Sonicated Albumin Microbubbles Within the Microcirculation: A Basis for Their Use During Myocardial Contrast Echocardiography", *Circulation Res.*, vol. 65, No. 2, pp. 458-467 (Aug. 1989).

Lincoff et al., "Perfluoro-n-butane: A Gas for Maximum Duration Retinal Tamponade", *Arch Ophthalmology*, 101:460-462 (1983).

*Remington's Pharmaceutical Sciences*, John Hoover, managing ed., Mack Publishing Company, Easton, PA, pp. 295-298; 736; 1242-1244 (1975).

*Handbook of Pharmaceutical Excipients*, American Pharmaceutical Association, Washington, D.C. and The Pharmaceutical Society of Great Britain, London, England, pp. 181-183 (1986).

Barnhart et al., "Characteristics of ALBUNEX™: Air-Filled Microspheres for Echocardiography Contrast Enhancement", *Investigative Radiology*, 25:S162-164 (Sep. 1990).

Levene et al., "Characterization of ALBUNEX™," *J. Acoust. Soc. Am.*, 87 (Suppl. 1):569-70 (Spring 1990).

Nomura et al., "US Contrast Enhancement of Hepatic Tumor with Helium Gas Microbubbles: A Preliminary Report", *Jpn. J. Med. Ultrasonics*, vol. 18, No. 5 (1991) (Japanese with English language abstract).

Lindner et al., "Myocardial Perfusion Characteristics and Hemodynamic Profile of MRX-115, a Venous Echocardiographic Contrast Agent, During Acute Myocardial Infarction", *J. Am. Soc. of Echocardiography*, vol. 11, No. 1, pp. 36-46 (Jan. 1998).

"'Freon' Fluorocarbons: Properties and Applications" in DuPont Technical Bulletin G-1 (E.I. DuPont de Nemours and Company, Wilmington, DE), pp. 1-10 (1987).

"Encyclopedia of Polymer Science and Engineering", John Wiley & Sons, New York, 1:164-169 (1985).

"Concise Encyclopedia of Polymer Science and Engineering", J. Kroschwitz, ed., John Wiley & Sons, New York, pp. 12-13 (1990).

Wheatley et al., "Contrast Agents for Diagnostic Ultrasound: Development and Evaluation of Polymer-Coated Microbubbles", *Biomaterials*, 11:713-717 (1990).

Villanueva et al., "Characterization of Spatial Patterns of Flow Within the Reperfused Myocardium by Myocardial Contrast Echocardiography", *Circulation*, vol. 88, No. 6, pp. 2596-2606 (Dec. 1993).

Desir et al., "Assessment of regional myocardial perfusion with myocardial contrast echocardiography in a canine model of varying degrees of coronary stenosis", *American Heart Journal*, vol. 127, No. 1, pp. 56-63 (Jan. 1994).

Sekins et al., "Lung Cancer Hyperhermia via Ultrasound and PFC Liquids", *Published in Proceedings of 5th International Symposium on Hyperthermic Oncology, Kyoto, Japan*, (3 pages) (Aug. 29-Sep. 3, 1998).

Pietersen, "A New Warning System for Fires of Electrical Origin", *CERN European Organization for Nuclear Research, Health and Safety Division*, pp. 1-5 (Mar. 1977).

Yang et al., "Exposure to Low-Intensity Ultrasound Increases Aggrecan Gene Expression in a Rat Femur Fracture Model". *Journal of Orthopaedic Research*, vol. 14, No. 5, pp. 802-809, 1996.

Young et al., "Effect of therapeutic ultrasound on the healing of full-thickness excised skin lesions". *Ultrasonics*, vol. 28, No. 3, pp. 175-180, 1990.

Regen et al., "Polymerized Phosphatidylcholine Vesicles. Synthesis and Characterization", *J. Am. Chem. Soc.*, vol. 104, No. 3, pp. 191-195 (1982).

Wei et al., "Quantification of Myocardial Blood Flow With Ultrasound-Induced Destruction of Microbubbles Administered as a Constant Venous Infusion", *Circulation*, vol 97, pp. 473-483 (1998).

Hynynen et al., "The Usefulness of a Contrast Agent and Gradient-Recalled Acquisition in a Steady-State Imaging Sequence for Magnetic Resonance Imaging-Guided Noninvasive Ultrasound Surgery", *Investigative Radiology*, vol. 29, pp. 897-903 (Oct. 1994).

Lejbkowicz et al., "The response of normal and malignant cells to ultrasound in vitro". Database *BIOSIS*, No. 1993:95122245 (abstract only).

Jackson et al., "Effect of ultrasound therapy on the repair of Achilles tendon injuries in rats". *Medicine And Science In Sports And Exercise*, vol. 23, No. 2, pp. 171-176, 1991.

Maxwell, "Therapeutic Ultrasound: Its Effects on the Cellular and Molecular Mechanisms of Inflammation and Repair". *Physiotherapy*, vol. 78, No. 6, pp. 421-426, Jun. 1992.

Tuncay et al., "Expression of Genes Associated with Tissue Remodeling Upon Ultrasound Perturbation in the Gingival Fibroblast". *Journal of Dental Research*, vol. 75, p. 143, 1996 (abstract only).

Wang et al., "Low Intensity Ultrasound Treatment Increases Strength in a Rat Femoral Fracture Model". *Journal of Orthopaedic Research*, vol. 12, No. 1, pp. 40-47, 1994.

Robinson, et al., F.J. Fry, ed., *Ultrasound: Its Applications In Medicine And Biology*, Elsevier Scientific Publishing Company, vol. 3, Chap. XI, pp. 593-596 (1978).

Silbernagl, Despopoulos, *Pocket Atlas of Physiology*, Georg Thieme Verlag, Stuttgart New York, pp. 156-157 (1983) (German language only).

Young et al., "The Effect of Therapeutic Ultrasound On Angiogenesis". *Ultrasound in Medicine and Biology*, vol. 16, No. 3, pp. 261-269, 1990.

Chortkoff et al., "Pharmacokinetics Do Not Explain the Absence of an Anesthetic Effect of Perfluoropropane or Perfluoropentane". *Anesth. Analg.*, 79, pp. 234-237, 1994.

Sharma et al., "Emulsification Methods For Perfluorochemicals". *Drug Development And Industrial Pharmacy*, 14 (15-17), pp. 2371-2376 (1988).

Tilcock et al., "PEG-coated Lipid Vesicles with Encapsulated Technetium-99m as Blood Pool Agents for Nuclear Medicine". *2211b Nuclear Medicine and Biology*, 21, No. 2, pp. 165-170, 1994.

Tilcock et al., "$^{99m}$Tc-labeling of Lipid Vesicles Containing the Lipophilic Chelator PE-DTTA: Effect of Tin-to-chelate Ratio, Chelate Content and Surface Polymer on Labeling Efficiency and Biodistribution Behavior". *2211b Nuclear Medicine and Biology*, 21, No. 1, pp. 89-96, 1994.

Zarif et al., "Synergistic Stabilization of Perfluorocarbon-Pluronic F-68 Emulsion by Perfluoroalkylated Polyhydroxylated Surfactants". *JAOCS*, vol. 66, No. 10, pp. 1515-1523, 1989.

Ding et al., *Chung Kuo Yao Li Hsueh Pao*, Sep. 1989; 10(5):473-5 (Abstract only).

Ring et al., *Clinical Weekly*, 52, pp. 595-598 (1974) (English abstract).

P.N.T. Wells, "Pulse-Echo Methods", *Biomedical Ultrasonics*, Academic Press, pp. 209-220 (1977).

Porter, et al., "Multifold Sonicated Dilutions of Albumin with Fifty Percent Dextrose Improve Left Ventricular Contrast Videointensity After Intravenous Injection in Human Beings", *Journal of the American Society of Echocardiography*, vol. 7, No. 5, pp. 465-471, Sep.-Oct. 1994.

Porter, et al., "Noninvasive Identification of Acute Myocardial Ischemia and Reperfusion With Contrast Ultrasound Using Intravenous Perfluoropropane-Exposed Sonicated Dextrose Albumin", *Journal of the American College of Cardiology*, vol. 26, No. 1, pp. 33-40; 1995.

H. Meessen, ed., *Microcirculation*, Springer-Verlag, Berlin Heidelberg, New York, p. 44 (1997) (German language only).

Kinsler, et al., *Fundamentals of Acoustics*, third ed., pp. 228-331 (1982).

Hautanen, et al., "Effects of Modifications of the RGD Sequence and Its Context on Recognition by the Fibronectin Receptor", *The Journal of Biological Chemistry*, vol. 264, No. 3, pp. 1437-1442, Jan. 25, 1999.

Takeuchi et al., "Enhanced Visualization of Intravascular Thrombus with the Use of a Thrombus Targeting Ultrasound Contrast Agent (MRX408): Evidence From in Vivo Experimental Echochardiographic Studies", *The Journal of the American College of Cardiology*, vol. 31, No. 2, Suppl. A, p. 57A, Abstract XP-000952675, Feb. 1998 and *47th Annual Scientific Session of American College of Cardiology*, Atlanta, GA, Mar. 29, 1998-Apr. 1, 1998.

Unger, et al., "In Vitro Studies of a New Thrombus-Specific Ultrasound Contrast Agent", *American Journal of Cardiology*, vol. 81, No. 12, Suppl. A, pp. 58G-61G, XP-002087505, Jun. 12, 1998 and *Symposium: Ninth International Congress on Echocardiography: Clinical Cardiology*, 1997.

Wu, et al., "Binding and Lysing of Blood clots Using MRX-408", *Investigative Radiology*, vol. 33, No. 12, pp. 880-885, XP-000952676, Dec. 1998.

Porter, et al., "Thrombolytic enhancement with perfluorocarbon-exposed sonicated dextrose albumin microbubbles", vol. 132, No. 5, *American Heart Journal*, pp. 964-968, Nov. 1996.

Gross, U., et al., "Phospholipid vesiculated fluorocarbons promising trend in blood substitutes", *Biomat. Art. Cells & Immob. Biotech.*, 1992, 20(2-4), 831-833.

Riess, J.G., "Fluorine in our arties", *New J. Chem.*, 1995, 19(8-9), 891-909 (English Abstract).

Porter, et al., "Visually Discernible Myocardial Echocardiographic Contrast After Intravenous Injection of Sonicated Dextrose Albumin Microbubbles Containing High Molecular Weight, Less Soluble Gases", *Journal of the American College of Cardiology*, vol. 25, No. 2, pp. 509-515, Feb. 1995.

Srinivasan, et al., "Characterization of Binding Sites, Extent of Binding, and Drug Interactions of Oligonucleotides with Albumin", *Antisense Research and Development*, vol. 5, pp. 131-139, 1995.

Xie, et al., "Acute Myocardial Ischemia and Reperfusion can be Visually Identified Non-invasively with Intravenous Perfluoropropane-Enhanced Sonicated Dextrose Albumin Ultrasound Contrast", *Circulation*, vol. 90, No. 4, Part 2, Abstract 2989, Oct. 1994.

Blomley et al., "Microbubble contrast agents: a new era in ultrasound"; Clinical Review XP008001399, *BMJ*, vol. 322, pp. 1222-1225 (May 19, 2001).

Guillod, F., et al., "Amphiphilic sugar phosphates with single or double perfluoroalkylated hydrophobic chains for use in oxygen and drug delivery systems", *Art. Cells, Blood subs. And Immob. Biotech.*, XP-001065196, 1994, 22(4), 1273-1279.

Riess, J.G., et al., "Advanced fluorocarbon-based systems for oxygen and drug delivery, and diagnosis", *Art. Cells, Blood Subs. And Immob. Biotech.*, XP-001064197, 1997, 25(1 & 2), 43-52.

Frezard, F., et al., "Fluorinated phosphatidylcholine-based liposomes: H+/Na+ permeability, active doxorubican encapsulation and stbility in human serum", *Biochim et Biophys Acta*, 1994, 1194, 61-68.

Ulendorf, "Physics of ultrasound contrast imaging, scattering in the linear range", *IEEE Transactions on Ultrasonics, Ferroelectrics, and Frequency Control*, 1994, 41(1), 70-79.

Van Liew, et al., "Relationship of oxygen content to $PO_2$ for stabilized bubbles in the circulation: theory", *J. Appl. Phyusiol.*, 1996, 81(1), 500-508.

Riess, J.G., "Introducing a new element fluorine-into the liposomal membrane", *J. Liposome Research*, 1995, 5(3), 413-430.

Santaella, C., et al., "Extended in vivo blood circulation time of fluorinated liposomes", *FEBS Ltrs.*, 1993, 336(3), 481-484.

Trevino, L., et al., "Incorporation of a perfluoroalkylalkane (rfrh) into the phospholipid bilayer of dmpc liposomes results in greater encapsulation stability", *J. Liposome Res.*, 1994, 4(2), 1017-1028.

Zarif, L., et al., "Biodistribution and excretion of a mixed flurocarbon-hydrocarbon "dowel" emulsion as determined by 19-F NMR", *Artificial Cells, Blood Subs. And Immob. Biotech.*, 1994, 22(4), 1193-1198.

Feinstein, S.B., "Myocardial perfusion imaging: contrast echocardiography today and tomorrow", *J. Am. College of Cardiology*, 1986, 8(1), 251-253.

Burkard, et al., "Oxygen transport to tissue by persistent bubbles: theory and simulations", *J. Appl. Physiol.*, 1994, 77(6), 2874-2878.

Canfield, et al., Incorporation of b-carotene into mixed micelles, *Methods in Enzymology.*, 1990, 189, 418-422.

Maa, et al., "Liquid-liquid emulsification by static mixers for use in microencapsulation", *J. Microencapsulation*, 1996, 13(4), 419-433.

Solomon, I., "Relaxation processes in a system of two spins", *Phys. Rev.*, 1995, 99(2), 559-565.

Sutherland, et al., "Color doppler myocardial imaging: a new technique for the assessment of myocardial function", *J. Am. Soc. Of Echocardiogr*, 1994, 7(5), 441-458.

Elgorab, et al., "Solubilization of b-carotene and retinol into aqueous solutions of mixed micelles", *Biochem Biophys. Acta.*, 1973, 306, 58-66.

Jing, et al., "Stable perfluorocarbon emulsions using XMO-10 as surfactant: potential oxygen-carying plasma expanders", *Biomat. Art. Cells Art. Org.*, 1990, 18(1), 107-117.

Johnson, et al., "Thermal stability of fluorocarbon emissions that transport oxygen", *Int. J. pharm.*, 1990, 59, 131-135.

Bloemberger, N., "Proton relaxation times in paramagnetic solutions", *J. Chem. Phys.*, 1957, 27(2), 572-573 and 595-596.

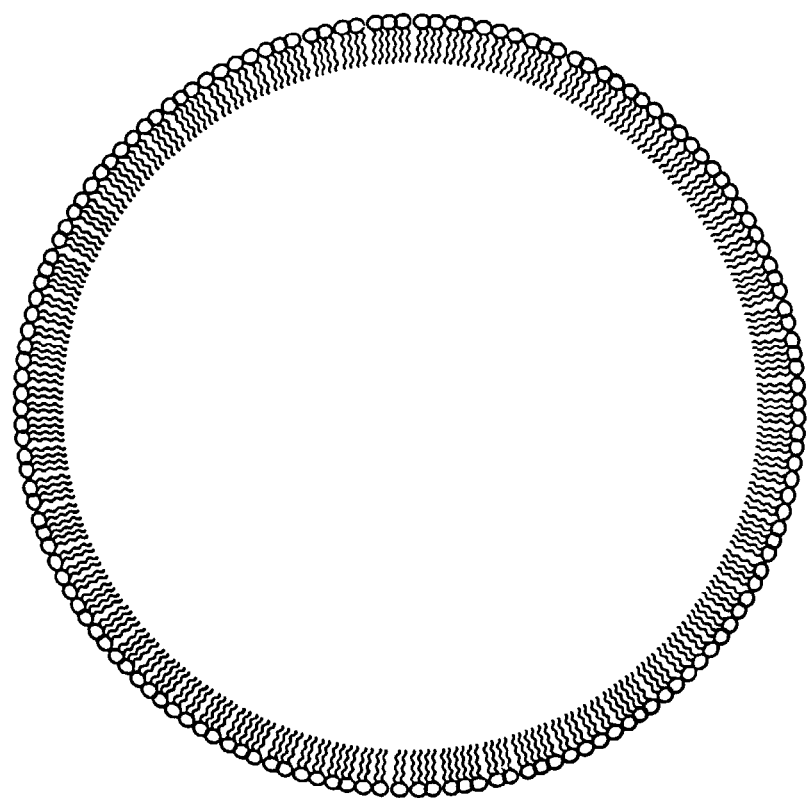
_Fig. 1c_
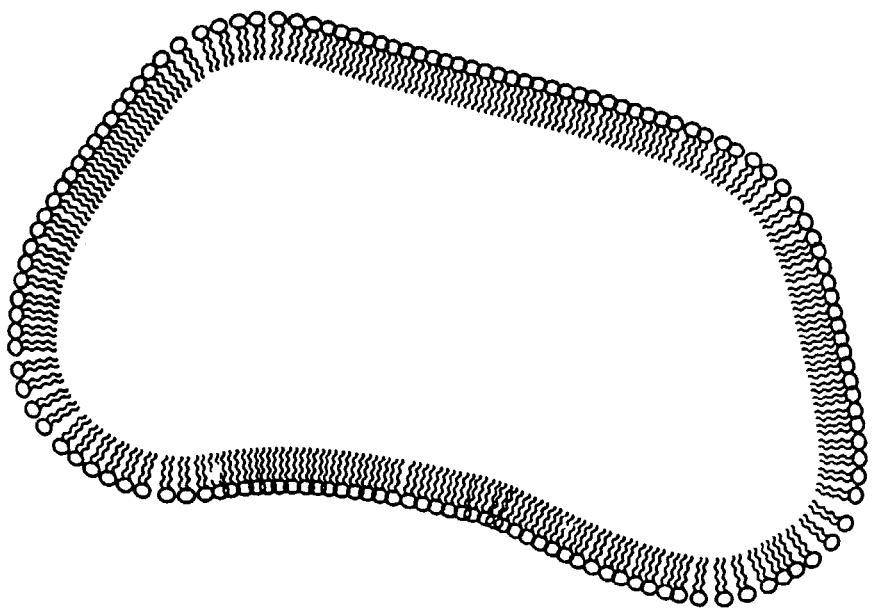
_Fig. 1d_

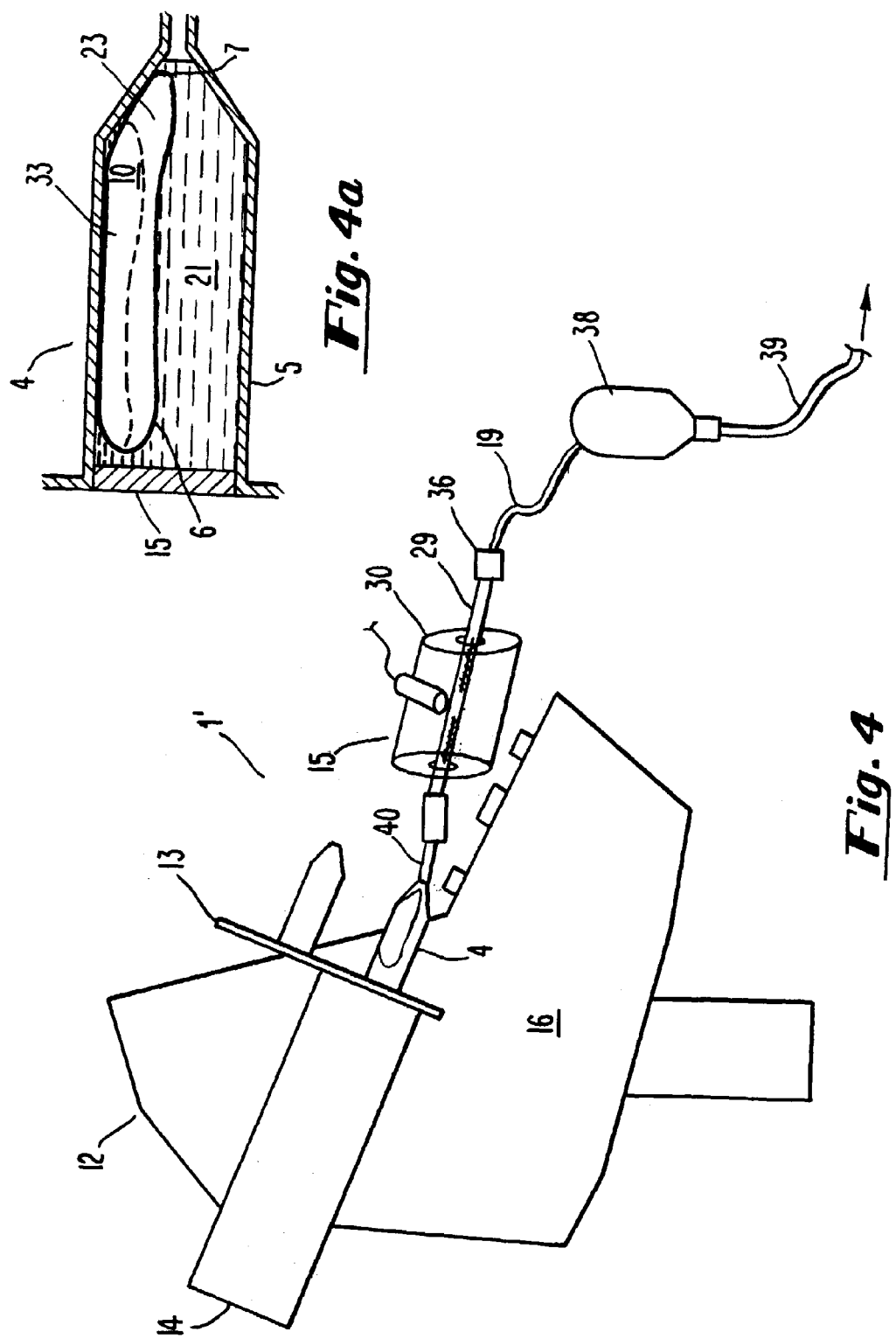

OXYGEN DELIVERY AGENTS AND USES FOR THE SAME

CROSS REFERENCE TO RELATED APPLICATIONS

This application is a divisional application of application Ser. No. 08/877,826, filed Jun. 18, 1997, now U.S. Pat. No. 6,537,246 now allowed.

FIELD OF THE INVENTION

The present invention describes, inter alia, oxygen delivery agents or blood substitutes comprising a fluorinated gas and a stabilizing material, methods of using the oxygen delivery agents or blood substitutes, and apparatus for making and delivering the oxygen delivery agents or blood substitutes.

BACKGROUND OF THE INVENTION

A theoretical assessment of oxygen delivery agents and the efficacy of loading and unloading oxygen is described from the standpoint of the partial pressures of oxygen in the lungs, blood, and tissues by Van Liew, et al., *J. Appl. Physiol.*, 81(1):500–508 (1996), and Burkard et al, *J. Appl. Physiol.*, 77(6):2874–2878 (1994). Liquid perfluorocarbons, such as perfluorooctylbromide, perfluorodecalin, perfluorotripropylamine and perfluorotributylamine, have been investigated as oxygen-transporting blood substitutes by, for example, Lowe, *Comp. Biochem. Physiol.*, 87A:825–838 (1987). However, these liquid perfluorocarbons boil at temperatures far above physiological conditions, and thus have a limited ability to thermally expand. This limitation imposes a practical constraint on the amount of infused liquid perfluorocarbon that may be administered to a patient in need of an oxygen-carrying blood substitute. Toxicity problems associated with liquid perfluorocarbon emulsions have also imposed significant limitations on their use, as described, for example, by Jing and Cooper, *Biomat. Art. Cells Art. Org.*, 18:107–117 (1990).

There is a need for oxygen delivery agents or blood substitutes that overcome the problems associated with the prior art. The present invention is directed to these, as well as other, important ends.

SUMMARY OF THE INVENTION

The present invention describes a method for oxygen delivery comprising administering to a patient a composition, in an aqueous carrier, comprising a fluorinated gas and a stabilizing material. The composition may further comprise oxygen before it is administered to the patient, or it may be administered without oxygen, whereby oxygen is added to the composition by the patient's own respiratory processes upon circulation through the patient's lungs. The method may also comprise imaging the patient with diagnostic ultrasound to monitor the location of the composition and applying therapeutic ultrasound to the patient to facilitate delivery of the oxygen in a desired region of the patient. The stabilizing material may be in a vesicular or non-vesicular form, as desired.

In another embodiment, the present invention describes an oxygen delivery vehicle or blood substitute comprising a composition which comprises a fluorinated gas and a stabilizing material. The composition further comprises oxygen. Preferably, the composition further comprises an aqueous carrier. The stabilizing material may be in a vesicular or non-vesicular form, as desired.

In another embodiment, the present invention describes an apparatus for making an oxygen delivery agent. The apparatus comprises (i) a first vessel containing a stabilizing material, (ii) a second vessel containing a fluorinated compound, (iii) means for mixing the stabilizing material and the fluorinated compound so as to form an oxygen delivery agent. In a preferred embodiment, the apparatus also includes a supply of oxygen and means for introducing oxygen from the supply into the mixture so as to form an oxygen carrying oxygen delivery agent. Preferably, at least one of the vessels is formed by the barrel of a syringe. In one embodiment, the mixing means comprises (i) a device for inducing turbulence into the mixture of stabilizing material and fluorinated compound and (ii) a device for agitating the mixture. The apparatus may further comprise a device for evacuating the contents of the vessels. In one embodiment, the evacuation device comprises a programmable mechanical injector. In another embodiment, the evacuation device comprises a disposable pressurized gas cylinder.

These and other aspects of the invention will become more apparent from the following detailed description.

BRIEF DESCRIPTION OF THE DRAWINGS

FIG. 1C is a cross-sectional view of a hypothetical monolayer vesicle (not drawn to scale). FIG. 1D is a cross-sectional view of a hypothetical semi-collapsed monolayer vesicle (not drawn to scale).

FIG. 4 is a diagram, partially schematic, of a second embodiment of the apparatus of the current invention.

FIG. 4a is a detailed view of a longitudinal cross-section through the syringe shown in FIG. 4.

DETAILED DESCRIPTION OF THE INVENTION

Figure 1A:
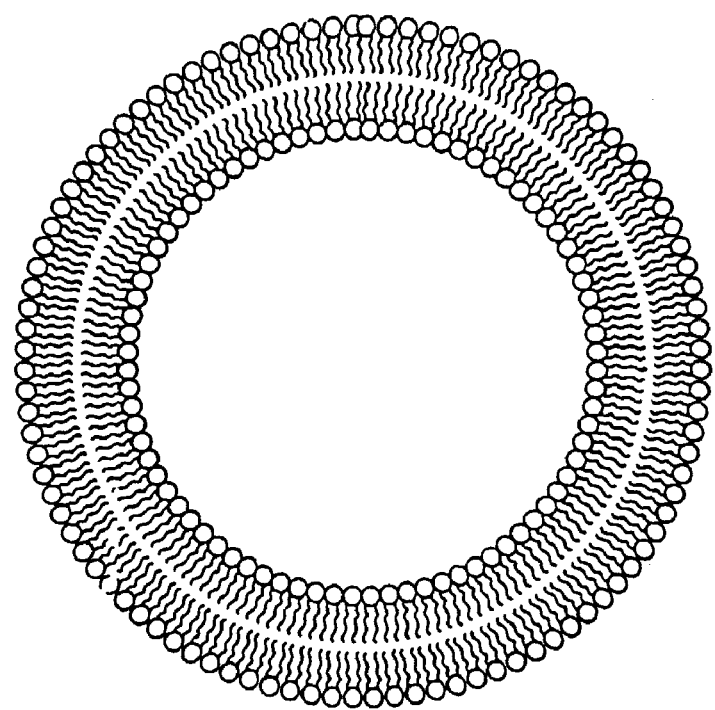
FIG. 1A is a cross-sectional view of a hypothetical bilayer vesicle (not drawn to scale).

As employed above and throughout the disclosure, the following terms, unless otherwise indicated, shall be understood to have the following meanings.

"Fluorinated gas" refers to a gaseous compound which contains at least one fluorine atom. Preferably, "fluorinated gas" refers to a gaseous compound that is polyfluorinated. "Polyfluorinated" refers to a compound which contains two or more fluorine atoms. More preferably, "fluorinated gas" refers to a gaseous compound that is perfluorinated. "Perfluorinated" refers to a compound where all the hydrogen atoms, except those whose replacement would substantially affect the nature of the characteristic groups present, have been replaced by fluorine atoms. "Fluorocarbon" denotes a fluorinated carbon compound wherein one or more hydrogen atoms directly attached to the carbon atoms are replaced by fluorine atoms. "Perfluorocarbon" denotes a fully fluorinated carbon compound wherein all hydrogen atoms directly attached to the carbon atoms are replaced by fluorine atoms.

"Oxygen" generally refers to oxygen atoms, oxygen molecules and isotopes of oxygen, including $^{15}O$, $^{15}O_2$, $^{16}O$, $^{16}O_2$, $^{17}O$, $^{17}O_2$, $^{18}O$, $^{18}O_2$ and combinations thereof. Preferably, the oxygen is $^{16}O$ or $^{16}O_2$, referred to herein and commonly as O or $O_2$, respectively.

"$Po_2$" refers to $O_2$ pressure.

"Oxygen delivery agent" and "oxygen delivery vehicle" refer to a composition, substance or material that is capable of transporting, dissolving and/or carrying oxygen in vivo or in vitro. Exemplary oxygen delivery agents or vehicles include, for example, stabilizing materials, vesicles, gas filled vesicles, liposomes, micelles, aerogels, clathrates, emulsions, suspensions, dispersion, hexagonal H II phase structures, and the like. Throughout the present disclosure, the terms "oxygen delivery agent" and "oxygen delivery vehicle" are used interchangeably with the term "blood substitute." As administered to a patient, the oxygen delivery vehicles described herein comprise a "gas." The term "gas" includes a gas and a gaseous precursor that has been converted to a gas, by, for example, temperature or pressure, prior to being administered to the patient. Preferably, a gaseous precursor is a compound that is converted to a gas at a temperature of about 80° C. or less, more preferably about 70° C. or less, still more preferably at about 60° C. or less, and most preferably at about 50° C. or less.

"Lipid" refers to a naturally-occurring, synthetic or semi-synthetic (i.e., modified natural) compound which is generally amphipathic. The lipids typically comprise a hydrophilic component and a hydrophobic component. Exemplary lipids include, for example, fatty acids, fluorinated lipids, neutral fats, phosphatides, oils, glycolipids, surface-active agents (surfactants and fluorosurfactants), aliphatic alcohols, waxes, terpenes and steroids. Semi-synthetic (or modified natural) denotes a natural compound that has been chemically modified in some fashion.

"Polymer" or "polymeric" refers to molecules formed from the chemical union of two or more repeating units. Accordingly, included within the term "polymer" may be, for example, dimers, trimers and oligomers. The polymer may be synthetic, naturally-occurring or semisynthetic. In a preferred form, "polymer" refers to molecules which comprise 10 or more repeating units.

"Protein" refers to molecules comprising, and preferably consisting essentially of, α-amino acids in peptide linkages. Included within the term "protein" are globular proteins such as albumins, globulins and histones, and fibrous proteins such as collagens, elastins and keratins. Also included within the term "protein" are "compound proteins," wherein a protein molecule is united with a nonprotein molecule, such as nucleoproteins, mucoproteins, lipoproteins and metalloproteins. The proteins may be naturally-occurring, synthetic or semi-synthetic.

"Surfactant" refers to a surface active agent, that is, a compound which alters surface tension. Surface active agents include, for example, detergents, wetting agents and emulsifiers.

"Vesicle" refers to an entity which is generally characterized by the presence of one or more walls or membranes which form one or more internal voids. Vesicles may be formulated, for example, from a stabilizing material such as a lipid, including the various a lipids described herein, a proteinaceous material, including the various proteins described herein, a polymeric material, including the various polymeric materials described herein, and a surfactant, including the various surfactants described herein. As discussed herein, vesicles may also be formulated from carbohydrates and other stabilizing materials, as desired. The lipids, proteins, polymers, surfactants and/or other vesicle forming stabilizing materials may be natural, synthetic or semi-synthetic (modified natural). Preferred vesicles are those which comprise walls or membranes formulated from lipids. The walls or membranes may be concentric or otherwise. The stabilizing compounds may be in the form of one or more monolayers or bilayers. In the case of more than one monolayer or bilayer, the monolayers or bilayers may be concentric. Stabilizing compounds may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The walls or membranes of vesicles may be substantially solid (uniform), or they may be permeable or semi-permeable. Preferably, the walls or membranes may be permeable to oxygen. The vesicles described herein include such entities commonly referred to as, for example, liposomes, micelles, bubbles, microbubbles, microspheres, lipid-coated bubbles, polymer-coated bubbles, protein-coated bubbles, nanospheres, microballoons, microcapsules, niosomes, aerogels, clathrate bound vesicles, hexagonal H II phase structures, and the like. The internal void of the vesicles may be filled with water, oil, gases and/or gaseous precursors, if desired, and/or other materials. Preferably, the internal void of the vesicles is filled with gases; more preferably with oxygen and at least one fluorinated gas; most preferably with oxygen and a gaseous perfluorocarbon.

"Liposome" refers to a generally spherical or spheroidal cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes formulated from non-ionic lipids may be referred to as niosomes.

"Micelle" refers to colloidal entities formulated from lipids. In certain preferred embodiments, the micelles comprise a monolayer, bilayer, or hexagonal H II phase structure.

"Aerogel" refers to generally spherical or spheroidal entities which are characterized by a plurality of small internal voids. The aerogels may be formulated from synthetic materials (for example, a foam prepared from baking resorcinol and formaldehyde), as well as natural materials, such as carbohydrates (polysaccharides) or proteins.

"Clathrate" refers to a solid, semi-porous or porous particle which may be associated with vesicles. In a preferred form, the clathrates may form a cage-like structure containing cavities which comprise one or more vesicles bound to the clathrate, if desired. A stabilizing material may, if desired, be associated with the clathrate to promote the association of the vesicle with the clathrate. Clathrates may be formulated from, for example, porous apatites, such as calcium hydroxyapatite, and precipitates of polymers and metal ions, such as alginic acid precipitated with calcium salts.

"Emulsion" refers to a mixture of two or more generally immiscible liquids, and is generally in the form of a colloid. The mixture may be of lipids, for example, which may be homogeneously or heterogeneously dispersed throughout the emulsion. Alternatively, the lipids may be aggregated in the form of, for example, clusters or layers, including monolayers or bilayers. An emulsion may be considered non-vesicular.

"Suspension" or "dispersion" refers to a mixture, preferably finely divided, of two or more phases (solid, liquid or gas), such as, for example, liquid in liquid, solid in solid, gas in liquid, and the like which preferably can remain stable for extended periods of time. A suspension or dispersion may be considered non-vesicular.

"Hexagonal H II phase structure" refers to a generally tubular aggregation of lipids in liquid media, for example, aqueous media, in which the hydrophilic portion(s) of the lipids generally face inwardly in association with an aqueous liquid environment inside the tube. The hydrophobic portion(s) of the lipids generally radiate outwardly and the complex assumes the shape of a hexagonal tube. A plurality of tubes is generally packed together in the hexagonal phase structure.

"Gas filled vesicle" refers to a vesicle having a gas, and/or a gaseous precursor that has been converted to a gas, by, for example, temperature or pressure, encapsulated therein. "Gaseous precursor filled vesicle" refers to a vesicle having a gaseous precursor encapsulated therein. The vesicles may be minimally, partially, substantially, or completely filled with the gas and/or gaseous precursor. The term "substantially" as used in reference to the gas and/or gaseous precursor filled vesicles means that greater than about 30% of the internal void of the substantially filled vesicles comprises a gas and/or gaseous precursor. In certain embodiments, greater than about 40% of the internal void of the substantially filled vesicles comprises a gas and/or gaseous precursor, with greater than about 50% being more preferred. More preferably, greater than about 60% of the internal void of the substantially filled vesicles comprises a gas and/or gaseous precursor, with greater than about 70% or 75% being more preferred. Even more preferably, greater than about 80% of the internal void of the substantially filled vesicles comprises a gas and/or gaseous precursor, with greater than about 85% or 90% being still more preferred. In particularly preferred embodiments, greater than about 95% of the internal void of the vesicles comprises a gas and/or gaseous precursor, with about 100% being especially preferred.

"Stabilizing material" or "stabilizing compound" refers to any material which is capable of improving the stability of compositions containing gases and/or gaseous precursors, including, for example, mixtures, suspensions, emulsions, dispersions, vesicles, or the like. The improved stability involves, for example, the maintenance of a relatively balanced condition, and may be exemplified, for example, by increased resistance of the composition against destruction, decomposition, degradation, and the like. In the case of preferred embodiments involving vesicles filled with gases and/or gaseous precursors, the stabilizing compounds may serve to either form the vesicles or stabilize the vesicles, in either way serving to minimize or substantially (including completely) prevent the escape of gases and/or gaseous precursors from the vesicles until said release is desired. The term "substantially," as used in the present context of preventing escape of gases and/or gaseous precursors from the vesicles, means greater than about 50% is maintained entrapped in the vesicles until release is desired, and preferably greater than about 60%, more preferably greater than about 70%, even more preferably greater than about 80%, still even more preferably greater than about 90%, is maintained entrapped in the vesicles until release is desired. In particularly preferred embodiments, greater than about 95% of the gases and/or gaseous precursors are maintained entrapped until release is desired. The gases and/or gaseous precursors may also be completely maintained entrapped (i.e., about 100% is maintained entrapped), until release is desired. Exemplary stabilizing materials include, for example, lipids, proteins, polymers, carbohydrates and surfactants. The resulting mixture, suspension, emulsion or the like may comprise walls (i.e., films, membranes and the like) around the gases and/or gaseous precursors, or may be substantially devoid of walls or membranes, if desired. The stabilizing material may, if desired, form droplets. The stabilizing material may also comprise salts and/or sugars. In certain embodiments, the stabilizing materials may be substantially (including completely) cross-linked. The stabilizing material may be neutral, positively or negatively charged. The stabilizing material may be vesicular or non-vesicular.

"Vesicle stability" refers to the ability of vesicles to retain the gas and/or gaseous precursor entrapped therein after being exposed, for about one minute, to a pressure of about 100 millimeters (mm) of mercury (Hg). Vesicle stability is measured in percent (%), this being the fraction of the amount of gas which is originally entrapped in the vesicle and which is retained after release of the pressure. Vesicle stability also includes "vesicle resilience" which is the ability of a vesicle to return to its original size after release of the pressure.

"Droplet" refers to a spherical or spheroidal entity which may be substantially liquid or which may comprise liquid and solid, solid and gas, liquid and gas, or liquid, solid and gas. Solid materials within a droplet may be, for example, particles, polymers, lipids, proteins, or surfactants.

"Cross-link," "cross-linked" and "cross-linking" generally refer to the linking of two or more stabilizing materials, including lipid, protein, polymer, carbohydrate and/or surfactant stabilizing materials, by one or more bridges. The bridges may be composed of one or more elements, groups, or compounds, and generally serve to join an atom from a first stabilizing material molecule to an atom of a second stabilizing material molecule. The cross-link bridges may involve covalent and/or non-covalent associations. Any of a variety of elements, groups, and/or compounds may form the bridges in the cross-links, and the stabilizing materials may be cross-linked naturally or through synthetic means. For example, cross-linking may occur in nature in material formulated from peptide chains which are joined by disulfide bonds of cystine residues, as in keratins, insulins and other proteins. Alternatively, cross-linking may be effected by suitable chemical modification, such as, for example, by combining a compound, such as a stabilizing material, and a chemical substance that may serve as a cross-linking agent, which may cause to react by, for example, exposure to heat, high-energy radiation, ultrasonic radiation and the like. Examples include cross-linking by sulfur to form disulfide linkages, cross-linking using organic peroxides, cross-linking of unsaturated materials by means of high-energy radiation, cross-linking with dimethylol carbamate, and the like. If desired, the stabilizing compounds may be substantially cross-linked. The term "substantially" means that greater than about 50% of the stabilizing compounds contain cross-linking bridges. If desired, greater than about 60%, 70%, 80%, 90%, 95% or even 100% of the stabilizing compounds contain such cross-linking bridges. Alternatively, the stabilizing materials may be non-cross-linked, i.e., such that greater than about 50% of the stabilizing compounds are devoid of cross-linking bridges, and if desired, greater than about 60%, 70%, 80%, 90%, 95% or even 100% of the stabilizing compounds are devoid of cross-linking bridges.

"Covalent association" refers to an intermolecular association or bond which involves the sharing of electrons in the bonding orbitals of two atoms.

"Non-covalent association" refers to intermolecular interaction among two or more separate molecules which does not involve a covalent bond. Intermolecular interaction is dependent upon a variety of factors, including, for example, the polarity of the involved molecules, and the charge (positive or negative), if any, of the involved molecules. Non-covalent associations are selected from ionic interactions, dipole-dipole interactions, van der Waal's forces, and combinations thereof.

"Ionic interaction" or "electrostatic interaction" refers to intermolecular interaction among two or more molecules, each of which is positively or negatively charged. Thus, for example, "ionic interaction" or "electrostatic interaction" refers to the attraction between a first, positively charged molecule and a second, negatively charged molecule. Ionic or electrostatic interactions include, for example, the attraction between a negatively charged stabilizing material, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole-dipole interaction" refers to the attraction of the uncharged, partial positive end of a first polar molecule, commonly designated as δ+, to the uncharged, partial negative end of a second polar molecule, commonly designated as δ−. Dipole-dipole interactions are exemplified by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" also refers to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"Hydrogen bond" refers to an attractive force, or bridge, which may occur between a hydrogen atom which is bonded covalently to an electronegative atom, for example, oxygen, sulfur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

"Hydrophilic interaction" refers to molecules or portions of molecules which may substantially bind with, absorb and/or dissolve in water. This may result in swelling and/or the formation of reversible gels.

"Hydrophobic interaction" refers to molecules or portions of molecules which do not substantially bind with, absorb and/or dissolve in water.

"Patient" refers to animals, including mammals, preferably humans.

"Region of a patient" refers to a particular area or portion of the patient and in some instances to regions throughout the entire patient. Exemplary of such regions are the gastrointestinal region, the cardiovascular region (including myocardial tissue), the renal region as well as other bodily regions, tissues, lymphocytes, receptors, organs and the like, including the vasculature, blood and circulatory system, and as well as diseased tissue, including cancerous tissue and tumors. "Region of a patient" includes, for example, regions to be imaged with diagnostic imaging, regions to be treated with oxygen, regions to be targeted for the delivery of oxygen, and regions of elevated temperature. The "region of a patient" is preferably internal, although, if desired, it may be external. The phrase "vasculature" denotes blood vessels (including arteries, veins and the like) and blood. The phrase "gastrointestinal region" includes the region defined by the esophagus, stomach, small and large intestines, and rectum. The phrase "renal region" denotes the region defined by the kidney and the vasculature that leads directly to and from the kidney, and includes the abdominal aorta.

"Biocompatible" refers to materials which are generally not injurious to biological functions and which will not result in any degree of unacceptable toxicity, including allergenic responses and disease states.

"Tissue" refers generally to specialized cells which may perform a particular function. The term "tissue" may refer to an individual cell or a plurality or aggregate of cells, for example, membranes or organs. The term "tissue" also includes reference to an abnormal cell or a plurality of abnormal cells. Exemplary tissues include blood, myocardial tissue, including myocardial cells and cardiomyocites, membranous tissues, including endothelium and epithelium, laminae, connective tissue, including interstitial tissue, and tumors.

"Intracellular" or "intracellularly" refers to the area within the plasma membrane of a cell, including the protoplasm, cytoplasm and/or nucleoplasm. "Intracellular delivery" refers to the delivery of a gas and/or gaseous precursor into the area within the plasma membrane of a cell. "Cell" refers to any one of the minute protoplasmic masses which make up organized tissue, comprising a mass of protoplasm surrounded by a membrane, including nucleated and unnucleated cells and organelles.

A wide variety of lipids may be used as stabilizing materials and vesicles in the present invention, for example, micelles and/or liposomes, and any of the materials or combinations thereof which are known to one skilled in the art are suitable for their preparation. The lipids may be of either natural, synthetic or semi-synthetic origin, including for example, fatty acids, fluorinated lipids, neutral fats, phosphatides, oils, glycolipids, surface active agents (surfactants and fluorosurfactants), aliphatic alcohols, waxes, terpenes and steroids.

Exemplary lipids which may be used to prepare the stabilizing materials of the present invention include, for example, fatty acids, lysolipids, fluorinated lipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC);

distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to herein as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN™, including TWEEN™ 20, TWEEN™ 40 and TWEEN™ 80, commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy) hexyl-6-amino-6-deoxyl-1-thio-α-D-mannopyranoside, 12-(((7'-diethylaminocoumarin-3-yl)carbonyl)methylamino)-octadecanoic acid: N-[12-(((7'-diethylaminocoumarin-3-yl) carbonyl)methylamino)-octadecanoyl]-2-aminopalmitic acid; cholesteryl(4'-trimethylammonio)butanoate; N-succinyldioleoyl-phosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycero-phosphoethanolamine and palmitoylhomocysteine, and/or any combinations thereof. In preferred embodiments, the stabilizing materials may comprise phospholipids, including one or more of DPPC, DPPE, DPPA, DSPC, DSPE, DSPG, and DAPC.

Examples of suitable fluorinated lipids include but are not limited to compounds of the formula:

$C_nF_{2n+1}(CH_2)_mC(O)O$ wherein m is 0 to about 18, n is 1 to about 12; and w is 1 to about 8. Examples of and methods for the synthesis of these, as well as other fluorinated lipids useful in the present invention, are set forth in U.S. application Ser. No. 08/465,868, filed Jun. 6, 1995, Reiss et al. U.S. Pat. No. 5,344,930, Frezard, F., et al., *Biochem Biophys Acta*, 1192:61–70 (1994), and Frezard, F., et al., *Art. Cells Blood Subs and Immob Biotech.*, 22:1403–1408 (1994), the disclosures of each of which are incorporated herein by reference in their entirety. One skilled in the art will appreciate that fluorinated derivatives of common phospholipids (diacyl glycerylphosphatidylcholine, diacylphosphatidyl serine, diacylphosphatidyl ethanolamine, diacylphosphatidyl glycerol, diacylphosphatidyl glycerol, etc.) as well as fluorinated derivatives of fatty acyl esters and free fatty acids may function in accordance with the scope of the invention. Additionally lipid based and fluorinated (including perfluorinated) surfactants may be used as stabilizing materials in the present invention.

Examples of polymerized lipids include unsaturated lipophilic chains such as alkenyl or alkynyl, containing up to about 50 carbon atoms. Further examples are phospholipids such as phosphoglycerides and sphingolipids carrying polymerizable groups, and saturated and unsaturated fatty acid derivatives with hydroxyl groups, such as for example triglycerides of d-12-hydroxyoleic acid, including castor oil and ergot oil. Polymerization may be designed to include hydrophilic substituents such as carboxyl or hydroxyl groups, to enhance dispersability so that the backbone residue resulting from biodegradation is water soluble. Exemplary polymerizable lipid compounds which may be utilized in the compositions of the present invention are illustrated below

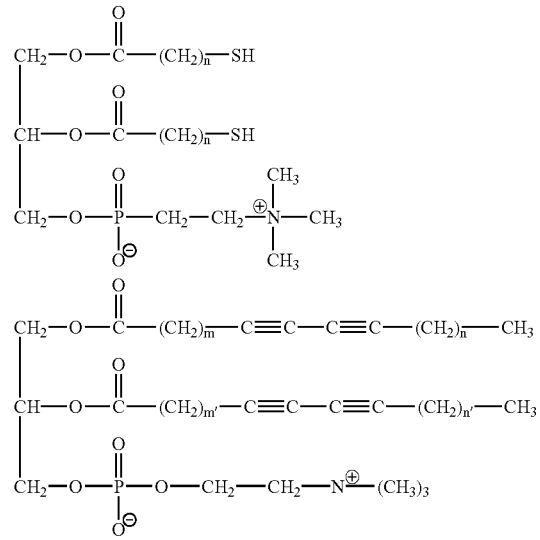

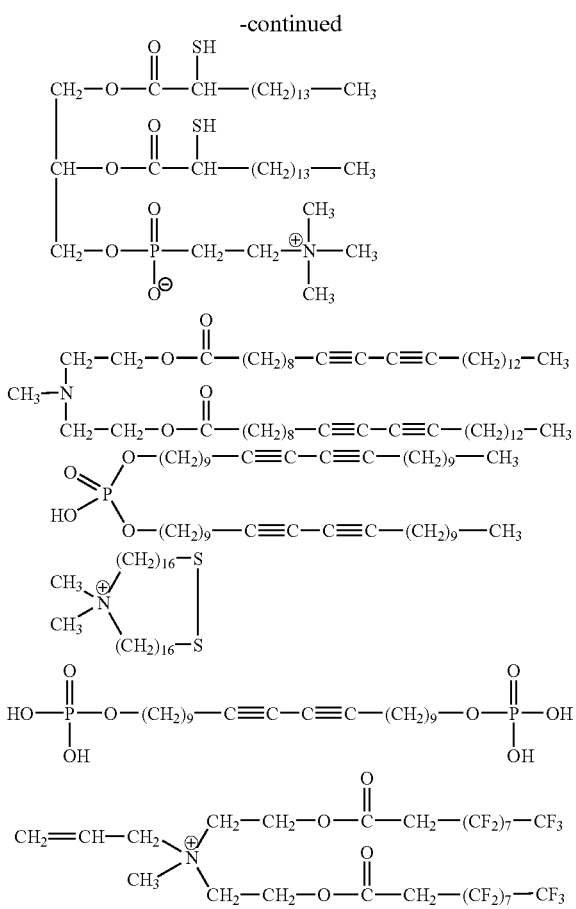

Suitable polymerizable lipids are also described, for example, by Klaveness et al, U.S. Pat. No. 5,536,490, the disclosure of which is hereby incorporated by reference herein in its entirety.

If desired, the stabilizing material may comprise a cationic lipid, such as, for example, N-[1-(2,3-dioleoyloxy) propyl]-N,N,N-trimethylammonium chloride (DOTMA), 1,2-dioleoyloxy-3-(trimethylammonio)propane (DOTAP); and 1,2-dioleoyl-3-(4'-trimethylammonio)butanoyl-sn-glycerol (DOTB). If a cationic lipid is employed in the stabilizing materials, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

If desired, aggregates may be constructed of one or more charged lipids in association with one or more polymer bearing lipids, optionally in association with one or more neutral lipids. The charged lipids may either be anionic or cationic. Typically, the lipids are aggregated in the presence of a multivalent species, such as a counter ion, opposite in charge to the charged lipid. For delivery of prodrugs and/or bioactive agents to selective sites in vivo, aggregates of preferably under 2 μm, more preferably under 0.5 μm, and even more preferably under 200 nm are desired. Most preferably the lipid aggregates are under 200 nm in size and may be as small as 5–10 nm in size.

Exemplary anionic lipids include phosphatidic acid and phosphatidyl glycerol and fatty acid esters thereof, amides of phosphatidyl ethanolamine such as anandamides and methanandamides, phosphatidyl serine, phosphatidyl inositol and fatty acid esters thereof, cardiolipin, phosphatidyl ethylene glycol, acidic lysolipids, sulfolipids, and sulfatides, free fatty acids, both saturated and unsaturated, and negatively charged derivatives thereof. Phosphatidic acid and phosphatidyl glycerol and fatty acid esters thereof are preferred anionic lipids.

When the charged lipid is anionic, a multivalent (divalent, trivalent, etc.) cationic material may be used to form aggregates. Useful cations include, for example, cations derived from alkaline earth metals, such as beryllium ($Be^{+2}$), magnesium ($Mg^{+2}$), calcium ($Ca^{+2}$), strontium ($Sr^{+2}$), and barium ($Ba^{+2}$); amphoteric ions such as aluminum ($Al^{+3}$), gallium ($Ga^{+3}$), germanium ($Ge^{+3}$), tin ($Sn^{+4}$), and lead ($Pb^{+2}$ and $Pb^{+4}$); transition metals such as titanium ($Ti^{+3}$ and $Ti^{+4}$), vanadium ($V^{+2}$ and $V^{+3}$), chromium ($Cr^{+2}$ and $Cr^{+3}$), manganese ($Mn^{+2}$ and $Mn^{+3}$), iron ($Fe^{+2}$ and $Fe^{+3}$), cobalt ($Co^{+2}$ and $Co^{+3}$), nickel ($Ni^{+2}$ and $Ni^{+3}$), copper ($Cu^{+2}$), zinc ($Zn^{+2}$), zirconium ($Zr^{+4}$), niobium ($Nb^{+3}$), molybdenum ($Mo^{+2}$ and $Mo^{+3}$), cadmium ($Cd^{+2}$), indium ($In^{+3}$), tungsten ($W^{+2}$ and $W^{+4}$), osmium ($Os^{+2}$, $Os^{+3}$ and $Os^{+4}$), iridium ($Ir^{+2}$, $Ir^{+3}$ and $Ir^{+4}$), mercury ($Hg^{+2}$), and bismuth ($Bi^{+3}$); and rare earth lanthanides, such as lanthanum ($La^{+3}$), and gadolinium ($Gd^{+3}$). It is contemplated that cations in all of their ordinary valence states will be suitable for forming aggregates and cross-linked lipids. Preferred cations include calcium ($Ca^{+2}$), magnesium ($Mg^{+2}$), and zinc ($Zn^{+2}$) and paramagnetic cations such as manganese (preferably $Mn^{+2}$) and gadolinium ($Gd^{+3}$). Particularly preferred is calcium ($Ca^{+2}$). As will be apparent to one skilled in the art, some of the above ions (notably lead and nickel) may have associated toxicity and thus may be inappropriate for in vivo use.

When the charged lipid is cationic, an anionic material, for example, may be used to form aggregates. Preferably, the anionic material is multivalent, such as, for example, divalent. Examples of useful anionic materials include monatomic and polyatomic anions such as carboxylate ions, sulfide ion, sulfite ions, sulfate ions, oxide ions, nitride ions, carbonate ions, and phosphate ions. Anions of ethylene diamine tetraacetic acid (EDTA), diethylene triamine pentaacetic acid (DTPA), and 1,4,7,10-tetraazocyclododecane-N', N', N", N"-tetraacetic acid (DOTA) may also be used. Further examples of useful anionic materials include anions of polymers and copolymers of acrylic acid, methacrylic acid, other polyacrylates and methacrylates, polymers with pendant $SO_3H$ groups, such as sulfonated polystyrene, and polystyrenes containing carboxylic acid groups.

Examples of cationic lipids include those listed hereinabove. A preferred cationic lipid for formation of aggregates is N-[1-(2,3-dioleoyloxy)propyl]-N,N,N-trimethyl-ammonium chloride ("DOTMA"). Synthetic cationic lipids may also be used. These include common natural lipids derivatized to contain one or more basic functional groups. Examples of lipids which can be so modified include dimethyldioctadecylammonium bromide, sphingolipids, sphingomyelin, lysolipids, glycolipids such as ganglioside GM1, sulfatides, glycosphingolipids, cholesterol and cholesterol esters and salts, N-succinyldioleoyl-phosphatidylethanolamine, 1,2,-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine and palmitoylhomocystiene.

Specially synthesized cationic lipids also function in the embodiments of the invention. Among these are those disclosed in pending U.S. patent application Ser. No. 08/391,938, filed Feb. 21, 1995, the disclosure of which is hereby incorporated herein by reference in its entirety, and include, for example, N,N'-bis(dodecyaminocarbonyl-methylene)-N, N'-bis(β-N,N,N-trimethylammoniumethylami-nocarbonylmethylene-ethylene-diamine tetraiodide; N,N"-bis hexadecylaminocarbonylmethylene)-N,N',N"-tris(β-N, N,N-trimethylammoniumethylaminocarbonylmethylenedi-ethylenetriamine hexaiodide; N,N'-Bis(dodecylaminocarbo-nylmethylene)-N,N"-bis(β-N,N,N-trimethylammonium-ethyl-aminocarbonylmethylene)cyclohexylene-1,4-diamine tetraiodide; 1,1,7,7-tetra-(β-N,N,N,N-tetramethylammoniu-methylaminocarbonylmethylene)-3-hexadecylaminocarbo-nyl-methylene-1,3,7-triaazaheptane heptaiodide; and N,N, N'N'-tetraphosphoethanolamino-carbonylmethylene) diethylenetriamine tetraiodide.

In the case of stabilizing materials which contain both cationic and non-cationic lipids, a wide variety of lipids, as described above, may be employed as the non-cationic lipid. Preferably, the non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates, and alkyl phosphi-tes, may also be used in the stabilizing materials. One of skill in the art will recognize, in view of the present disclosure, that other natural and synthetic variants carrying positive charged moieties will also function in the invention.

Saturated and unsaturated fatty acids which may be employed in the present stabilizing materials include molecules that preferably contain from about 12 carbon atoms to about 22 carbon atoms, in linear or branched form. Hydrocarbon groups consisting of isoprenoid units and/or prenyl groups can be used. Examples of suitable saturated fatty acids include, for example, lauric, myristic, palmitic, and stearic acids. Examples of suitable unsaturated fatty acids include, for example, lauroleic, physeteric, myristoleic, palmitoleic, petroselinic, and oleic acids. Examples of suitable branched fatty acids include, for example, isolauric, isomyristic, isopalmitic, and isostearic acids.

Other useful lipids or combinations thereof apparent to one skilled in the art which are in keeping with the spirit of the present invention are also encompassed by the present invention. For example, carbohydrate-bearing lipids may be employed, as described in U.S. Pat. No. 4,310,505, the disclosure of which is hereby incorporated herein by reference in its entirety.

In addition to stabilizing materials and/or vesicles formulated from lipids, embodiments of the present invention may involve stabilizing materials or vesicles formulated, in whole or in part, from proteins or derivatives thereof. Suitable proteins for use in the present invention include, for example, albumin, hemoglobin, α-1-antitrypsin, α-fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, myoglobin, immunoglobulins, lactate dehydrogenase, lipase, lipoproteins, acid phosphatase, alkaline phosphatase, α-1-serum protein fraction, α-2-serum protein fraction, β-protein fraction, γ-protein fraction and γ-glutamyl transferase. Other stabilizing materials and vesicles formulated from proteins that may be used in the present invention are described, for example, in U.S. Pat. Nos. 4,572,203, 4,718,433, 4,774,958, and 4,957,656, the disclosures of which are hereby incorporated herein by reference in their entirety. Other protein-based stabilizing materials and vesicles, in addition to those described above and in the aforementioned patents, would be apparent to one of ordinary skill in the art, in view of the present disclosure.

In addition to stabilizing materials and/or vesicles formulated from lipids and/or proteins, embodiments of the present invention may also involve stabilizing materials or vesicles formulated from polymers which may be of natural, semi-synthetic (modified natural) or synthetic origin. Polymer denotes a compound comprised of two or more repeating monomeric units, and preferably 10 or more repeating monomeric units. Semi-synthetic polymer (or modified natural polymer) denotes a natural polymer that has been chemically modified in some fashion. Examples of suitable natural polymers include naturally occurring polysaccharides, such as, for example, arabinans, fructans, fucans, galactans, galacturonans, glucans, mannans, xylans (such as, for example, inulin), levan, fucoidan, carrageenan, galato-carolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyphosphazenes, polyethylenes (such as, for example, polyethylene glycol (including, for example, the class of compounds referred to as PLURONICS®, commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Preferred are synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkyl-acrylates, siloxane, dimethylsiloxane, ethylene oxide, ethylene glycol, hydroxyalkylmethacrylates, N-substituted acrylamides, N-substituted methacryl-amides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethyl-methacrylate, vinyl pyridine, aminoethyl methacrylates, 2-methacryloyloxytrimethyl-ammonium chloride, and polyvinylidene, as well polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenylisocyanate), including combinations thereof. Preferable polymers include polyacrylic acid, polyethylene-imine, polymethacrylic acid, polymethylmethacrylate, polysiloxane, polydimethylsiloxane, polylactic acid, poly($\epsilon$-caprolactone), epoxy resin, poly(ethylene oxide), poly(ethylene glycol), and polyamide (nylon) polymers. Preferable copolymers include the following: polyvinylidene-polyacrylonitrile, polyvinylidene-polyacrylonitrile-polymethylmethacrylate, polystyrene-polyacrylonitrile and poly d-1, lactide co-glycolide polymers. A preferred copolymer is polyvinylidene-polyacrylonitrile. Other suitable monomers and polymers will be apparent to one skilled in the art in view of the present disclosure.

Stabilizing materials and vesicles may be prepared from other materials. For example, materials for preparing the vesicles may be basic and fundamental, and may form the primary basis for creating or establishing the stabilized materials, such as gas and gaseous precursor filled vesicles. Surfactants and fluorosurfactants may be basic and fundamental materials for preparing stabilizing materials and vesicles. On the other hand, the materials may be auxiliary, and act as subsidiary or supplementary agents which may enhance the functioning of the basic stabilizing material(s), or contribute some desired property in addition to that afforded by the basic stabilizing material(s).

It is not always possible to determine whether a given material is a basic or an auxiliary agent, since the functioning of the material is determined empirically, for example, by the results produced with respect to producing stabilized materials or vesicles. As an example of how the basic and auxiliary materials may function, it has been observed that the simple combination of a lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may also be undesirable where the undissolved particulate matter has a diameter of greater than about 7 µm, and especially greater than about 10 µm. Manufacturing steps, such as sterile filtration, may also be problematic with solutions which contain undissolved particulate matter. Thus, propylene glycol may be added to remove this cloudiness by facilitating dispersion or dissolution of the lipid particles. Propylene glycol may also function as a wetting agent which can improve vesicle formation and stabilization by increasing the surface tension on the vesicle membrane or skin. It is possible that propylene glycol can also function as an additional layer that may coat the membrane or skin of the vesicle, thus providing additional stabilization. The conventional surfactants described by D'Arrigo, U.S. Pat. Nos. 4,684,479 and 5,215,680, the disclosures of each of which are hereby incorporated by reference herein in their entirety, may be used as basic or auxiliary stabilizing materials in the present invention.

Additional auxiliary and basic stabilizing materials include, for example, soybean oil, peanut oil, canola oil, olive oil, safflower oil, corn oil, or any other oil commonly known to be ingestible which is suitable for use as a stabilizing compound in accordance with the teachings herein. Any of the oils described herein may be partially fluorinated. Other auxiliary and basic stabilizing materials are disclosed, for example, in U.S. application Ser. No. 08/444,754, filed May 15, 1995, the disclosure of which is hereby incorporated herein by reference in its entirety.

Compounds used to make mixed micelle systems may be used as basic or auxiliary stabilizing materials, and include, for example, lauryltrimethylammonium bromide (dodecyl-), cetyltrimethylammonium bromide (hexadecyl-), myristyltrimethylammonium bromide (tetradecyl-), alkyldimethylbenzylammonium chloride (where alkyl is $C_{12}$, $C_{14}$ or $C_{16}$,), benzyldimethyldodecylammonium bromide/chloride, benzyldimethyl hexadecyl-ammonium bromide/chloride, benzyldimethyl tetradecylammonium bromide/chloride, cetyldimethylethylammonium bromide/chloride, or cetylpyridinium bromide/chloride.

It may be possible to enhance the stability of stabilizing materials or vesicles by incorporating in the stabilizing materials and/or vesicles at least a minor amount, for example, about 1 to about 10 mole percent, based on the total amount of lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which are proximate thereto. In this way, the vesicles may be less prone to come into touching proximity with each other, which may lead to a rupture of the membrane or skin of the respective vesicles and consolidation of the contacting vesicles into a single, larger vesicle. A continuation of this process of consolidation will, of course, lead to significant degradation of the vesicles. The lipids used, especially in connection with vesicles, are preferably flexible. This means, in the context of the present invention, that the vesicles can alter their shape, for example, to pass through an opening having a diameter that is smaller than the diameter of the vesicle.

In certain embodiments, the stabilizing materials or vesicles may comprise, in whole or in part, a fluorinated (including perfluorinated) compound. Suitable fluorinated compounds include, for example, fluorinated surfactants, including alkyl surfactants and amphiphilic compounds. A wide variety of such compounds may be employed, including, for example, the class of compounds which are commercially available as ZONYL® fluorosurfactants (the DuPont Company, Wilmington, Del.), including the ZONYL® phosphate salts (e.g., $[F(CF_2CF_2)_{3-8}CH_2CH_2O]_{1,2}P(O)(O^-NH_4^+)_{2,1}$), which have terminal phosphate groups and ZONYL® sulfate salts, which have terminal sulfate groups (e.g., $F(CF_2CF_2)_{3-8}CH_2CH_2SCH_2CH_2N^+(CH_3)_3{}^-OSO_2OCH_3$). Suitable ZONYL® surfactants also include, for example, ZONYL® surfactants identified as Telomer B, including Telomer B surfactants which are pegylated (i.e., which have at least one polyethylene glycol group attached thereto), also known as PEG-Telomer B, available from the DuPont Company. Other suitable perfluorinated surfactants are the partially fluorinated phosphocholine surfactants. In these fluorinated surfactants, the dual alkyl compounds may be fluorinated at the terminal alkyl chains and the proximal carbons may be hydrogenated. These fluorinated phosphocholine surfactants may be used for making the stabilizing materials and/or vesicles of the present invention. Other suitable fluorosurfactants are described in U.S. Pat. Nos. 5,276,146, 5,344,930, and 5,562, 893, and U.S. application Ser. No. 08/465,868, filed Jun. 6, 1995, the disclosures of each of which are hereby incorporated by reference herein in their entirety.

In addition, it may be desirable to use a fluorinated compound, especially a perfluorocarbon compound, which may be in the liquid state at the temperature of use, including, for example, the in vivo temperature of the human body, to assist or enhance the stability of the lipid and/or vesicle compositions, and especially, gas filled vesicles. Suitable liquid perfluorocarbons which may be used include, for example, perfluorohexane, perfluoroheptane, perfluorooctane, perfluorononane, perfluorodecalin, perfluorododecalin, perfluorooctyliodide, perfluorooctylbromide, perfluorotripropylamine, and perfluorotributylamine. In general, perfluorocarbons comprising about six or more carbon atoms will be liquid at normal human body temperature. Among these perfluorocarbons, perfluorooctylbromide and perfluorohexane, which are liquids at room temperature, are preferred. The gas which is present may be, for example, nitrogen or perfluoropropane, or may be a gaseous precursor that has been converted to a gas, which may also be a perfluorocarbon, for example, perfluoropentane. In the latter case, the lipid stabilizing materials and/or vesicle compositions may be prepared from a mixture of perfluorocarbons, which for the examples given, would be perfluoropropane (gas) or perfluoropentane (which can be a gaseous precursor that is converted to a gas, by temperature or pressure, prior to administration to a patient) and perfluorooctylbromide (liquid). Although not intending to be bound by any theory of operation, it is believed that, in the case of vesicle compositions, the liquid fluorinated compound may be situated at the interface between the gas and the membrane or wall surface of the vesicle. There may be thus formed a further stabilizing layer of liquid fluorinated compound on the internal surface of the stabilizing compound, for example, a lipid used to form the vesicle, and this perfluorocarbon layer may also prevent the gas from diffusing through the vesicle membrane.

Other suitable fluorinated compounds for use as the stabilizing materials and/or vesicles of the present invention are described in U.S. Pat. No. 5,562,893, the disclosure of which is hereby incorporated herein by reference in its entirety. For example, synthetic organic monomeric repeating units may be used to form polymers suitable as stabilizing materials in the present invention, including hydroxyacids, lactones, lactides, glycolides, acryl containing compounds, aminotriazol, orthoesters, anyhdrides, ester imides, imides, acetals, urethanes, vinyl alcohols, enolketones, and organosiloxanes.

The method of introducing fluorine into any of these materials is known in the art. For example, the introduction of perfluoro-t-butyl moieties is described in U.S. Pat. No. 5,234,680, the disclosure of which is hereby incorporated by reference herein in its entirety. These methods generally involve the reaction of perfluoroalkyl carbanions with host molecules as follows: $(CF_3)_3C^- + R—X \rightarrow (CF_3)_3C—R$, where R is a host molecule and X is a good leaving group, such as bromine, chlorine, iodine or a sulfonato group. After adding a leaving group to the foregoing stabilizing material using methods known in the art, perfluoro-t-butyl moieties can then be easily introduced to these derivatized stabilizing materials as described above. Additional methods are known for the introduction of trifluoromethyl groups into various organic compounds are known in the art. For example, trifluoromethyl groups may be introduced by nucleophilic pertluoroalkylation using perfluoroalkyl-trialkylsilanes.

Fluorine can be introduced into any of the aforementioned stabilizing materials or vesicles either in their monomeric or polymeric form. Preferably, fluorine moieties are introduced into monomers, such as fatty acids, amino acids or polymerizable synthetic organic compounds, which are then polymerized for subsequent use as stabilizing materials and/or vesicles. The introduction of fluorine into stabilizing materials and/or vesicles may also be accomplished by forming vesicles in the presence of a perfluorocarbon gas. For example, when vesicles are formed from proteins, such as human serum albumin in the presence of a perfluorocarbon gas, such as perfluoropropane, using mechanical cavitation, fluorine from the gas phase becomes bound to the protein vesicles during formation. The presence of fluorine in the vesicles and/or stabilizing materials can be detected by NMR of vesicle debris which has been purified from disrupted vesicles. Fluorine can also be introduced into stabilizing materials and/or vesicles using other methods, such as sonication, spray-drying or emulsification techniques.

Another way in which fluorine can be introduced into the stabilizing materials is by using a fluorine-containing reactive compound. The term "reactive compound" refers to compounds which are capable of interacting with the stabilizing material and/or vesicle in such a manner that fluorine moieties become covalently attached to the stabilizing material and/or vesicle. When the stabilizing material is a protein, preferred reactive compounds are either alkyl esters or acyl halides which are capable of reacting with the protein's amino groups to form an amide linkage via an acylation reaction. The reactive compound can be introduced at any stage during vesicle formation, but is preferably added to the gas phase prior to vesicle formation. For example, when vesicles are to be made using mechanical or ultrasound cavitation techniques, the reactive compound can be added to the gas phase by bubbling the gas to be used in the formation of the vesicles (starting gas) through a solution of the reactive compound into the gas phase. The resultant gas mixture, which now contains the starting gas and the reactive compound, is then used to form vesicles. The vesicles are preferably formed by sonication of human serum albumin in the presence of a gas mixture, as described in U.S. Pat. No. 4,957,656, the disclosure of which is hereby incorporated herein by reference in its entirety.

Suitable fluorine containing alkyl esters and acyl halides for use as stabilizing materials and/or vesicle forming materials in the present invention include, for example, diethyl hexafluoroglutarate, diethyl tetrafluorosuccinate, methyl heptafluorobutyrate, ethyl heptafluorobutyrate, ethyl pentafluoropropionate, methyl pentafluoropropionate, ethyl perfluorooctanoate, methyl perfluorooctanoate, nonafluoropentanoyl chloride, perfluoropropionyl chloride, hexafluoroglutaryl chloride and heptafluorobutyryl chloride.

Other fluorine containing reactive compounds can also be synthesized and used as the stabilizing materials and/or vesicle forming materials in the present invention, including, for example, aldehydes, isocyanates, isothiocyanates, epoxides, sulfonyl halides, anhydrides, acid halides and alkyl sulfonates, which contain perfluorocarbon moieties, including $—CF_3$, $—C_2F_5$, $—C_3F_4$ and $—C(CF_3)_3$. These reactive compounds can be used to introduce fluorine moieties into any of the aforementioned stabilizing materials by choosing a combination which is appropriate to achieve covalent attachment of the fluorine moiety.

Sufficient fluorine should be introduced to decrease the permeability of the vesicle to the aqueous environment. This will result in a slower rate of gas exchange with the aqueous environment which is evidenced by enhanced pressure resistance. Although the specific amount of fluorine necessary to stabilize the vesicle will depend on the components of the vesicle and the gas contained therein, after introduction of fluorine the vesicle will preferably contain 0.01 to 20% by weight, and more preferably about 1 to 10% by weight fluorine.

The stability of vesicles may be attributable, at least in part, to the materials from which the vesicles are made, including, for example, the lipids, polymers, proteins and/or surfactants described above, and it is often not necessary to employ additional stabilizing materials, although it is optional and may be preferred to do so. In addition to, or instead of, the lipid, protein, polymer and/or surfactant compounds discussed above, the compositions described herein may comprise one or more other stabilizing materials. Exemplary stabilizing materials include, for example, surfactants, fluorosurfactants and polymers, in addition to those discussed above. The stabilizing materials may be employed to desirably assist in the formation of vesicles and/or to assure substantial encapsulation of the gases and/or gaseous precursors. Even for relatively insoluble, non-diffusible gases, such as perfluoropropane or sulfur hexafluoride, improved vesicle compositions may be obtained when one or more stabilizing materials are utilized in the formation of the gas and/or gaseous precursor filled vesicles. These compounds may help improve the stability and the integrity of the vesicles with regard to their size, shape and/or other attributes. Suitable surfactants and fluorosurfactants for use as stabilizing materials in the present invention include the surfactants and fluorosurfactants described in detail above.

Like the polymers discussed above, other polymers useful as stabilizing materials for preparing the gas and/or gaseous precursor filled vesicles may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, polyethylenes (such as, for example, polyethylene glycol (including the class of compounds referred to as PLURONICS®, commercially available from BASF, Parsippany, N.J.), polyoxyethylene, and polyethylene terephthlate), polypropylenes (such as, for example, polypropylene glycol), polyurethanes (such as, for example. polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of vesicles which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated herein by reference in its entirety.

Particularly preferred embodiments of the present invention involve stabilizing) materials and/or vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinylalcohol, and polyvinylpyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanolamine-polyethylene glycol 5000 (DSPE-PEG5000).

In certain preferred embodiments of the present invention, the lipid compositions may include about 77.5 mol % DPPC, 12.5 mol % of DPPA. and 10 mol % of DPPE-PEG5000. Also preferred are compositions which comprise about 80 to about 90 mol % DPPC, about 5 to about 15 mol % DPPA and about 5 to about 15 mol % DPPE-PEG5000. Especially preferred are compositions which comprise DPPC, DPPA and DPPE-PEG5000 in a mole % ratio of 82:10:8, respectively. DPPC is substantially neutral. since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media.

The terms "stable" or "stabilized" mean that the vesicles may be substantially resistant to degradation, including, for example, loss of vesicle structure or encapsulated gas and/or gaseous precursor, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and/or gaseous precursor filled vesicles, may also be stable even under adverse conditions, such as temperatures and pressures which are above or below those experienced under normal ambient conditions.

The gas and/or gaseous precursor filled vesicles used in the present invention may be controlled according to size, solubility and heat stability by choosing from among the various additional or auxiliary stabilizing materials described herein. These materials can affect the parameters of the vesicles, especially vesicles formulated from lipids, not only by their physical interaction with the membranes, but also by their ability to modify the viscosity and surface tension of the surface of the gas and/or gaseous precursor filled vesicle. Accordingly, the gas and/or gaseous precursor filled vesicles used in the present invention may be favorably modified and further stabilized, for example, by the addition of one or more of a wide variety of (i) viscosity modifiers, including, for example, carbohydrates and their phosphorylated and sulfonated derivatives: polyethers, preferably with molecular weight ranges between 400 and 100,000; and di- and trihydroxy alkanes and their polymers, preferably with molecular weight ranges between 200 and 50,000; (ii) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, poloxamer 181. PLURONICS® (BASF, Parsippany, N.J.), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (iii) suspending and/or viscosity-increasing agents, including, for example, acacia, agar, alginic acid, aluminum mono-stearate, bentonite, magma, carbomer 934P, carboxymethyl-cellulose, calcium and sodium and sodium 12, carrageenan, cellulose, dextran, gelatin, guar gum, locust bean gum, veegum, hydroxyethyl cellulose, hydroxypropyl methyl-cellulose, magnesium-aluminum-silicate, ZEOLITES®, methylcellulose, pectin, polyethylene oxide, povidone, propylene glycol alginate, silicon dioxide, sodium alginate, tragacanth, xanthan gum, α-d-gluconolactone, glycerol and mannitol; (iv) synthetic suspending agents, such as polyethylene glycol (PEG), polyvinylpyrrolidone (PVP), polyvinylalcohol (PVA), polypropylene glycol (PPG), and polysorbate; and (v) tonicity raising agents which stabilize and add tonicity, including, for example, sorbitol, mannitol, trehalose, sucrose, propylene glycol and glycerol.

The present lipid and/or vesicles are desirably formulated in an aqueous environment/carrier which can induce the lipid, because of its hydrophobic-hydrophilic nature, to form vesicles, which may be the most stable configuration which can be achieved in such an environment. The diluents which can be employed to create such an aqueous environment/carrier include, for example, water, including deionized water, normal saline, physiological saline or water containing one or more dissolved solutes, such as salts or sugars, which do not substantially interfere with the formation and/or stability of the vesicles or their use as blood substitutes.

A wide variety of materials can be used as fluorinated gases and/or fluorinated gaseous precursors for incorporating in or entrapping within stabilizing materials and vesicles. As described herein, the fluorinated gaseous precursors can be converted to a gas, by temperature or pressure, prior to administration to a patient. Exemplary fluorinated gases and fluorinated gaseous precursors for use in the present invention include, for example, hexafluoroacetone, 1,3-dichlorotetrafluoroacetone, tetrafluoroallene, boron trifluoride, 1,2,3-trichloro-2-fluoro-1,3-butadiene, hexafluoro-1,3-butadiene, 1-fluorobutane, perfluorobutane, decafluorobutane, perfluoro-1-butene, perfluoro-2-butene, 2-chloro-1,1,1,4,4,4-hexafluorobutyne, 2-chloro-1,1,1,4,4,4-hexafluoro-2-butene, perfluoro-2-butyne, octafluorocyclobutane, perfluorocyclobutene, perfluorocyclobutane, perfluorocyclopentane, octafluorocyclopentene, perfluorocyclopropane, 1,1,1-trifluorodiazoethane, hexafluorodimethylamine, perfluoroethane, perfluoropropane, perfluoropentane, hexafluoroethane, hexafluoropropylene, 1,1,2,2,3,3,4,4-octafluorobutane, 1,1,1,3,3-pentafluorobutane, octafluoropropane, octafluorocyclopentane, 1,1-dichlorofluoroethane, hexafluoro-2-butyne, octafluoro-2-butene, hexafluorobuta-1,3-diene, perfluorodimethylamine, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1,1-trichloro-2,2,2-trifluoroethane, 1,1-dichloro-1,2-difluoroethylene, 1,1-dichloro-1,2,2,2-tetrafluoroethane, 1-chloro-1,1,2,2,2-pentafluoroethane, 1,1-difluoro-2-chloroethane, 1,1-dichloro-2-fluoroethane, dichloro-1,1,2,2-tetrafluoroethane, 1-chloro-1,1,2,2-tetrafluoroethane, 2-chloro-1,1-difluoroethane, 1,1,2-trifluoro-2-chloroethane, 1,2-difluorochloroethane, chloropentafluoroethane, dichlorotrifluoroethane, fluoroethane, nitropentafluoroethane, nitrosopentafluoroethane, perfluoroethylamine, 1,2-dichloro-2,2-difluoroethane, 1,1-dichloro-1,2-difluoroethane, 1,2-dichloro-1,1,3-trifluoropropane, 1,2-difluoroethane, 1,2-difluoroethylene, trifluoromethanesulfonylchloride, trifluoromethanesulfenylchloride, (pentafluorothio)trifluoromethane, trifluoromethanesulfonylfluoride, bromodifluoronitrosomethane, bromofluoromethane, bromochlorodifluoromethane, bromochlorofluoromethane, bromotrifluoromethane, bromotrifluoroethane, chlorodifluoronitromethane, chlorofluoromethane, chlorotrifluoromethane, chlorodifluoromethane, dibromofluoromethane, dibromodifluoromethane, dichlorodifluoromethane, dichlorofluoromethane, 1-bromoperfluorobutane, difluoromethane, difluoroiodomethane, fluoromethane, perfluoromethane, iodotrifluoromethane, iodotrifluoroethylene, nitrotrifluoromethane, nitrosotrifluoromethane, tetrafluoromethane, trichlorofluoromethane, trifluoromethane, perfluoropent-1-ene, 1,1,1,2,2,3-hexafluoropropane, heptafluoropropane, 1,1,1,2,3,3,3-heptafluoropropane, 1,1,2,2,3,3-heptafluoropropane, 2,2-difluoropropane, heptafluoro-1-nitropropane, heptafluoro-1-nitrosopropane, heptafluoro-2-iodopropane, perfluoropropane, hexafluoropropane, 1,1,1,2,3,3-hexafluoro-2,3-dichloropropane, 1-bromo-1,1,2,3,3,3-hexafluoropropane, 1-bromoperfluoropropane, 2-chloropentafluoro-1,3-butadiene, 3-fluoropropane, 3-fluoropropylene, perfluoropropylene, perfluorotetrahydropyran, perfluoromethyltetrahydrofuran, perfluorobutylmethyl ether, perfluoromethyl-n-butyl ether, perfluoromethylisopropyl ether, perfluoromethyl-t-butyl ether, perfluorobutyl ethyl ether, perfluoromethylpentyl ether, 3,3,3-trifluoropropyne, 3-fluorostyrene, sulfur (di)-decafluoride ($S_2F_{10}$), sulfur hexafluoride, selenium hexafluoride, trifluoroacetonitrile, trifluoromethyl peroxide. trifluoromethyl sulfide, tungsten hexafluoride, 1-bromo-nonafluorobutane, 1-chloro-1-fluoro-1-bromomethane, 1-bromo-2,4-difluorobenzene, 2-iodo-1,1,1-trifluoroethane, bromine pentafluoride, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)-acetophenone, bis(perfluoroisopropyl) ether, bis(perfluoropropyl) ether, perfluoro isobutyl methyl ether, perfluoro n-propyl ethyl ether, perfluoro cyclobutyl methyl ether, perfluoro cyclopropyl ethyl ether, perfluoro isopropyl methyl ether, perfluoro n-propyl methyl ether, perfluorodiethyl ether, perfluoro cyclopropyl methyl ether, perfluoro methyl ethyl ether, perfluoro dimethyl ether and mixtures thereof.

Examples of various fluorinated compounds and their boiling points are set forth in the table below.

TABLE 1

| Compound | Boiling Point (° C.) |
| --- | --- |
| bromotrifluoroethane | −57.8 |
| chlorotrifluoromethane | −81.5 |
| dichlorodifluoromethane | −29.8 |
| dibromofluoromethane | 23 |
| chloropentafluoroethane | −38.7 |
| bromochlorodifluoromethane | −4 |
| dichloro-1,1,2,2-tetrafluoroethane | 3.1–3.6 |
| octafluorocyclobutane | −5.8 |
| decafluorobutane | −2 |
| hexafluoroethane | −78.1 |
| perfluoromethane | −129 |
| perfluoroethane | −78.3 |
| perfluoropropane | −36 |
| perfluorobutane | −2 |
| perfluoropropylene | −28 |
| perfluorocyclobutane | −6 |
| perfluoro-2-butyne | −25 |
| perfluoro-2-butene | 1.2 |
| perfluorobuta-1,3-diene | 6 |
| perfluoro n-propyl ethyl ether | 23.3 |
| perflouro diethyl ether | 3–4.5 |
| perfluoro methyl ethyl ether | −23 |
| perfluoro dimethyl ether | −59 |
| sulfur hexafluoride | m.p. −50.5, sublimes −63.8 |
| selenium hexafluoride | m.p. −34.6, sublimes −46.6 |
| perfluoropropionyl chloride | 8 |
| 1-bromo-1,1,2,3,3,3-hexafluoropropane | 35.5 |
| bromoperfluoropropane | 35.5 |
| 2-chloro-1,1,1,4,4,4-hexafluoro-2-butene | 33 |
| 2-chloropentafluoro-1,3-butadiene | 37 |
| iodotrifluoroethylene | 30 |
| 1,1,2-trifluoro-2-chloroethane | 30 |
| 1,2-difluorochloroethane | 35.5 |
| 1,1-difluoro-2-chloroethane | 35.1 |
| 1,1-dichlorofluoroethane | 31.8 |
| 1-bromoethane | 37 |
| 1-fluorobutane | 32.5 |

TABLE 1-continued

| Compound | Boiling Point (° C.) |
| --- | --- |
| perfluoropentane | 29.5 |
| perfluorotetrahydropyran | 34 |
| perfluoromethyltetrahydrofuran | 27 |
| perfluoro t-butyl methyl ether | 36 |
| perfluoro n-butyl methyl ether | 35.4 |
| perfluoro isopropyl methyl ether | 36 |
| 1-bromo-nonafluorobutane | 43 |
| perfluorooctyliodide | 160–161 |
| perfluoroocytlbromide | 142 |
| 1-chloro-1-fluoro-1-bromomethane | 38 |
| 1,1,1-trichloro-2,2,2-trifluoroethane | 45.7 |
| 1,2-dichloro-2,2-difluoroethane | 46 |
| 1,1-dichloro-1,2-difluoroethane | 45 |
| 1,2-dichloro-1,1,3-trifluoropropane | 50.4 |
| 1-bromoperfluorobutane | 43 |
| 1-bromo-2,4-difluorobenzene | 44 |
| 2-iodo-1,1,1-trifluoroethane | 53 |
| 5-bromovaleryl chloride | 43 |
| 1,3-dichlorotetrafluoroacetone | 43 |
| bromine pentafluoride | 40.3 |
| heptafluoro-2-iodopropane | 39 |
| 6-bromo-1-hexene | 47 |
| 2-bromo-2-nitropropane | 45 |
| 2-bromo-5-nitrothiophene | 45 |
| 2-bromopropene | 47 |
| 3-chloro-5,5-dimethyl-2-cyclohexene | 44 |
| 2-chloro-2-methylpropane | 50 |
| perfluoro-2-methyl-2-pentene | 51 |
| 1,1,1,3,3-pentafluoropentane | 40 |
| perfluorotributylamine | 178 |
| perfluorotripropylamine | 130 |
| 3-fluorobenzaldehyde | 56 |
| 2-fluoro-5-nitrotoluene | 53 |
| 3-fluorostyrene | 40 |
| 3,5-difluoroaniline | 40 |
| 2,2,2-trifluoroethylacrylate | 45 |
| 3-(trifluoromethoxy)-acetophenone | 49 |
| 1,1,2,2,3,3,4,4-octafluorobutane | 44.8 |
| 1,1,1,3,3-pentafluoropropane | 40 |
| perfluoro-4-methylquinolizidine | 149 |
| perfluoro-N-methyl-decahydroquinone | 150–155 |
| perfluoro-N-methyl-decahydroisoquinone | 150–155 |
| perfluoro-N-cyclohexyl-pyrrolidine | 145–152 |
| tetradecaperfluoroheptane | 76 |
| dodecaperfluorocyclohexane | 52 |
| n-perfluorohexane | 59–60 |
| perfluoroheptane | 81 |
| perfluorooctane | 102 |
| perfluorononane | 125 |
| perfluorodecane | ~143 |
| perfluorododecane | m.p. 75–77 |
| perfluoro-2-methyl-2-pentene | 51 |
| perfluorocyclohexane | 52 |
| perfluorodecalin | 142 |
| perfluorobutylethyl ether | 60 |
| bis(perfluoroisopropyl) ether | 54 |
| bis(perfluoropropyl) ether | 59 |

Preferred gases and gaseous precursors are compounds which are sparingly soluble in water but which may, in some cases, be liposoluble, such as low molecular weight alkanes and their fluorinated analogs. Preferred gases and gaseous precursors include, for example, perfluorocarbons, perfluoroethers, and sulfur hexafluoride. Preferred perfluorocarbons may have from 1 to about 4 carbon atoms and from 4 to about 10 fluorine atoms. Preferred perfluoroethers have from 1 to about 4 carbon atoms, from 4 to about 10 fluorine atoms, and 1 to about 2 oxygen atoms, preferably 1 oxygen atom. Preferred gases and gaseous precursors for use in the present invention include perfluoromethane, perfluoroethane, perfluoropropane, perfluorobutane, perfluorocyclobutane, bromoperfluoropropane, perfluoropentane, perfluorocylcopentane, perfluorohexane, perfluoroheptane, perfluorooctane, perfluorononane, perfluorodecane, perfluoromethylbutyl ether ($CF_2$—O—$CF_2CF_2CF_3$), perfluoromethyl-n-butyl ether, perfluoromethylisopropyl ether, perfluoromethyl-t-butyl ether, perfluorotetrahydropyran, perfluoromethyltetrahydrofuran, ($CF_3CF_2$—O—$CF_2CF_3$), perfluoromethylpentyl ether and other perfluoroether analogues containing between 4 and 6 carbon atoms, and optionally containing one halide ion, preferably $Br^{-1}$. For example, compounds having the structure $C_nF_yH_xOBr$, where n is an integer of from 1 to about 6, y is an integer of from 0 to about 13, and x is an integer of from 0 to about 13, are useful as gaseous precursors. Suitable gaseous precursors having this formula include perfluoropropyloxylbromide and 2-bromooxyperfluoropropane.

A fluorinated gaseous precursor and/or fluorinated liquid may be used in conjunction with the fluorinated gas of the present invention for administration to the patient. Whether the fluorinated compound is used as a liquid or a gas generally depends on its liquid/gas phase transition temperature, or boiling point. As known to one skilled in the art, the effective boiling point of a substance may be related to the pressure or temperature to which that substance is exposed. This relationship is exemplified by the ideal gas law: $PV=nRT$, where P is pressure, V is volume, n is moles of substance, R is the gas constant, and T is temperature. The ideal gas law indicates that as pressure increases, the effective boiling point increases also. Conversely, as pressure decreases, the effective boiling point decreases. When considering the $PV=nRT$ equation, one skilled in the art will recognize that physiological pressures, especially inside arteries, may increase normal boiling points as much as about 5° C.

Preferably, the fluorinated gas used in the present invention is bromotrifluoroethane, chlorotrifluoromethane, dichlorodifluoromethane, dibromofluoromethane, chloropentafluoroethane, bromochlorodifluoromethane, dichloro-1,1,2,2-tetrafluoroethane, octafluorocyclobutane, decafluorobutane, hexafluoroethane, perfluoromethane, perfluoroethane, perfluoropropane, perfluorobutane, perfluoropropylene, perfluorocyclobutane, perfluoro-2-butyne, perfluoro-2-butene, perfluorobuta-1,3-diene, perfluoro n-propyl ethyl ether, perflouro diethyl ether, perfluoro methyl ethyl ether, perfluoro dimethyl ether, sulfur hexafluoride, selenium hexafluoride or perfluoropropionyl chloride. More preferably, the fluorinated gas is perfluoromethane, perfluoroethane, perfluoropropane, perfluorobutane, perfluorocyclobutane, perfluoro n-propyl ethyl ether, perflouro diethyl ether, perfluoro methyl ethyl ether, perfluoro dimethyl ether or sulfur hexafluoride. Even more preferably, the fluorinated gas is perfluoromethane, perfluoroethane, perfluoropropane or perfluorobutane. Most preferably, the fluorinated gas is perfluoropropane or perfluorobutane.

Preferably, the gaseous precursor, that has been converted to a gas, by temperature or pressure, prior to administration to a patient, is 1-bromo-1,1,2,3,3,3-hexafluoropropane, bromoperfluoropropane, 2-chloro-1,1,1,4,4,4-hexafluoro-2-butene, 2-chloropentafluoro-1,3-butadiene, iodotrifluoroethylene, 1,1,2-trifluoro-2-chloroethane, 1,2-difluorochloroethane, 1,1-difluoro-2-chloroethane, 1,1-dichlorofluoroethane, 1-bromoethane, 1-fluorobutane, perfluoropentane, perfluorotetrahydropyran, perfluoromethyltetrahydrofuran, perfluoro t-butyl methyl ether, perfluoro n-butyl methyl ether, perfluoro isopropyl methyl ether, 1-bromo-nonafluorobutane, 1-chloro-1-fluoro-1-bromomethane, 1,1,1-trichloro-2,2,2-trifluoroethane, 1,2-dichloro-2,2-difluoroethane, 1,1-dichloro-1,2-difluoroethane, 1,2-dichloro-1,1,3-trifluoropropane, 1-bromoperfluorobutane, 1-bromo-2,4-difluorobenzene, 2-iodo-1,1,1-trifluoroethane, 5-bromovaleryl chloride, 1,3-dichlorotetrafluoroacetone, bromine pentafluoride, heptafluoro-2-iodopropane, 6-bromo-1-hexene, 2-bromo-2-nitropropane, 2-bromo-5-nitrothiophene, 2-bromopropene, 3-chloro-5,5-dimethyl-2-cyclohexane, 2-chloro-2-methylpropane, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)-acetophenone, 1,1,2,2,3,3,4,4-octafluorobutane, 1,1,1,3,3-pentafluorobutane, tetradecaperfluoroheptane, dodecaperfluorocyclohexane, n-perfluorohexane, perfluoro-2-methyl-2-pentene, perfluorocyclohexane, perfluorobutylethyl ether, bis(perfluoroisopropyl) ether and/or bis(perfluoropropyl) ether. More preferably, the fluorinated gaseous precursor, that has been converted to a gas, by temperature or pressure, prior to administration to a patient, is bromoperfluoropropane, perfluoropentane, perfluorocyclopentane, perfluorobutyl methyl ether, perfluoromethyl n-butyl ether, perfluoromethyl isopropyl ether, perfluoromethyl t-butyl ether, perfluorotetrahydropyran and/or perfluoromethyltetrahydrofuran. Most preferably, the fluorinated gaseous precursor that has been converted to a gas is perfluoropentane.

Mixtures of different types of gases, such as mixtures of oxygen, fluorinated gases, gaseous precursors and/or other types of gases, gaseous precursors and/or liquids, can also be used in the present invention. The compositions of the present invention may comprise, for example, air, noble gases, such as helium, rubidium hyperpolarized xenon, hyperpolarized argon, hyperpolarized helium, neon, argon, xenon, carbon dioxide, nitrogen, isopropyl acetylene, allene, 1,2-butadiene, 2,3-butadiene, 1,3-butadiene, 2-methyl-1,3-butadiene, butadiene, 2-methylbutane, 1-butene, 2-butene, 2-methyl-1-butene, 3-methyl-1-butene, 4-phenyl-3-butene-2-one, 2-methyl-1-butene-3-yne, butyl nitrate, 1-butyne, 2-butyne, 3-methyl-1-butyne, 2-bromobutyraldehyde, carbonyl sulfide, crotononitrile, cyclobutane, methylcyclobutane, cyclopropane, 3-chlorocyclo-pentene, dimethylamine, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, dimethylethylamine, bis(dimethylphosphine)amine, dimethyloxonium chloride, 2,3-dimethyl-2-norbornane, 1,3-dioxolane-2-one, 1,1-dichloroethane, 1,1-dichloroethylene, chloroethane, 1,1-dichloroethane, methane, chlorodinitromethane, iodomethane, disilanomethane, 2-methylbutane, methyl ether, methyl isopropyl ether, methyllactate, methylnitrite, methylsulfide, methyl vinyl ether, neon, neopentane, nitrogen, nitrous oxide, 1,2,3-nonadecanetricarboxylic acid 2-hydroxytrimethyl ester, 1-nonene-3-yne, 1,4-pentadiene, n-pentane, 4-amino-4-methylpentan-2-one, 1-pentene, 2-pentene (cis and trans), 3-bromopent-1-ene, 2-chloropropane, tetrachlorophthalic acid, 2,3,6-trimethylpiperidine, propane, 1-chloropropane, 1-chloropropylene, chloropropylene-(trans), chloropropane-(trans), 2-chloropropylene, 2-aminopropane, 1,2-epoxypropane, propene, propyne, 2,4-diaminotoluene, vinyl acetylene, vinyl ether, ethyl vinyl ether, 5-bromovaleryl chloride, 1-bromoethane, 6-bromo-1-hexene, 2-bromo-2-nitropropane, 2-bromo-5-nitrothiophene, 2-bromopropene, 3-chloro-5,5-dimethyl-2-cylohexene, 2-chloro-2-methylpropane and mixtures thereof.

In certain preferred embodiments, the gases, for example, oxygen and a perfluorocarbon gas, may be combined with a fluorinated liquid compound including, but not limited to, perfluorooctyliodide, perfluorooctylbromide, 1,2-dichloro-1,1,3-trifluoropropane, 2-iodo-1,1,1-trifluoroethane, 2-chloro-2-methylpropane, perfluoro-2-methyl-2-pentene, perfluorotributylamine, perfluorotripropylamine, 3-fluorobenzaldehyde, 2-fluoro-5-nitrotoluene, perfluoro-4-methylquinolizidine, perfluoro-N-methyl-decahydroquinone, perfluoro-N-methyl-decahydroisoquinone, perfluoro-N-cyclohexyl-pyrrolidine, tetradecaperfluoroheptane, dodecaperfluorocyclohexane, perfluorohexane, perfluoroheptane, perfluorooctane, perfluorononane, perfluorodecane, perfluorododecane, perfluoro-2-methyl-2-pentene, perfluorocyclohexane, perfluorodecalin, perfluorobutylethyl ether, bis(perfluoroisopropyl) ether and bis(perfluoropropyl) ether. Preferably, the fluorinated liquid compound is perfluorohexane, perfluoroheptane, perfluorooctane, perfluorononane, perfluorodecane, perfluorododecane, perfluorodecalin, perfluorooctyliodide, perfluorooctylbromide, perfluorotributylamine, perfluorotripropylamine, perfluorobutyl ethyl ether, bis(perfluoroisopropyl) ether or bis(perfluoropropyl) ether.

Among the gaseous precursors which are suitable for use in stabilizing materials and compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid ($H_2CO_3$) is an example of a suitable inorganic acid, and aminomalonic acid is an example of a suitable organic acid. Other acids, including inorganic and organic acids, would be readily apparent to one skilled in the art in view of the present disclosure.

Gaseous precursors derived from salts are preferably selected from the group consisting of alkali metal salts, ammonium salts and mixtures thereof. More preferably, the salt is selected from the group consisting of carbonate, bicarbonate, sesquecarbonate, aminomalonate and mixtures thereof. Gaseous precursor materials derived from salts include, for example, lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, 9(3):525–532 (1970); Fitzpatrick et al., *Inorganic Chemistry*, 13(3):568–574 (1974); and Stelmashok et al., *Koordinatsionnaya Khimiya*, 3(4)524–527 (1977). The disclosures of each of these publications are hereby incorporated herein by reference in their entirety.

In addition to, or instead of, being sensitive to changes in pH, the gaseous precursor materials may also comprise compounds which are sensitive to changes in temperature. The gaseous precursor materials may be photoactivated materials, such as a diazonium ion and aminomalonate. As discussed more fully hereinafter, certain stabilizing materials and/or vesicles, particularly vesicles, may be formulated so that gas is formed at the target tissue or by the action of ultrasound on the stabilizing materials. Examples of gaseous precursors are described, for example, in U.S. Pat. Nos. 5,088,499 and 5,149,319, the disclosures of each of which are hereby incorporated herein by reference in their entirety. Other gaseous precursors, in addition to those exemplified above, will be apparent to one skilled in the art in view of the present disclosure.

The gases and/or gaseous precursors are preferably incorporated in the stabilizing materials and/or vesicles irrespective of the physical nature of the composition. Thus, it is contemplated that the gases and/or gaseous precursors may be incorporated, for example, in stabilizing materials in which the stabilizing materials are aggregated randomly, such as emulsions, dispersions or suspensions, as well as in vesicles, including vesicles which are formulated from lipids, such as micelles and liposomes. Incorporation of the gases and/or gaseous precursors in the stabilizing materials and/or vesicles may be achieved by using any of a number of methods. For example, in the case of vesicles based on lipids, the formation of gas filled vesicles can be achieved by shaking or otherwise agitating an aqueous mixture which comprises a gas and/or gaseous precursor and one or more lipids. This promotes the formation of stabilized vesicles within which the gas and/or gaseous precursor is encapsulated.

In addition, a gas may be bubbled directly into an aqueous mixture of stabilizing materials and/or vesicle-forming compounds. Alternatively, a gas instillation method can be used as described, for example, in U.S. Pat. Nos. 5,352,435 and 5,228,446, the disclosures of each of which are hereby incorporated herein by reference in their entirety. Suitable methods for incorporating the gas and/or gaseous precursor in cationic lipid compositions are described also in U.S. Pat. No. 4,865,836, the disclosure of which is hereby incorporated herein by reference in its entirety. Other methods would be apparent to one skilled in the art based on the present disclosure. Preferably, the gas may be instilled in the stabilizing materials and/or vesicles after or during the addition of the stabilizing material and/or during formation of vesicles.

In preferred embodiments, the gases and/or gaseous precursors are incorporated in vesicle compositions, with micelles and liposomes being preferred. Vesicles in which a gas or gaseous precursor that has been converted to a gas or both are encapsulated are advantageous in that they provide improved reflectivity in vivo and improved oxygen delivery capabilities.

It is preferred that the stabilizing materials, and especially the vesicles, be formulated from lipids and optional stabilizing compounds to promote the formation of stable vesicles, as discussed in above. Additionally, it is preferred that the stabilizing materials and/or vesicles comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Accordingly, their use may promote the formation of highly stable vesicles.

Compositions employed herein may also include, with respect to their preparation, formation and use, gaseous precursors that can be converted from a liquid or solid into a gas by temperature, pressure, pH, light, and energy (such as ultrasound). The gaseous precursors may be converted into a gas by storing or administering the gaseous precursors at reduced pressure. For example, a vial stored under reduced pressure may create a headspace of perfluoropentane or perfluorohexane gas, useful for creating a preformed gas prior to injection. Preferably, the gaseous precursor is converted to a gas by temperature. A table is set forth below that lists the phase transitions from liquid to gaseous states of several compounds, and the size of the emulsified droplets that would be required to form a vesicle of a maximum size of 10 μm.

TABLE 2

Physical Characteristics of Compounds and
Diameter of Emulsified Droplet to Form a 10 µm Vesicle*

| Compound | Molecular Weight | Boiling Point (° C.) | Density | Diameter (µm) of emulsified droplet to make 10 micron vesicle |
|---|---|---|---|---|
| perfluoro pentane | 288.04 | 29.5 | 1.7326 | 2.9 |
| 1-fluorobutane | 76.11 | 32.5 | 0.67789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |

*Source: Chemical Rubber Company Handbook of Chemistry and Physics, Robert C. Weast and David R. Lide, eds., CRC Press, Inc. Boca Raton, Florida (1989–1990).

As noted above, it is preferred to optimize the utility of the stabilizing materials and/or vesicles, especially vesicles formulated from lipids, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu, may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book*, 1966, Matheson Company Inc. More preferably, the gas entrapped in the vesicle possesses a solubility in water less than that of air; and even more preferably, the gas entrapped in the vesicle possesses a solubility in water less than that of nitrogen.

It may be desirable, in certain embodiments, to formulate vesicles from substantially impermeable polymeric materials. In these embodiments, it is generally unnecessary to employ a gas which is highly insoluble. For example, stable vesicles which comprise substantially impermeable polymeric materials may be formulated with gases having higher solubilities, for example, air or nitrogen.

The present invention describes, among other things, the use of a fluorinated gas (including a fluorinated gaseous precursor that has been converted to a gas prior to administration to a patient) in a stabilizing material and/or vesicle for administration to a patient as a blood substitute. The selection of a fluorinated gas and a stabilizing material can be used to create an effective blood substitute to deliver oxygen to tissues. The compositions of the present invention decrease the toxicity of the gas filled stabilizing materials and/or vesicles and increase the therapeutic index of the resultant ultrasound contrast media, but have even greater implications due to the superb characteristics as a blood substitute or oxygen delivery agent.

An advantageous aspect of the present invention describes that oxygen is significantly more soluble in a fluorinated gaseous solvent (i.e., a fluorinated gas or a fluorinated gaseous precursor that has been converted to a gas) than in a fluorinated liquid compound (i.e., a fluorinated gaseous precursor in a liquid state or a fluorinated liquid). Utilizing a fluorinated gaseous solvent (i.e., fluorinated gas or fluorinated gaseous precursor that has been converted to a gas) results in the use and administration of much smaller volumes of materials in therapeutic situations, facilitating smaller samples to be transported into remote first aid situations.

Additionally, fluorinated gases will be rapidly cleared from the body after oxygen delivery, whereas removal of fluorinated liquids from the body remains a technical problem in the prior art. The gases contained in the delivery system of, the present invention will be expired by the lungs, unlike conventional fluorinated liquid systems which are retained in the reticuloendothelial system. Even slight toxicities, which are magnified by time of exposure and dose, will be greatly minimized by the gaseous delivery system of the present invention.

As administered to a patient, the oxygen delivery agents described herein comprise a "gas." The term "gas" includes compounds which are a gas at room temperature (e.g., about 25° C.) as well as gaseous precursors that have been converted to a gas, by, for example, temperature and/or pressure, prior to being administered to the patient. Preferably, the gaseous precursor is a compound that is converted to a gas, due to its phase transition temperature, at a temperature of about 80° C. or less, more preferably about 70° C. or less, still more preferably at about 60° C. or less, and most preferably at about 50° C. or less. Accordingly, the oxygen delivery vehicles may be stored or manufactured as liquids. For example, a gas that has a boiling point that is higher than room temperature may be stored as a liquid and can then be converted to a gas prior to administration to the patient. Alternatively, the composition may be refrigerated or chilled, such that the liquid compound becomes a gas upon returning to room temperature, prior to administration to the patient. Accordingly, the fluorinated gas that is administered to the patient in the oxygen delivery vehicle of the present invention is a gas by virtue of having a boiling point that is lower than room temperature or by virtue of being converted to a gas by, for example, temperature or pressure changes. The compositions or oxygen delivery agents of the present invention may be used as a pharmaceutical composition or as a kit for pharmaceutical use.

The amount of the composition of the present invention to be administered depends on a variety of factors including, for example, the method of administration, the concentration of the composition, and the age, sex, weight and physical condition of the patient, as will be readily apparent to one skilled in the art in view of the present disclosure. Generally, treatment is initiated with small dosages, which can then be increased by small increments until the desired effect under the circumstances is achieved. For example, the oxygen delivery agents of the present invention may be administered in an amount of from about 0.01 ml/kg of body weight to about 40 ml/kg of body weight, preferably from about 0.1 ml/kg to about 20 ml/kg, more preferably from about 0.5 ml/kg to about 15 ml/kg, still more preferably from about 1.0 ml/kg to about 12 ml/kg, even more preferably from about 3 ml/kg to about 9 ml/kg, most preferably about 6 ml/kg of body weight. The amount of the oxygen delivery agent that is administered to the patient is dependent upon the concentration of the stabilizing material, fluorinated gas and oxygen in the aqueous carrier. If the composition of the present invention is lyophilized and reconstituted with an aqueous carrier, the amount to be administered will necessarily vary with the concentration thereof, as will be readily apparent to one skilled in the art in view of the present disclosure. Preferably, the aqueous carrier is present in an amount of 90 to 99% by weight, more preferably 98% by weight, the stabilizing material is present in an amount of 0.5 to 5% by weight, more preferably 1% by weight, and the fluorinated gas and oxygen is present in an amount of 0.5 to 5% by weight, more preferably 1% by weight. After administration of the composition of the present invention, the oxygen in the arterial blood will preferably reach a partial pressure of from about 70 mmHg to about 110 mmHg, more preferably from about 80 mmHg to about 100 mmHg, still more preferably from about 85 mmHg to about 95 mmHg, most preferably about 90 mmHg.

As the skilled artisan will recognize, the amount of oxygen dissolved in a gaseous solvent (i.e., a gas or a gaseous precursor that has been converted to a gas, by temperature or pressure, prior to administration to a patient) is a function of temperature and pressure. Under the relatively constant circulatory system temperatures of homeothermic animals, then, the variance in amounts of dissolved oxygen, or the carrying capacity of the gaseous solvent will primarily be influenced by the pressures encountered in the various tissue regions, including, for example, lungs, arteries proximal or distal to the heart, capillaries and veins. If one assumes a variable carrying capacity of between 0.10 to 0.25 picoliters of oxygen per stabilized microsphere, as calculated by Burkard and Van Liew, *J. Appl. Physiol.*, 77:2874–2878 (1994), for a particle size range between about 0.5 µm to 4.0 µm, for conditions ranging from a normal sea-level atmosphere to a hyperbaric chamber, the compositions of the present invention can act as an effective and practical blood substitutes with distinct advantages over previous systems.

For the gases (i.e., gases and gaseous precursors that have been converted to gases prior to administration to a patient) disclosed in the present invention, the carrying capacity of dissolved oxygen is about 1.8 times greater than perfluorooctylbromide (which is a liquid at room temperatures and body temperatures) and more than 4 times that of whole blood hemoglobin and more than 40 times that of plasma for equivalent volumes.

Another aspect of the invention involves unloading of oxygen in the tissues or other regions of interest in a patient. While the actual efficiency of oxygen unloading is influenced by a complex interplay of factors, such as, for example, cell permeability, blood pressure, respiratory rates of the given tissue, lifetime and size of stabilizing materials or vesicles in the capillaries, in general the stabilized vesicles of the invention will deliver oxygen at a higher $PO_2$ than either blood or liquid fluorinated compounds, such as perfluorocarbons.

With respect to effective vesicle lifetimes, the coating and stabilizing materials of the invention act to increase the effective duration of oxygen delivery. Preferably, the stabilizing material is a lipid, more preferably a phospholipid or a fluorinated lipid. The coating materials also help to stabilize the appropriately sized bubbles, under 10 µm and more preferably under 7 µm in diameter, by preventing aggregation of the bubbles, which also prevents emboli from forming in vivo. The stability in vivo of optimal phospholipid blend coated vesicles depends not only on the lipids used as coating materials but also on the gas. For example, perfluoropropane bubbles coated with phospholipid generally circulate in the body for about 20 minutes.

Oil-in-water emulsions, of which numerous examples will be apparent to one skilled in the art are also contemplated as a stabilizing composition for the gas filled vesicles described herein. Preferred oil-in-water emulsions include, for example, monosaturated oils which are liquid at 25–35° C., including, for example, soybean oil, corn oil and canola oil. Preferably, the oil-in-water emulsions are mixed with a gas or a gaseous precursor that has been converted to a gas and emulsified with, surfactants, especially amphipathic lipids, such as phospholipids or fluorinated lipids for stabilization.

Oxygen may be introduced into the compositions of the present invention prior to administration of the compositions to a patient. Alternatively, the compositions of the present invention may be administered to a patient without oxygen—with oxygen being added by the patient's own respiratory processes upon circulation through the patient's lungs. Accordingly, the compositions of the present invention will comprise a stabilizing material, a fluorinated gas and oxygen. Preferably, oxygen is combined with the fluorinated gas and stabilizing material prior to administration of the compositions to a patient.

The fluorinated gas is used in the present invention in an amount of about 15% to about 85%, more preferably about 20% to about 80%, of the total amount of gas in the stabilizing material. Oxygen is used in an amount of about 85% to about 15%, preferably from about 80% to about 20%, of the total amount of gas in the stabilizing material.

The stabilizing materials and/or vesicles of the present invention may be prepared using any of a variety of suitable methods. These are described below separately for the embodiments involving stabilizing materials and a gas, including gas filled vesicles, and embodiments involving stabilizing materials and a gaseous precursor, including gaseous precursor filled vesicles, although stabilizing materials comprising both a gas and a gaseous precursor may be a part of the present invention. As noted throughout the disclosure, a gaseous precursor may be converted to a gas, by temperature or pressure, prior to administration to the patient.

A wide variety of methods are available for the preparation of the stabilizing materials, including vesicles, such as micelles and/or liposomes. Included among these methods are, for example, shaking, drying, gas-installation, spray drying, and the like. Suitable methods for preparing vesicle compositions are described, for example, in U.S. Pat. No. 5,469,854, the disclosure of which is hereby incorporated herein by reference in its entirety. The vesicles are preferably prepared from lipids which remain in the gel state.

Micelles may be prepared using any one of a variety of conventional micellar preparatory methods which will be apparent to those skilled in the art. These methods typically involve suspension of the stabilizing material, such as a lipid compound, in an organic solvent, evaporation of the solvent, resuspension in an aqueous medium, sonication and centrifugation. The foregoing methods, as well as others, are discussed, for example, in Canfield et al., *Methods in Enzymology*, 189:418–422 (1990); El-Gorab et al, *Biochem. Biophys. Acta*, 306:58–66 (1973); *Colloidal Surfactant*, Shinoda, K., Nakagana, Tamamushi and Isejura, Academic Press, NY (1963) (especially "The Formation of Micelles", Shinoda, Chapter 1, pp. 1–88); *Catalysis in Micellar and Macromolecular Systems*, Fendler and Fendler, Academic Press, NY (1975). The disclosures of each of the foregoing publications are hereby incorporated herein by reference in their entirety.

In liposomes, the lipid compound(s) may be in the form of a monolayer or bilayer, and the monolayer or bilayer lipids may be used, to form one or more monolayers or bilayers. In the case of more than one monolayer or bilayer, the monolayers or bilayers are generally concentric. Thus, lipids may be used to form unilamellar liposomes (comprised of one monolayer or bilayer), oligolamellar liposomes (comprised of two or three monolayers or bilayers) or multilamellar liposomes (comprised of more than three monolayers or bilayers).

A wide variety of methods are available in connection with the preparation of vesicles, including liposomes. Accordingly, liposomes may be prepared using any one of a variety of conventional liposomal preparatory techniques which will be apparent to those skilled in the art, including, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., *Chemistry and Physics of Lipids,* 53:37–46 (1990), the disclosure of which is hereby incorporated herein by reference in its entirety. Suitable freeze-thaw techniques are described, for example, in International Application Serial No. PCT/US89/05040, filed Nov. 8, 1989, the disclosure of which is hereby incorporated herein by reference in its entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing, which may be achieved, for example, by the use of a mechanical shaking device, such as a Wig-L-Bug™ (Crescent Dental, Lyons, Ill.), a Mixomat, sold by Degussa AG, Frankfurt, Germany, a Capmix, sold by Espe Fabrik Pharmazeutischer Praeparate GMBH & Co., Seefeld, Oberay Germany, a Silamat Plus, sold by Vivadent, Lechtenstein, or a Vibros, sold by Quayle Dental, Sussex, England. Conventional microemulsification equipment, such as a Microfluidizer™ (Microfluidics, Woburn, Mass.) may also be used.

Spray drying may be employed to prepare gas filled vesicles. Utilizing this procedure, the stabilizing materials, such as lipids, may be pre-mixed in an aqueous environment and then spray dried to produce gas filled vesicles. The vesicles may be stored under a headspace of a desired gas.

Many liposomal preparatory techniques which may be adapted for use in the preparation of vesicle compositions are discussed, for example, in U.S. Pat. Nos. 4,728,578, 4,728,575, 4,533,254, 4,737,323, 4,162,282, 4,310,505, and 4,921,706; U.K. Patent Application GB 2193095 A; International Application Serial Nos. PCT/US85/01161 and PCT/US89/05040; Mayer et al., *Biochimica et Biophysica Acta,* 858:161–168 (1986); Hope et al., *Biochimica et Biophysica Acta,* 812:55–65 (1985); Mayhew et al., *Methods in Enzymology,* 149:64–77 (1987); Mayhew et al., *Biochimica et Biophysica Acta,* 755:169–74 (1984); Cheng et al, *Investigative Radiology,* 22:47–55 (1987); and *Liposome Technology,* Gregoriadis, ed., Vol. I, pp. 29–31, 51–67, 79–108 (CRC Press Inc., Boca Raton, Fla. 1984), the disclosures of which are hereby incorporated by reference herein in their entirety.

In connection with stabilizing materials, and especially lipid compositions in the form of vesicles, it may be advantageous to prepare the lipid compositions at a temperature below the gel to liquid crystalline phase transition temperature of the lipids. This phase transition temperature is the temperature at which a lipid bilayer will convert from a gel state to a liquid crystalline state. See, for example, Chapman et al., *J. Biol. Chem.,* 249:2512–2521 (1974), the disclosure of which is hereby incorporated by reference herein in its entirety. It is generally believed that vesicles which are prepared from lipids that possess higher gel state to liquid crystalline state phase transition temperatures tend to have enhanced impermeability at any given temperature. The main chain melting transitions of saturated diacyl-sn-glycero-3-phosphocholines are described by Derek Marsh, *CRC Handbook of Lipid Bilayers* (CRC Press, Boca Raton, Fla. 1990), at p. 139. The gel state to liquid crystalline state phase transition temperatures of various lipids will be readily apparent to one skilled in the art and are described, for example, in Gregoriadis, ed., *Liposome Technology, Vol. I,* 1–18 (CRC Press, 1984).

Compositions comprising stabilizing materials, such as lipids, and a gas can be prepared by agitating an aqueous solution containing, if desired, a stabilizing material, in the presence of a gas. The term "agitating" means any shaking motion of an aqueous solution such that gas is introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicles. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations is from about 1000 to about 20,000 per minute. More preferably, the number of reciprocations or oscillations is from about 2500 to about 8000, with reciprocations or oscillations of from about 3300 to about 5000 being even more preferred. Of course, the number of oscillations can be dependent upon the mass of the contents being agitated. Generally speaking, a larger mass requires fewer oscillations. Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple shaking methods described above, more elaborate methods can also be employed. Such elaborate methods include, for example, liquid crystalline shaking gas instillation processes and vacuum drying gas instillation processes, such as those described in U.S. Pat. No. 5,580,575, the disclosure of which is hereby incorporated herein by reference in its entirety. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay Germany), using, for example, the techniques disclosed in U.S. Pat. No. 5,542,935, the disclosure of which is hereby incorporated herein by reference in its entirety.

Foams comprise an additional embodiment of the invention. Foams find biomedical application in implants for local delivery of drugs, tissue augmentation, wound healing, and prevention of peritoneal adhesions. Phospholipid foams can be created by increasing the concentration of the phospholipids as well as by mixing with materials such as cetyl alcohol, surfactants, simethicone or polymers, such as methylcellulose. Fluorinated phospholipids may also be used to create stable, long-lasting foams. The most stable foams are generally prepared from materials which are polymerized or cross-linked, such as polymerizable phospholipids. Since foaming is also a function of surface tension reduction, detergents are generally useful foaming agents.

Foams can also be produced by shaking gas filled vesicles, wherein the foam appears on the top of the aqueous solution, and is coupled with a decrease in the volume of the aqueous solution upon the formation of foam. Preferably, the final volume of the foam is at least about two times the initial volume of the aqueous stabilizing material solution; more preferably, the final volume of the foam is at least about three times the initial volume of the aqueous solution; even more preferably, the final volume of the foam is at least about four times the initial volume of the aqueous solution; and most preferably, all of the aqueous stabilizing material solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gas filled liposomes becomes sufficiently thick so that it no longer clings to the side walls as it is swirled. At this time, the foam may cause the solution containing the gas filled liposomes to raise to a level of 30 to 35 ml.

The concentration of lipid required to form a preferred foam level will vary depending upon the type of lipid used, and may be readily determined by one skilled in the art, in view of the present disclosure. For example, in preferred embodiments, the concentration of 1,2-dipalmitoylphosphatidylcholine (DPPC) used to form gas filled liposomes according to the methods of the present invention is about 20 mg/ml to about 30 mg/ml saline solution. The concentration of distearoylphosphatidylcholine (DSPC) used in preferred embodiments is about 5 mg/ml to about 10 mg/ml saline solution. Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume essentially devoid of any liquid suspension volume and contains entirely foam.

Microemulsification is a common method of preparing an emulsion of a foam precursor. Temperature increases and/or lowered pressures will cause foaming as gas bubbles form in the liquid. As discussed above, the foam may be stabilized by, for example, surfactants, detergents or polymers.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared in accordance with the methods described herein can range in size from less than about 1 μm to greater than about 100 μm. In addition, after extrusion and sterilization procedures, which are discussed in detail below, agitation or shaking provides vesicle compositions which provide substantially no or minimal residual anhydrous lipid phase in the remainder of the solution. Bangham et al, *J. Mol. Biol.*, 13:238–252 (1965). If desired, the vesicles of the present invention may be used as they are formed, without any attempt at further modification of the size thereof For intravascular use, the vesicles preferably have diameters of less than about 30 μm, and more preferably, less than about 12 μm. For targeted intravascular use including, for example, binding to certain tissue, such as cancerous tissue, the vesicles can be significantly smaller, for example, less than about 100 nm in diameter. For enteric or gastrointestinal use, the vesicles can be significantly larger, for example, up to a millimeter in size. Preferably, the vesicles are sized to have diameters of from about 2 μm to about 100 μm.

The gas filled vesicles may be sized by a simple process of extrusion through filters wherein the filter pore sizes control the size distribution of the resulting gas filled vesicles. By using two or more cascaded or stacked set of filters, for example, a 10 μm filter followed by an 8 μm filter, the gas filled vesicles can be selected to have a very narrow size distribution around 7 to 9 μm. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and will be carried out by an extraction step which comprises extruding the vesicles from the barrel through the filter fitted to the syringe between the barrel and the needle, thereby sizing the vesicles before they are administered to a patient. The extraction step may also comprise drawing the vesicles into the syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe.

In certain preferred embodiments, the vesicle compositions may be heat sterilized or filter sterilized and extruded through a filter prior to shaking. Generally speaking, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and gaseous precursor filled vesicles provide sterile gas filled vesicles ready for administration to a patient. For example, a mixing vessel such as a vial or syringe may be filled with a filtered lipid composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to about 5 μm, more preferably, about 0.1 to about 4 μm, even more preferably, about 0.1 to about 2 μm, and still more preferably, about 1 μm. Unhydrated compound, which is generally undesirable, appears as amorphous clumps of non-uniform size.

The sterilization step provides a composition that may be readily administered to a patient for oxygen delivery. In certain preferred embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes. If desired, the extrusion and heating steps, as outlined above, may be reversed, or only one of the two steps can be used. Other modes of sterilization may be used, including, for example, exposure to gamma radiation.

In addition to the aforementioned embodiments, gaseous precursors contained in vesicles can be formulated which, by exposure to elevated temperature, decreased pressure, varying pH, or light, undergo a phase transition and convert from a liquid, including a liquid entrapped in a vesicle, to a gas, expanding to create the gas filled vesicles described herein. This technique is described in patent application Ser. No. 08/159,687, filed Nov. 30, 1993, and U.S. Pat. No. 5,542,935, the disclosures of which are hereby incorporated herein by reference in their entirety.

The preferred method of converting the gaseous precursor to a gas is by exposure to elevated temperature. Activation, transition or conversion temperature, and like terms, refer to the boiling point of the gaseous precursor and is the temperature at which the liquid to gaseous phase transition of the gaseous precursor takes place. Useful gaseous precursors are those materials which have boiling points in the range of greater than room temperature (e.g., more than 25° C.) to about 80° C., preferably from greater than room temperature to about 70° C., more preferably from greater than room temperature to about 60° C., most preferably from greater than room temperature to about 50° C. The activation or conversion temperature is particular to each gaseous precursor. An activation temperature of about 37° C., or about human body temperature, is preferred for gaseous precursors in the context of the present invention. Thus, in preferred form, a liquid gaseous precursor is activated to become a gas at about more than 25° C. to about 37° C.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature, boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. Most preferably, for the oxygen delivery agents of the present invention, the gaseous precursor is converted to a gas before it is administered to the patient. The methods of producing the temperature-activated gaseous precursor filled vesicles may be carried out at a temperature below the boiling point of the gaseous precursor. In this embodiment, the gaseous precursor is entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor is added to a container housing a lipid composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which entrap the gas of the gaseous precursor, ambient gas (e.g. air), or coentrap gas state gaseous precursor and ambient air. This phase transition can be used for optimal mixing and formation of the blood substitute. For example, the gaseous precursor can be entrapped in the lipid vesicles and as the temperature is raised beyond the boiling point of the gaseous precursor, the gas is entrapped in the vesicles. Thereafter, the composition may be administered to the patient. A water bath, sonicator or hydrodynamic activation by pulling back the plunger of a syringe against a closed stopcock may be used to activate targeted gas filled vesicles from temperature-sensitive gaseous precursors prior to intravenous injection.

As a further embodiment of this invention, by pre-forming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase is assumed to form instantaneously and substantially no gas in the newly formed vesicle has been depleted due to diffusion into the liquid, which is generally aqueous in nature. Hence, from a known liquid volume in the emulsion, one would be able to predict an upper limit to the size of the gas filled vesicle.

In embodiments of the present invention, a mixture of a lipid compound and a gaseous precursor, containing liquid droplets of defined size, may be formulated such that upon reaching a specific temperature, for example, the boiling point of the gaseous precursor, the droplets will expand into gas filled vesicles of defined size. The defined size represents an upper limit to the actual size because the ideal gas law cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is: PV=nRT, where P is pressure in atmospheres (atm); V is volume in liters (L); n is moles of gas; T is temperature in degrees Kelvin (K); and R is the ideal gas constant (22.4 L-atm/K-mole).

With knowledge of volume, density, and temperature of the liquid in the mixture of liquids, the amount, for example, in moles, and volume of liquid precursor may be calculated which, when converted to a gas, will expand into a vesicle of known volume. The calculated volume will reflect an upper limit to the size of the gas filled vesicle, assuming (i) instantaneous expansion into a gas filled vesicle, (ii) negligible diffusion of the gas over the time of the expansion, and (iii) negligible variations imparted by vascular or oncotic pressure.

Thus, for stabilization of the precursor in the liquid state in a mixture wherein the precursor droplet is spherical, the volume of the precursor droplet may be determined by the equation: Volume (spherical vesicle)=4/3 $\pi r^3$, where r is the radius of the sphere.

Once the volume is predicted, and knowing the density of the liquid at the desired temperature, the amount of liquid gaseous precursor in the droplet may be determined. In more descriptive terms, the following can be applied $$V_{gas} = 4/3 \pi (r_{gas})^3$$

by the ideal gas law, $$PV = nRT$$

substituting reveals, $$V_{gas} = nRT/P_{gas} \text{ or,}$$

$$n = 4/3 [\pi r_{gas}^3] P/RT \quad \text{(A)}$$

amount $$n = 4/3 [\pi r_{gas}^3 P/RT] \cdot MW_n$$

Converting back to a liquid volume, $$V_{liquid} = [4/3 [\pi r_{gas}^3] P/RT] \cdot MW_n/D] \quad \text{(B)}$$

where D is the density of the precursor.

Solving for the diameter of the liquid droplet, $$\text{diameter}/2 = [\tfrac{3}{4}\pi [4/3 \cdot [\pi r_{gas}^3] P/RT] MW_n/D] \quad \text{(C)}$$

which reduces to:

$$\text{Diameter} = 2[[r_{gas}^3] P/RT[MW_n/D]].$$

A representative gaseous precursor may be used to form a vesicle of defined size, for example, 10 μm diameter. In this example, the vesicle is formed in the bloodstream of a human being, thus the typical temperature would be 37° C. or 310 K. At a pressure of 1 atmosphere and using the equation in (A) above, $7.54 \times 10^{-17}$ moles of gaseous precursor would be required to fill the volume of a 10 μm diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74 \times 10^{-15}$ grams of this precursor would be required for a 10 μm vesicle. Extrapolating further, and with the knowledge of the density, equation (B) above further predicts that $8.47 \times 10^{-16}$ mL of liquid precursor is necessary to form a vesicle with an upper limit of 10 μm.

Finally, using equation (C) above, a mixture, for example, an emulsion containing droplets with a radius of 0.0272 μm or a corresponding diameter of 0.0544 μm, is formed to make a gaseous precursor filled vesicle with an upper limit of a 10 μm vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

As an example of using more than one gas, including, for example, oxygen and a fluorinated gas or a fluorinated gaseous precursor that has been converted to a gas, the following can be applied:

$$V_{gas} = 4/3 \pi (r_{gas})^3$$

by the ideal gas law, where n may be a mixture of, for example, three gases A, B and C, $$PV = (n_A + n_B + n_C)RT$$

substituting reveals, $$V_{gas} = (n_A + n_B + n_C)RT/P_{gas}$$

then substituting for $V_{gas}$:

$$(n_A + n_B + n_C)RT/P_{gas} = 4/3 \pi (r_{gas})^3$$

or, rearranging:

$$3/4(n_A + n_B + n_C)RT/\pi P_{gas} = (r_{gas})^3$$

or, $$r_{gas} = (3/4(n_A + n_B + n_C)RT/\pi P_{gas}).$$

Thus, the radius of the bubble can be determined by subtracting the number of moles of oxygen gas that has been eliminated or diffused from the bubble. If $n_C$ represents the number of moles of oxygen in the bubble, the resultant radius, $r'_{gas}$ can be expressed as:

$$r'_{gas} = (3/4(n_A + n_B)RT/\pi P_{gas}).$$

This formula applies regardless of the total number of gaseous components in the mixture. A gaseous mixture having three components was chosen for illustration only.

In reality some deviation from ideality depicted above is expected with real gases caused by collapsing vesicle walls or layers. Additionally, weak molecular interactions between the gas atoms and the exposed functional groups of the vesicle cause deviations from ideality. In any case, the above analysis is useful for approximating the volume change of the vesicles with changing pressure.

Figure 1B:
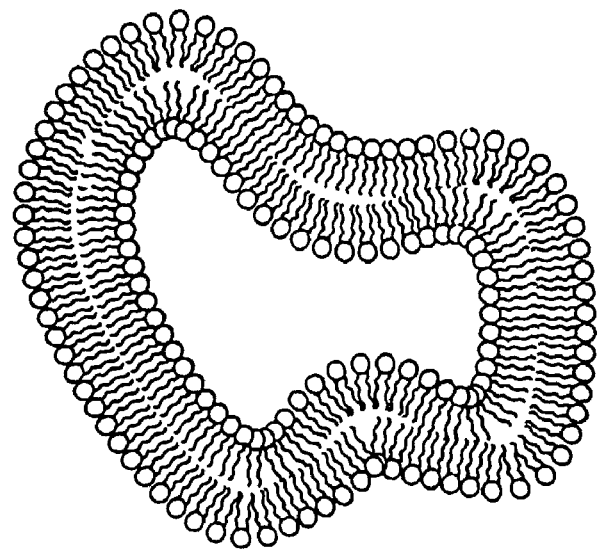
FIG. 1B is a cross-sectional view of a hypothetical semi-collapsed bilayer vesicle (not drawn to scale).

FIGS. 1A and 1C show cross-sections of hypothetical vesicles, where the spherical structure is stabilized on the inside by the partial pressures of the constituent gases as well as by the physical and chemical nature of the vesicle shell. On the outside, hydrostatic pressure and surface tension exert forces tending to cause the vesicle to collapse. The size of the vesicle will be a function of these competing internal and external forces. FIGS. 1B and 1D show cross-sections of semi-collapsed vesicles. This illustrates the effect of degassing the external aqueous environment, which causes outward diffusion of the trapped internal gases since the pressures inside and outside of the vesicle cannot reach equilibrium. However, when the internal component is a relatively water-insoluble gas, such as a perfluorocarbon, gas diffusion out will be minimized. The volume change of the vesicle, similarly, will be less than predicted from the ideal gas law, because of the intramolecular repulsion that the hydrophobic lipid tails exhibit in any potential compaction. Only the symmetry of the sphere will be appreciably altered. Eventually, as saturation of the external environment occurs, the vesicles will tend to return to spherical shapes.

Figure 2:
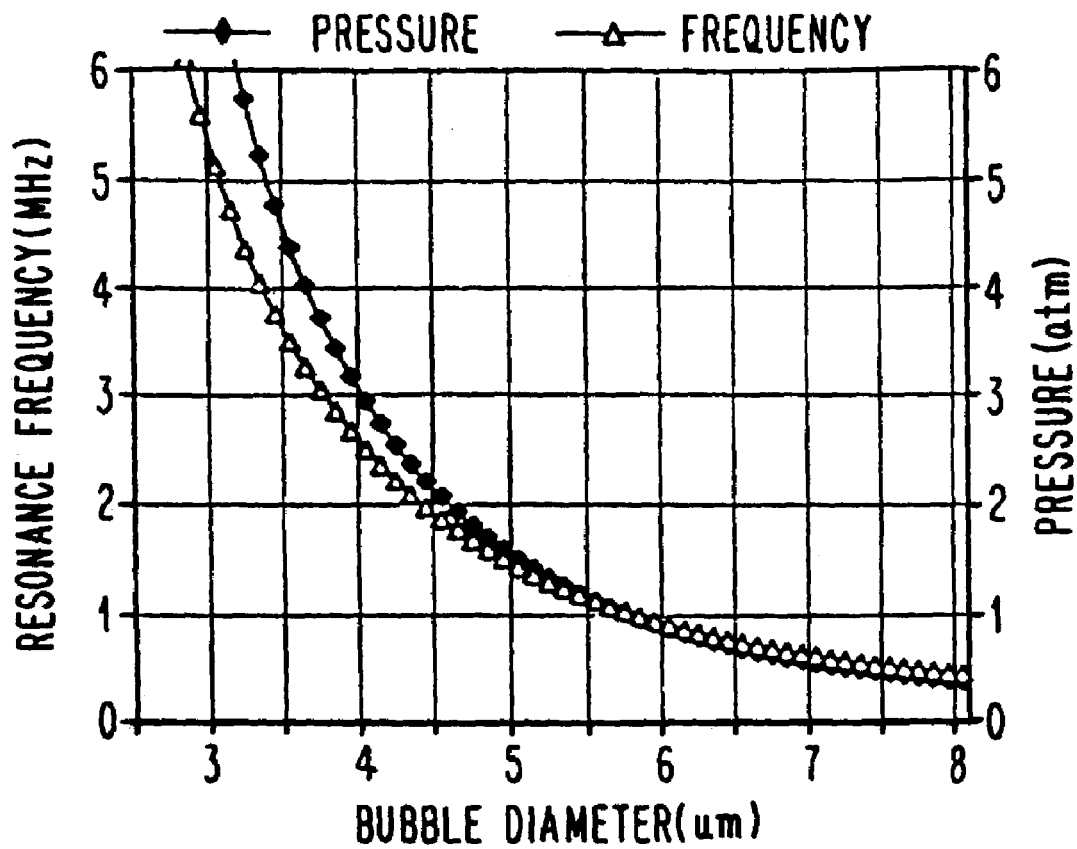
FIG. 2 is a graph showing the relationship between pressure, bubble size and resonance frequency.

The real, non-ideal volume changes of vesicles with applied pressure is shown in FIG. 2. If an ultrasonic contrast agent comprising a vesicle with a protective shell is introduced into a region that is being imaged, the microspheres will respond with a particular resonance frequency. In the region of interest, it may be assumed that the average size of the vesicles $r_1$ and the pressures applied to the vesicles, like hydrostatic pressures, diastolic pressures and systolic pressure and the radiation pressure from the ultrasonic transducer, the pressures may be classified as $P_{11}$, $P_{12}$, $P_{13}$, etc. In this model, Van der Waal's equation, the equation of state for real gases and the equation for a spherical volume, were used to determine the pressure versus the bubble size relationship.

$$P = \sum_{i=1}^{n} P_i \qquad \text{Equation 1}$$

$$(P+n^2a/V^2)(V-nb)=nRT \qquad \text{Equation 2}$$

$$V=4/3\ \pi r^3 \qquad \text{Equation 3}$$

where P is the pressure in atmospheres, V is the volume in cm$^3$, R is the universal gas constant, T is the temperature in Kelvin, n is the number of moles, a is a measure of attractive force between molecules, b is for the finite volume of the molecules and hence their compressibility, and r is the radius of the vesicle. In this scenario, the vesicles will have a certain scattering cross-section. In other words, the vesicles have a resonance frequency that is dependent upon the dimensions of the vesicles. In the model that was generated, a vesicle with the diameter of 6 μm has a resonance frequency of 1 MHz. The pressure inside this vesicle was classified to have 1 atmosphere. A pressurization of the vesicle occurred, the size of the vesicle diminished and its resonance frequency shifted to a higher frequency, as shown in FIG. 2.

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere, as discussed above.

This embodiment for preparing gas filled vesicles may be applied to all gases and/or gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation:

$$ln\, x_a = ln(1-x_b) = \Delta H_{fus} R(1/T_o - 1/T)$$

where: $x_a$ is the mole fraction of the solvent; $x_b$ is the mole fraction of the solute; $\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as:

$$x^b = \Delta H_{fus}/R[T-T_o/T_oT] \approx \Delta H_{fus} \Delta T/RT_o^2$$

The above equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as follows.

$$X_b = m/[m+1000/m_a] \approx mMa/1000$$

where Ma is the molecular weight of the solvent.

Thus, substituting for the fraction $x_b$:

$$\Delta T = [M_a RT_o^2/1000\Delta H_{fus}]m$$

or $$\Delta T = K_f m, \text{ where } K_f = M_a RT_o^2/1000\Delta H_{fus}$$

$K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 μm. Alternatively, filtering may be performed during in vivo administration of the vesicles such that a filter of about 0.22 μm is employed;

(b) microemulsification whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor Filled vesicles float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying is useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state.

Preferred methods for preparing the temperature activated gaseous precursor filled vesicles comprise mechanically agitating an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool. Other methods for preparing gaseous precursor filled vesicles can involve shaking or mechanically agitating an aqueous solution of, for example, a lipid and a gaseous precursor, and separating the resulting gaseous precursor filled vesicles.

Aqueous filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci,* 75:4194–4198 (1978). In contrast, the vesicles made according to certain preferred embodiments described herein are gaseous precursor filled, which imparts greater flexibility, since gaseous precursors after gas formation are more compressible and compliant than an aqueous solution.

The methods contemplated by the present invention provide for mechanically agitating an aqueous solution comprising a lipid, in the presence of a temperature activatable gaseous precursor. Preferably, the shaking is of sufficient force such that a foam is formed within a short period of time, such as about 30 minutes, and preferably within about 20 minutes, and more preferably, within about 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, a gas, such as air (which comprises about 21% oxygen), may be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Accordingly, the present invention includes co-entrapment of air and/or other gases along with gaseous precursors.

Hence, the gaseous precursor filled vesicles can be used in substantially the same manner as the gas filled vesicles described herein, once converted to a gas by application of, for example, increased temperatures. It is preferred that the gaseous precursors undergo phase transitions from liquid to gaseous states prior to intravenous injection, for example, by thermal, mechanical or optical means.

Vesicle compositions which comprise vesicles formulated from proteins (also referred to as protein encapsulated microbubbles), such as albumin vesicles, may be prepared by various processes, as will be readily apparent to one skilled in the art in view of the present disclosure. Suitable methods include those described, for example, in U.S. Pat. Nos. 4,572,203, 4,718,433, 4,774,958, and 4,957,656, the disclosures of each of which are hereby incorporated herein by reference in their entirety. Included among the methods are those which involve sonicating a solution of a protein. In preferred form, the starting material may be an aqueous solution of a heat-denaturable, water-soluble protein. The encapsulating protein is preferably heat-sensitive so that it can be partially insolubilized by heating during sonication. Suitable heat-sensitive proteins include, for example, albumin, hemoglobin, and collagen, preferably, the protein is a human protein, with human serum albumin (HSA) being more preferred. HSA is available commercially as a sterile 5% aqueous solution, which is suitable for use in the preparation of protein-based vesicles. As would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

Protein-based vesicles may be prepared using equipment which is commercially available. For example, in connection with a feed perparation operation as described, for example, in U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonciating vessel, in series. Heat exhanger equipment of this type may be obtained from ITT Standard (Buffalo, N.Y.). The heat exchanger maintains operating temperature for the sonciation process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commerically available sonicators operating at about 10 or 20 kHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficeint to produce cavitation in the liquid being sonicated. Feed flow rates may range from about 50 ml/min to about 1000 ml/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally, intense foaming and aerosolating are important for obtaining a blood substitute having enhanced concentration and stability. To promote foaming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based vesicles may also involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as gluteraldehyde. For example, the vesicles may be reacted with 0.25 grams of 50% aqueous gluteradehyde per gram of protein at pH 4.5 for 6 hours. The unreacted gluteraldehyde may then be washed away from the protein.

Vesicle compositions which comprise vesicles formulated from polymers may be prepared by various processes, as will be readily apparent to one skilled in the art, in view of the present disclosure. Exemplary processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures described in U.S. Pat. Nos. 4,179,546, 3,945,956, 4,108,806, 3,293,114, 3,401,475, 3,479,811, 3,488,714, 3,615,972, 4,549,892, 4,540,629, 4,421,562, 4,420,442, 4,898,734, 4,822,534, 3,732,172, 3,594,326, and 3,015,128; Japan Kokai Tokkyo Koho 62 286534, British Patent No. 1,044,680, Deasy, *Microencapsulation and Related Drug Processes*, Vol. 20, Chs. 9 and 10, pp. 195–240 (Marcel Dekker, Inc., N.Y., 1984), Chang et al., *Canadian J. of Physiology and Pharmacology*, 44:115–129 (1966), and Chang, *Science*, 146:524–525 (1964), the disclosures of each of which are hereby incorporated herein by reference in their entirety.

In accordance with a preferred synthesis protocol, the vesicles may be prepared using a heat expansion process, such as, for example, the process described in U.S. Pat. Nos. 4,179,546, 3,945,956, and 4,108,806, British Patent No. 1,044,680, and Japan Kokai Tokkyo Koho 62 286534. In general terms, the heat expansion process may be carried out by preparing vesicles of an expandable polymer or copolymer which may contain in their void (cavity) a volatile liquid (gaseous precursor). The vesicle is then heated, plasticising the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density, and are thus preferred. The foregoing described process is well known in the art, and may be referred to as the heat expansion process for preparing low density vesicles.

Polymers useful in the heat expansion process will be readily apparent to one skilled in the art and include thermoplastic polymers or copolymers, including polymers or copolymers of many of the monomers described above. Preferable of the polymers and copolymers described above include the following copolymers: polyvinylidene-polyacrylonitrile. polyvinylidene-polyacrylonitrile-polymethylmethacrylate, and polystyrene-polyacrylonitrile. A most preferred copolymer is polyvinylidene-polyacrylonitrile.

Volatile liquids useful in the heat expansion process will also be well known to one skilled in the art and include: aliphatic hydrocarbons such as ethane, ethylene, propane, propene, butane, isobutane, neopentane, acetylene, hexane, heptane; chlorofluorocarbons such as $CCl_3F$, $CCl_2F_3$, $CClF_3$, $CClF_2$—$CCl_2F_2$, chloroheptafluorocyclobutane, and 1,2-dichlorohexafluorocyclobutane; tetraalkyl silanes, such as tetramethyl silane, trimethylethyl silane, trimethylisopropyl silane, and trimethyl n-propyl silane; as well as perfluorocarbons, including the perfluorocarbons described above. In general, it is important that the volatile liquid not be a solvent for the polymer or copolymer being utilized. It is also preferred that the volatile liquid have a boiling point that is below the softening point of the involved polymer or copolymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases also. Also, mildly preheating the vesicles in water in the presence of hydrogen peroxide prior to definitive heating and expansion may pre-soften the vesicle to allow expansion to occur more readily.

For example, to produce vesicles from synthetic polymers, vinylidene and acrylonitrile may be copolymerized in a medium of isobutane liquid using one or more of the foregoing modified or unmodified literature procedures, such that isobutane becomes entrapped within the vesicles. When such vesicles are then heated to a temperature of from about 80° C. to about 120° C., the isobutane gas expands, which in turn expands the vesicles. After heat is removed, the expanded polyvinylidene and acrylonitrile copolymer vesicles remain substantially fixed in their expanded position. The resulting low density vesicles are extremely stable both dry and suspended in an aqueous media. Isobutane is utilized herein merely as an illustrative liquid, with the understanding that other liquids which undergo liquid/gas transitions at temperatures useful for the synthesis of these vesicles and formation of the very low density vesicles upon heating can be substituted for isobutane. Similarly, monomers other than vinylidene and acrylonitrile may be employed in preparing the vesicles.

In certain preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have encapsulated therein isobutane liquid. Such microspheres are sold as a dry composition and are approximately 50 µm in size. The EXPANCEL 551 DE™ microspheres have a specific gravity of only 0.02 to 0.05, which is between one-fiftieth and one-twentieth the density of water.

As one skilled in the art will recognize, any of the stabilizing materials and/or vesicle compositions may be lyophilized for storage, and may be reconstituted or rehydrated, for example, with an aqueous medium (such as sterile water, phosphate buffered solution, or aqueous saline solution), with the aid of vigorous agitation. Lyophilized preparations generally have the advantage of greater shelf life. To prevent agglutination or fusion of the lipids and/or vesicles as a result of lyophilization, it may be useful to include additives which prevent such fusion or agglutination from occurring. Additives which may be useful include sorbitol, mannitol, sodium chloride, glucose, trehalose, polyvinyl-pyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosure of which is hereby incorporated herein by reference in its entirety.

The concentration of lipid required to form a desired stabilized vesicle level will vary depending upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The amount of composition which is administered to a patient can vary, as described herein.

Another embodiment of preparing a gas and/or gaseous precursor filled vesicle comprises combining at least one lipid and a gaseous precursor and agitating until gaseous precursor filled vesicles are formed. The gaseous precursor may remain a gaseous precursor until the time of use. That is, the gaseous precursor may be activated by temperature, for example, prior to administration to a patient.

Alternatively, the gaseous precursors may be utilized to create stable gas filled vesicles which are pre-formed prior to use. In this embodiment, the gaseous precursor is added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas for example, air (which comprises about 21% oxygen), or coentrap gas state gaseous precursor and ambient air. This phase transition can be used for optimal mixing and stabilization of the delivery vehicle. For example, a fluorinated gaseous precursor can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled vesicles result.

According to the methods contemplated by the present invention, the presence of gas, such as and not limited to air (which comprises about 21% oxygen), may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more anti-bactericidal agents and/or preservatives may be included in the formulation of the compositions, such as sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, for example, intravascularly or intraperitoneally. The appropriate means of sterilization will be apparent to the artisan instructed by the present description of the stabilized gas filled vesicles and their use. The compositions are generally stored as an aqueous suspension but in the case of dried or lyophilized vesicles or dried or lyophilized lipidic spheres the compositions may be stored as a dried or lyophilized powder ready to be reconstituted or rehydrated prior to use.

Because of their ability to deliver oxygen and function as blood substitutes, the compositions of the present invention may be used in a wide variety of in vivo and in vitro applications, including those described, for example, by Lowe, *Comp. Biochem. Physiol.,* 87A(4):825–838 (1987), the disclosure of which is hereby incorporated by reference herein in its entirety. For example, the compositions of the present invention may be administered to a patient to improve tissue oxygenation and reduce the severity of infarcts arising from cerebral, myocardial or intestinal ischaemia. The compositions of the present invention may also be administered to a patient to enhance oxygenation of tumors (such as, for example, anoxic/hypoxic tumors), which will result in increased sensitization of the tumors to radiation therapy and/or chemotherapy. In view of their diagnostic imaging and oxygen transporting properties, the compositions of the present invention may be administered as dual diagnostic and therapeutic agents in oncology. The compositions of the present invention may also be used in liquid ventilation and for treating decompression sickness. For in vitro applications, the compositions of the present invention may be used for oxygenating and maintaining the viability of mammalian and non-mammalian cells in culture, which may be advantageous in basic and applied research.

In conjunction with their use as oxygen delivery agents, the compositions of the present invention may also be used as contrast media in diagnostic imaging. Diagnostic imaging is a means to visualize internal body regions of a patient, and includes, for example, ultrasound (US), magnetic resonance imaging (MRI), nuclear magnetic resonance (NMR), computed tomography (CT), electron spin resonance (ESR); nuclear medicine when the contrast medium includes radioactive material; and optical imaging, particularly with a fluorescent contrast medium. Diagnostic imaging includes promoting the rupture of oxygen delivery agents via the methods of the present invention. For example, ultrasound may be used to visualize the oxygen delivery agents and verify the localization of the oxygen delivery agents in certain tissue. In addition, ultrasound may be used to promote rupture of the oxygen delivery agents once they reach the intended target or region of interest, so that oxygen may be released in the desired region of interest.

The compositions of the invention may be administered to the patient by a variety of means, which will vary depending upon the intended application. As one skilled in the art would recognize, the compositions, stabilizing materials and/or vesicles of the present invention can be administered in various fashions, for example, intrarectally, transdermally, orally, intraperitoneally, parenterally, intravenously, intralymphatically, intratumorly, intramuscularly, interstitially, intra-arterially, subcutaneously, intraocularly, intrasynovially, transepithelially, pulmonarily via inhalation, ophthalmically, sublingually, buccally, or nasal inhalation via insufflation or nebulization. Preferably, the stabilizing materials and/or vesicles are administered intra-arterially.

The oxygen delivery vehicles, stabilizing materials and/or vesicles of the present invention are preferably administered as an infusion. "Infusion" refers to intravascular or intra-arterial administration at a rate of, for example, less than about 1 cc/second, more preferably less than about 0.5 cc/second or 30 cc/minute. Varying the rate of infusion is also desirable. For example, infusion may initially be started at a rate of about 1.0 to about 4.0 cc/second, followed by a more sustained infusion rate of about 0.1 cc/second. The fast infusion rate initially achieves the optimal level of the oxygen delivery agent in the blood. The slower infusion rate is designed to maintain a steady state as the fluorinated gas is cleared from the lungs. The slow infusion rate is better tolerated hemodynamically.

The use of rupturing ultrasound, as discussed in detail below, may increase the transdermal delivery of oxygen. Further, a mechanism may be used to monitor and modulate delivery of the stabilizing compositions, and of oxygen. For example, diagnostic ultrasound may be used to visually monitor the bursting of the gas filled vesicles and modulate oxygen delivery and/or a hydrophone may be used to detect the sound of the bursting of the gas filled vesicles and modulate oxygen delivery.

The delivery of oxygen from the stabilizing materials of the present invention using ultrasound is best accomplished for tissues which have a good acoustic window for the transmission of ultrasonic energy. This is the case for most tissues in the body such as muscle, the heart, the liver and most other vital structures. In the brain, in order to direct the ultrasonic energy past the skull a surgical window may be necessary.

The invention is useful, inter alia, in delivering oxygen to a patient's lungs. For pulmonary applications of dried or lyophilized powdered liposomes may be administered via inhaler. Aqueous suspensions of liposomes or micelles may be administered via nebulization. Gas filled liposomes of the present invention are lighter than, for example, conventional liquid filled liposomes which generally deposit in the central proximal airway rather than reaching the periphery of the lungs. It is therefore believed that the gas filled liposomes of the present invention may improve delivery of oxygen to the periphery of the lungs, including the terminal airways and the alveoli. For application to the lungs, the gas filled liposomes may be applied through nebulization.

In applications such as the targeting of the lungs, which are lined with lipids, the therapeutic may be released upon aggregation of the gas filled liposomes with the lipids lining the targeted tissue. Additionally, the gas filled liposomes may burst after administration without the use of ultrasound. Thus, ultrasound need not be applied to release the oxygen in the above type of administration.

It is a further embodiment of this invention in which ultrasound activation affords site specific delivery of the stabilizing compositions. Generally, the gas and/or gaseous precursor containing vehicles are echogenic and visible on ultrasound. Ultrasound can be used to image the target tissue and to monitor the oxygen delivery vehicles as they pass through the treatment region. As increasing levels of ultrasound are applied to the treatment region, this breaks apart the delivery vehicles and/or releases the oxygen within the treatment region. Oxygen release and/or vesicle rupture can be monitored ultrasonically by several different mechanisms. The destruction of vesicles results in the eventual dissolution of the ultrasound signal. Prior to signal dissolution, however, the vehicles provide an initial burst of signal. In other words as increasing levels of ultrasound energy are applied to the treatment zone containing the vehicles, there is a transient increase in signal. This transient increase in signal may be recorded at the fundamental frequency, the harmonic, odd harmonic or ultraharmonic frequency.

Generally, the therapeutic delivery systems of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may also be buffered, if desired, to provide a pH range of about pH 5 to about pH 7.4. In addition, dextrose may be preferably included in the media. Further solutions that may be used for administration of gas filled liposomes include, but are not limited to almond oil, corn oil, cottonseed oil, ethyl oleate, isopropyl myristate, isopropyl palmitate, mineral oil, myristyl alcohol, octyldodecanol, olive oil, peanut oil, persic oil, sesame oil, soybean oil, and squalene.

The size of the stabilizing materials and/or vesicles of the present invention will depend upon the intended use. With smaller liposomes, resonant frequency ultrasound will generally be higher than for the larger liposomes. Sizing also serves to modulate resultant liposomal biodistribution and clearance. In addition to filtration, the size of the liposomes can be adjusted, if desired, by procedures known to one skilled in the art, such as shaking, microemulsification, vortexing, filtration, repeated freezing and thawing cycles, extrusion, extrusion under pressure through pores of a defined size, sonication, homogenization, the use of a laminar stream of a core of liquid introduced into an immiscible sheath of liquid. See, for example, U.S. Pat. Nos. 4,728,578, 4,728,575, 4,737,323, 4,162,282, 4,310,505, 4,921,706, and 4,533,254; U.K. Patent Application GB 2193095 A; International Applications PCT/US85/01161 and PCT/US89/05040; Mayer et al., *Biochimica et Biophysica Acta*, 858: 161–168 (1986); Hope et al., *Biochimica et Biophysica Acta*, 812:55–65 (1985);; Mayhew et al., *Methods in Enzymology*, 149:64–77 (1987); Mayhew et al., *Biochimica et Biophysica Acta*, 755:169–74 (1984); Cheng et al, *Investigative Radiology*, 22:47–55 (1987); and *Liposomes Technology*, Gregoriadis, ed., Vol. I, pp. 29–37, 51–67 and 79–108 (CRC Press Inc, Boca Raton, Fla., 1984). The disclosures of each of the foregoing patents, publications and patent applications are hereby incorporated by reference herein in their entirety. Extrusion under pressure through pores of defined size is a preferred method of adjusting the size of the liposomes.

Since vesicle size influences biodistribution, different size vesicles may be selected for various purposes. For example, for intravascular application, the preferred size range is a mean outside diameter between about 30 nm and about 10 μm, with the preferable mean outside diameter being about 5 μm. More specifically, for intravascular application, the size of the vesicles is preferably about 10 μm or less in mean outside diameter, and preferably less than about 7 μm, and more preferably less than about 5 μm in mean outside diameter. Preferably, the vesicles are no smaller than about 30 nm in mean outside diameter. To provide therapeutic delivery to organs such as the liver and to allow differentiation of tumor from normal tissue, smaller vesicles, between about 30 nm and about 100 nm in mean outside diameter, are preferred. For embolization of a tissue such as the kidney or the lung, the vesicles are preferably less than about 200 μm in mean outside diameter. For intranasal, intrarectal or topical administration, the vesicles are preferably less than about 100 μm in mean outside diameter. Large vesicles, e.g., between 1 and 10 μm in size, will generally be confined to the intravascular space until they are cleared by phagocytic elements lining the vessels, such as the macrophages and Kupffer cells lining capillary sinusoids. For passage to the cells beyond the sinusoids, smaller vesicles, for example, less than about a micron in mean outside diameter, e.g., less than about 300 nm in size, may be utilized. In preferred embodiments, the vesicles are administered individually, rather than embedded in a matrix, for example.

For in vitro use, such as cell culture applications, the gas filled vesicles may be added to the cells in cultures and then incubated. Subsequently sonic energy can be applied to the culture media containing the cells and liposomes.

In carrying out the imaging methods of the present invention, the stabilizing materials and vesicle compositions can be used alone, or in combination with diagnostic, therapeutic or other agents. Such other agents include excipients such as flavoring or coloring materials.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained. With respect to ultrasound, ultrasonic imaging techniques, including second harmonic imaging, and gated imaging, are well known in the art, and are described, for example, in Uhlendorf, "Physics of Ultrasound Contrast Imaging: Scattering in the Linear Range", *IEEE Transactions on Ultrasonics, Ferroelectrics, and Frequency Control*, 14(1):70–79 (1994) and Sutherland, et al., "Color Doppler Myocardial Imaging: A New Technique for the Assessment of Myocardial Function", *Journal of the American Society of Echocardiography*, 7(5):441–458 (1994), the disclosures of each of which are hereby incorporated herein by reference in their entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the targeted contrast media of the present invention which may be targeted to the desired site, for example, blood clots. Other harmonic signals, such as odd harmonics signals, for example, 3x or 5x, would be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there will be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of oxygen. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle compositions, which is also referred to as rupturing ultrasound. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may also be pulsed. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). In general, frequency for therapeutic ultrasound preferably ranges between about 0.75 and about 3 MHz, with from about 1 and about 2 MHz being more preferred. In addition, energy levels may vary from about 0.5 Watt (W) per square centimeter ($cm^2$) to about 5.0 $W/cm^2$, with energy levels of from about 0.5 to about 2.5 $W/cm^2$ being preferred. Energy levels for therapeutic ultrasound involving hyperthermia are generally from about 5 $W/cm^2$ to about 50 $W/cm^2$. For very small vesicles, for example, vesicles having a diameter of less than about 0.5 µm, higher frequencies of sound are generally preferred because smaller vesicles are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosure of which is hereby incorporated by reference herein in its entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the targeted compositions, for example, targeted vesicle compositions, within the targeted tissue. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, *Ultrasonics Sonochemistry*, 3:1–5 (1996), the disclosure of which is hereby incorporated by reference herein in its entirety.

For use in ultrasonic imaging, preferably, the vesicles of the invention possess a reflectivity of greater than 2 dB, more preferably between about 4 dB and about 20 dB. Within these ranges, the highest reflectivity for the vesicles of the invention is exhibited by the larger vesicles, by higher concentrations of vesicles, and/or when higher ultrasound frequencies are employed.

For therapeutic oxygen delivery, the rupturing or disruption of oxygen containing stabilizing materials and/or vesicle compositions of the invention, for example, may be carried out by applying ultrasound of a certain frequency to the region of the patient where therapy is desired, after the stabilizing materials, liposomes or vesicles have been administered to or have otherwise reached that region of interest. Specifically, it has been unexpectedly found that when ultrasound is applied at a frequency corresponding to the peak resonant frequency of the oxygen containing gas filled vesicles, the vesicles will rupture and release the oxygen. The peak resonant frequency can be determined either in vivo or in vitro, but preferably in vivo, by exposing the stabilizing materials or vesicles, including liposomes, to ultrasound, receiving the reflected resonant frequency signals and analyzing the spectrum of signals received to determine the peak, using conventional means. The peak, as so determined, corresponds to the peak resonant frequency, or second harmonic, as it is may be termed.

Preferably, the stabilizing materials and/or vesicle compositions of the invention have a peak resonant frequency of between about 0.5 MHz and about 10 MHz. Of course, the peak resonant frequency of the gas filled vesicles of the invention will vary depending on the outside diameter and, to some extent, the elasticity or flexibility of the liposomes, with the larger and more elastic or flexible liposomes having a lower resonant frequency than the smaller and less elastic or flexible vesicles.

The oxygen containing gas filled vesicles will also rupture, for example, when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and oxygen release is improved, appreciable tissue heating does not generally occur (frequently no increase in temperature above about 2° C.), and less overall energy is required. Thus, application of ultrasound at the peak resonant frequency, while not required, is most preferred.

For diagnostic or therapeutic ultrasound, any of the various types of diagnostic ultrasound imaging devices may be employed in the practice of the invention, the particular type or model of the device not being critical to the method of the invention. Also suitable are devices designed for administering ultrasonic hyperthermia, as described in U.S. Pat.

Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency increased until the vesicle is visualized on ultrasound (for diagnostic ultrasound applications) or ruptures (for therapeutic ultrasound applications).

Although application of the various principles will be readily apparent to one skilled in the art, in view of the present disclosure, by way of general guidance, for gas filled vesicles of about 1.5 to about 10 μm in mean outside diameter, the resonant frequency will generally be in the range of about 1 to about 10 MHz. By adjusting the focal zone to the center of the target tissue (e.g., the tumor) the gas filled vesicles can be visualized under real time ultrasound as they accumulate within the target tissue. Using the 7.5 MHz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of oxygen from the gas filled vesicles, but much greater release can be accomplished by using a higher power.

By switching the transducer to the doppler mode, higher power outputs are available, up to 2.5 W/cm$^2$ from the same transducer. With the machine operating in doppler mode, the power can be delivered to a selected focal zone within the target tissue and the gas filled vesicles can be made to release their oxygen. Selecting the transducer to match the resonant frequency of the gas filled vesicles will make this process of oxygen release even more efficient.

For larger diameter gas filled vesicles, e.g., greater than 3 μm in mean outside diameter, a lower frequency transducer may be more effective in accomplishing oxygen release. For example, a lower frequency transducer of 3.5 MHz (20 mm curved array model) may be selected to correspond to the resonant frequency of the gas filled vesicles. Using this transducer, 101.6 milliwatts per cm$^2$ may be delivered to the focal spot, and switching to doppler mode will increase the power output (SPTA) to 1.02 W/cm$^2$.

To use the phenomenon of cavitation to release the oxygen within the gas filled stabilizing materials and/or vesicles, lower frequency energies may be used, as cavitation occurs more effectively at lower frequencies. Using a 0.757 MHz transducer driven with higher voltages (as high as 300 volts) cavitation of solutions of gas filled liposomes will occur at thresholds of about 5.2 atmospheres.

The ranges of energies transmitted to tissues from diagnostic ultrasound on commonly used instruments, such as the Piconics Inc. (Tyngsboro, Mass.) Portascan general purpose scanner with receiver pulser 1966 Model 661; the Picker (Cleveland, Ohio) Echoview 8L Scanner including 80C System or the Medisonics (Mountain View, Calif.) Model D-9 Versatone Bidirectional Doppler, are well known to one skilled in the art, and are described by, for example, Carson et al., Ultrasound in Med. & Biol., 3:341–350 (1978), the disclosure of which is hereby incorporated herein by reference in its entirety. In general, these ranges of energies employed in pulse repetition are useful for diagnosis and monitoring gas filled liposomes but are insufficient to rupture the gas filled liposomes of the present invention. Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the liposomes and rupturing to provide local delivery of oxygen.

The frequency of the sound used may vary from about 0.025 to about 100 MHz. Frequency ranges between about 0.75 and about 3 MHz are preferred and frequencies between about 1 and about 2 MHz are most preferred. Commonly used therapeutic frequencies of about 0.75 to about 1.5 MHz may be used. Commonly used diagnostic frequencies of about 3 to about 7.5 MHz may also be used. For very small vesicles, e.g., below 0.5 μm in mean outside diameter, higher frequencies of sound may be preferred as these smaller vesicles will absorb sonic energy more effectively at higher frequencies of sound. When very high frequencies are used, e.g., over 10 MHz, the sonic energy will generally have limited depth penetration into fluids and tissues. External application may be preferred for the skin and other superficial tissues, but for deep structures, the application of sonic energy via interstitial probes or intravascular ultrasound catheters may be preferred.

As discussed above, the oxygen delivery vehicles of the present invention may be used in connection with ultrasound, including diagnostic and therapeutic ultrasound. The oxygen delivery vehicle may be used alone, or may be used in combination with various contrast agents, including conventional contrast agents, which may serve to increase their effectiveness as contrast agents for diagnostic imaging and/or oxygen delivery. The present oxygen delivery vehicles may also be used, if desired, in connection with computed tomography (CT) imaging, magnetic resonance imaging (MRI) or other of the various forms of diagnostic imaging that are well known to one skilled in the art.

Examples of suitable contrast agents for use with MRI in combination with the present stabilizing materials include, for example, stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. Preferable transition, lanthanide and actinide elements include, for example, Gd(III), Mn(II), Cu(II), Cr(III), Fe(II), Fe(III), Co(II), Er(II), Ni(II), Eu(III) and Dy(III). More preferably, the elements may be Gd(III), Mn(II), Cu(II), Fe(II), Fe(III), Eu(III) and Dy(III), most preferably Mn(II) and Gd(III). The foregoing elements may be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, such as iron sulfides, and ferric salts, such as ferric chloride.

The above elements may also be bound, for example, through covalent or noncovalent association, to complexing agents, including lipophilic derivatives thereof, or to proteinaceous macromolecules. Preferable complexing agents include, for example, diethylenetriaminepentaacetic acid (DTPA), ethylenediaminetetraacetic acid (EDTA), 1,4,7,10-tetraazacyclododecane-N,N',N',N'''-tetraacetic acid (DOTA), 1,4,7,10-tetraazacyclododecane-N,N',N'''-triacetic acid (DOTA), 3,6,9-triaza-12-oxa-3,6,9-tricarboxymethylene-10-carboxy-13-phenyltridecanoic acid (B-19036), hydroxybenzyl-ethylenediamine diacetic acid (HBED), N,N'-bis(pyridoxyl-5-phosphate)ethylene diamine, N,N'-diacetate (DPDP), 1,4,7-triazacyclononane-N,N',N"-triacetic acid (NOTA), 1,4,8,11-tetraazacyclotetradecane-N,N',N", N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)ethylenediamine-N,N'-diacetate (EDTA-DDP); N,N'-bis-(carboxyoctadecylamidomethyl-N-2,3-dihydroxypropyl)ethylenediamine-N,N'-diacetate (EDTA-ODP); and N,N'-Bis(carboxylaurylamidomethyl-N-2,3-dihydroxypropyl) ethylenediamine-N,N'-diacetate (EDTA-LDP); including those described in U.S. Pat. No. 5,312,617, the disclosure of which is hereby incorporated herein by reference in its entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred. Suitable complexes therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, more preferably Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast agent to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled vesicles of the present invention are ideal for attaining the goals of slowed rotational correlation times and resultant improvement in relaxivity. Although not intending to be bound by any particular theory of operation, it is contemplated that since the nitroxides may be designed to coat the perimeters of the vesicles, for example, by making alkyl derivatives thereof, the resulting correlation times can be optimized. Moreover, the resulting contrast medium of the present invention may be viewed as a magnetic sphere, a geometric configuration which maximizes relaxivity.

Exemplary superparamagnetic contrast agents suitable for use with MRI in the compositions of the present invention include metal oxides and sulfides which experience a magnetic domain, ferro- or ferrimagnetic compounds, such as pure iron, magnetic iron oxide, such as magnetite, γ-$Fe_2O_3$, $Fe_3O_4$, manganese ferrite, cobalt ferrite and nickel ferrite. Paramagnetic gases can also be employed in the present compositions, such as oxygen 17 gas ($^{17}O_2$). In addition, hyperpolarized xenon, neon, or helium gas may also be employed. Magnetic resonance (MR) whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the lipid and/or vesicle compositions. In the case of vesicle compositions, the aforementioned contrast agents may be entrapped within the internal void thereof, administered as a solution with the vesicles, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the lipid and/or vesicle compositions of the present invention.

The stabilizing materials and/or vesicles of the present invention may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, for example, particles having diameters of about 100 nm, have much higher R2 relaxivities as compared to R1 relaxivities. The smaller particles, for example, particles having diameters of about 10 to about 15 nm, have somewhat lower R2 relaxivities, but much more balanced R1 and R2 values. Much smaller particles, for example, monocrystalline iron oxide particles having diameters of about 3 to about 5 nm, have lower R2 relaxivities, but probably the most balanced R1 and R2 relaxation rates. Ferritin can also be formulated to encapsulate a core of very high relaxation rate superparamagnetic iron. It has been discovered that the lipid and/or vesicle compositions, including gas filled vesicles, can increase the efficacy and safety of these conventional iron oxide based MRI contrast agents.

The iron oxides may simply be incorporated into the stabilizing materials and/or vesicles. Preferably, in the case of vesicles formulated from lipids, the iron oxides may be incorporated into the walls of the vesicles, for example, by being adsorbed onto the surfaces of the vesicles, or entrapped within the interior of the vesicles as described in U.S. Pat. No. 5,088,499, the disclosure of which is hereby incorporated herein by reference in its entirety.

Without being bound to any particular theory or theories of operation, it is believed that the vesicles of the present invention increase the efficacy of the superparamagnetic contrast agents by several mechanisms. First, it is believed that the vesicles function to increase the apparent magnetic concentration of the iron oxide particles. Also, it is believed that the vesicles increase the apparent rotational correlation time of the MRI contrast agents, including paramagnetic and superparamagnetic agents, so that relaxation rates are increased. In addition, the vesicles appear to increase the apparent magnetic domain of the contrast medium according to the manner described hereinafter.

Certain of the vesicles of the present invention, and especially vesicles formulated from lipids, may be visualized as flexible spherical domains of differing susceptibility from the suspending medium, including, for example, the aqueous suspension of the contrast medium or blood or other body fluids, for example, in the case of intravascular injection or injection into other body locations. In the case of ferrites or iron oxide particles, it should be noted that the contrast provided by these agents is dependent on particle size. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions as a function of the $T_1$ and $T_2$ relaxation times of a spin ½ nucleus with gyromagnetic ratio g perturbed by a paramagnetic ion:

$$1/T_1 M = (2/15)S(S+1)\gamma^2 g^2 \beta^2/r^6 [3\tau_c/(1+\omega_I^2\tau_c^2) +$$
$$7\tau_c/(1+\omega_s^2\tau_c^2)] + (2/3)S(S+1)A^2/h^2[\tau_e/(1+\omega_s 2\tau_e^2)]$$

and $$1/T_2 M = (1/15)S(S+1)\gamma^2 g^2 \beta^2/r^6 [4\tau_c + 3\tau c/(1+\omega_I^2\tau_c^2) +$$
$$13\tau_c/(1+w_s^2\tau_c^2)] + (1/3)S(S+1)A^2/h^2[\tau_e/(1+\omega_s 2\tau_e^2)]$$

where: S is the electron spin quantum number; g is the electronic g factor; β is the Bohr magneton; $\omega_I$ and $\omega_s$ (657 $w_I$) is the Larmor angular precession frequencies for the nuclear spins and electron spins; r is the ion-nucleus distance; A is the hyperfine coupling constant; $\tau_c$ and $\tau_c$ are the correlation times for the dipolar and scalar interactions, respectively; and h is Planck's constant. See, e.g., Solomon, I., *Phys. Rev.*, 99:559 (1955) and Bloembergen, N. *J. Chem. Phys.*, 27:572, 595 (1957), the disclosures of each of which are hereby incorporated herein by reference in their entirety.

A few large particles may have a much greater effect than a larger number of much smaller particles, primarily due to a larger correlation time. If one were to make the iron oxide particles very large however, increased toxicity may result, and the lungs may be embolized or the complement cascade system may be activated. Furthermore, it is believed that the total size of the particle is not as important as the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence for a paramagnetic dipole-dipole interaction. Interpreted literally, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. It has not been possible to achieve this heretofore and it is believed that the benefits have been unrecognized heretofore also. By coating the inner or outer surfaces of the vesicles with the contrast agents, even though the individual contrast agents, for example, iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the vesicle and is maximal at the surface of the vesicle. These agents afford the advantage of flexibility, namely, compliance. While rigid vesicles might lodge in the lungs or other organs and cause toxic reactions, these flexible vesicles slide through the capillaries much more easily.

In contrast to the flexible vesicles described above, it may be desirable, in certain circumstances, to formulate vesicles from substantially impermeable polymeric materials including, for example, polymethyl methacrylate. This would generally result in the formation of vesicles which may be substantially impermeable and relatively inelastic and brittle. In embodiments involving diagnostic imaging, for example, ultrasound, contrast media which comprise such brittle vesicles would generally not provide the desirable reflectivity that the flexible vesicles may provide. However, by increasing the power output on ultrasound, the brittle microspheres can be made to rupture, thereby causing acoustic emissions which can be detected by an ultrasound transducer.

Nuclear Medicine Imaging (NMI) may also be used in connection with the diagnostic and therapeutic method aspects of the present invention. For example, NMI may be used to detect radioactive gases, such as $Xe^{133}$, which may be incorporated in the present compositions in addition to, or instead of, the gases discussed above. Such radioactive gases may be entrapped within vesicles for use in detecting, for example, thrombosis. Preferably, bifunctional chelate derivatives are incorporated in the walls of vesicles, and the resulting vesicles may be employed in both NMI and ultrasound. In this case, high energy, high quality nuclear medicine imaging isotopes, such as $technetium^{99m}$ or $indium^{111}$ can be incorporated in the walls of vesicles. Whole body gamma scanning cameras can then be employed to rapidly localize regions of vesicle uptake in vivo. If desired, ultrasound may also be used to confirm the presence, for example, of a clot within the blood vessels, since ultrasound generally provides improved resolution as compared to nuclear medicine techniques. NMI may also be used to screen the entire body of the patient to detect areas of vascular thrombosis, and ultrasound can be applied to these areas locally to promote rupture of the vesicles and treat the clot.

For optical imaging, optically active gases, such as argon or neon, may be incorporated in the present compositions. In addition, optically active materials, for example, fluorescent materials, including porphyrin derivatives, may also be used. Elastography is an imaging technique which generally employs much lower frequency sound, for example, about 60 kHz, as compared to ultrasound which can involve frequencies of over 1 MHz. In elastography, the sound energy is generally applied to the tissue and the elasticity of the tissue may then be determined. In connection with preferred embodiments of the invention, which involve highly elastic vesicles, the deposition of such vesicles onto, for example, a clot, increases the local elasticity of the tissue and/or the space surrounding the clot. This increased elasticity may then be detected with elastography. If desired, elastography can be used in conjunction with other imaging techniques, such as MRI and ultrasound.

Of course, one skilled in the art would recognize, in view of the foregoing disclosure, that oxygen delivery may be conducted in accordance with the present invention without the use of diagnostic imaging, such as ultrasound or contrast agents.

The present invention also describes apparatus for making and delivering an oxygen delivery agent according to the present invention are shown in FIGS. 3–6. In a preferred embodiment, the apparatus comprises (1) vessels containing separated portions of the stabilizing material and the fluorinated gas/gaseous precursor, (2) one or more mixing devices, (3) a mechanism for evacuating the stabilizing material and fluorinated gas/gaseous precursor from the vessels and for driving them into the mixing device(s), so as to permit the formation of a mixture of stabilizing material and fluorinated gas/gaseous precursor, and (4) a device for introducing oxygen into the mixture so as to form an oxygen delivery agent. Optionally, the apparatus may also include (1) a conduit for transporting the oxygen delivery agent to the patient, (2) a filter assembly for sizing the agent, and/or (3) a heating element for raising the temperature of the agent to at least about body temperature, especially if the fluorinated compound is a gaseous precursor, since heating will cause the gaseous precursor to convert to a gas prior to administration to the patient.

Figure 3:
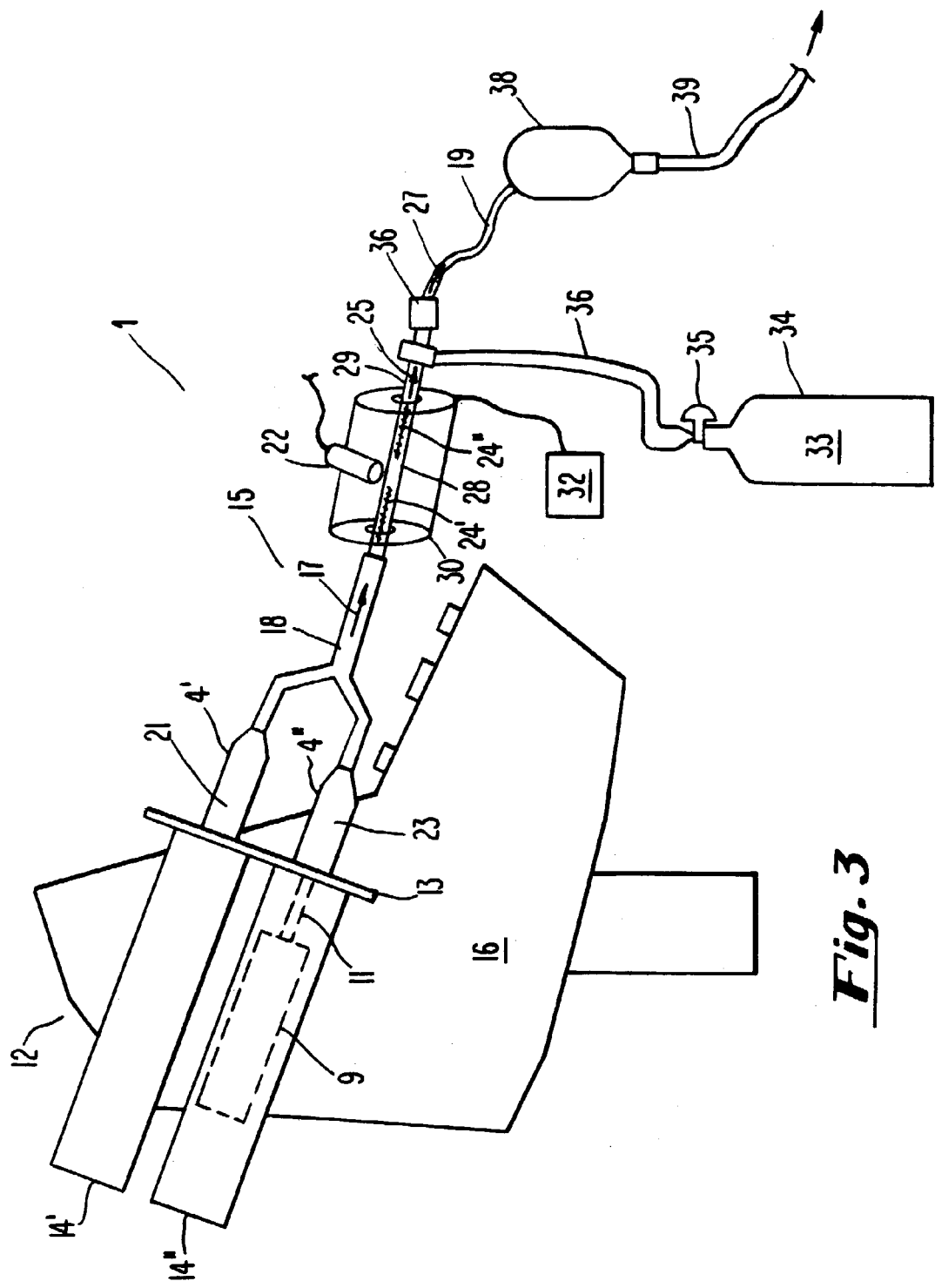
FIG. 3 is a diagram, partially schematic, of a first embodiment of an apparatus for making an oxygen delivery agent according to the current invention.

FIG. 3 shows one embodiment of an apparatus 1 for making and delivering an oxygen delivery agent according to the current invention. In this embodiment, the vessels for containing separated portions of the stabilizing material 21 and the fluorinated gas/gaseous precursor 23 comprise a pair of syringes 4' and 4", respectively. The evacuating mechanism comprises a mechanical injection device 12. The mechanical injection device 12 comprises a pair of piston drivers 14 and a controller 16. Each piston driver 14 includes a driver 9, such as a hydraulic or pneumatic cylinder or an electric motor, and a piston or shaft 11. The piston drivers 14 are secured to a mounting plate 13, along with the syringes 4' and 4". In operation, the pistons 11 drive the plungers (not shown) of the syringes, thereby causing pressurization and subsequent evacuation of the contents of the syringes. According to this embodiment, the stabilizing material 21, for example a aqueous solution containing lipids as previously discussed, is contained with the first syringe 4' while the fluorinated gas or gaseous precursor 23, for example a perfluorocarbon gas/gaseous precursor as also previously discussed, is contained with the second syringe 4".

The controller 16, which preferably includes a programmable microprocessor, controls the amount of power supplied to the piston driver 14 and permits regulation of the stroke and rate of travel of the piston 11 and, thereby, the volume and flow rate discharged from the syringes 4' and 4". A suitable mechanical injection device is the Mark V Plus, available from Medrad Inc. of Pittsburgh, Pa. Other injection devices include the Syringe Pump Model 351, available from Sage Instruments (a division of Orion Research Inc.) of Boston, Mass., and the Liebel Flarsheim, available from Liebel Flarsheim Co. of Cincinnati, Ohio.

A section of Y-shaped tubing 18 has branches that are connected to each of the syringes 4' and 4" and serve as conduits for directing the stabilizing material 21 and fluorinated gas/gaseous precursor 23 to a mixing device 15. In the FIG. 3 embodiment, the mixing device 15 causes mixing to occur in four stages and includes a contacting device, two turbulence inducing devices, and an agitation device. The Y-shaped tubing 18 also serves to bring the stabilizing material 21 and the fluorinated gas/gaseous precursor 23 evacuated from the syringes into mixing contact with each other, forming a mixture 17 of stabilizing material and fluorinated gas/gaseous precursor. This mixing contact forms the first mixing stage.

Figure 3A:
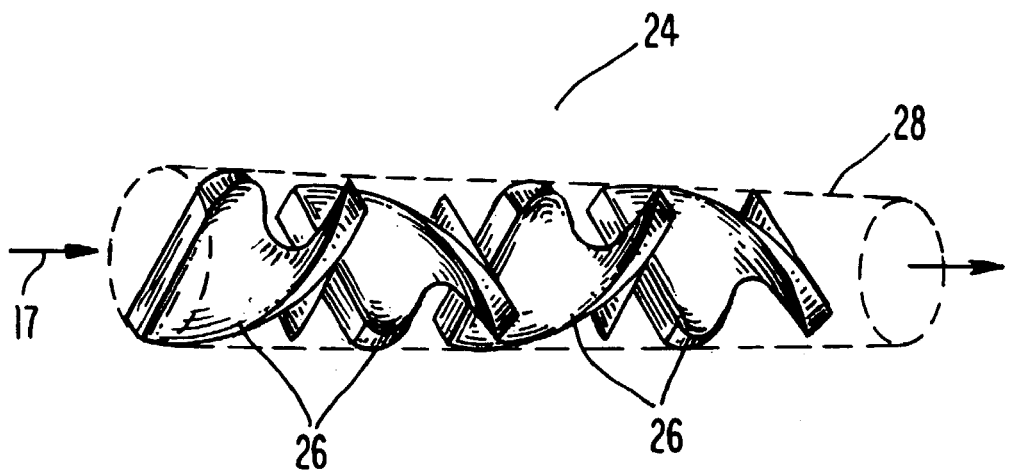
FIG. 3a is a detailed view of the in-line static mixer shown in FIG. 3.

After initial mixing, the tubing 18 directs the mixture 17 to the second mixing stage, formed by the first turbulence inducing device 24'. A second turbulence device 24" forms the fourth mixing stage. Preferably, the turbulence inducing devices 24 are of the static type, and most preferably are a pair of in-line static mixers, such as those described in Maa and Hsu, *J. Microencapsulation,* 13:419–433 (1996), the disclosure of which is hereby incorporated by reference herein in its entirety. A preferred embodiment of one of the in-line static mixers 24 is shown in detail in FIG. 3a. The static mixer 24 comprises a series of baffle elements 26 enclosed within a tube 28. Each baffle element 26 forms a segment of a helix that turns 180° from its inlet to its outlet edge. Further, the inlet of each baffle element 26 is rotationally displaced 90° from the outlet of the adjacent, upstream baffle element and turns in the opposite direction. Thus, a first, right hand helical baffle element is followed by a second, left hand helical baffle element having an inlet edge that is offset 90° with respect to the outlet edge of the first baffle element. The second helical baffle element is, in turn, followed by a third, right hand helical baffle element having an inlet edge that is offset 90° with respect to the outlet edge of the second baffle element, etc. As a result of this arrangement, the fluid flowing through the static mixer 24 undergoes repeated, abrupt changes in direction, creating turbulence and vigorous mixing. Suitable static in-line mixers 24 are available from Cole Parmer of Vernon Hill, Ill. The size and number of helical baffle elements may be selected using the principles discussed in Maa et al. in order to obtain oxygen delivery agents, such as vesicles, of the desired size.

Optionally, a heating device may be incorporated into the apparatus 1. In the embodiment shown in FIG. 3, the heating device comprises a blanket 30 containing electrical resistance heating elements adjusted by a controller 32. As shown in FIG. 3, preferably, the blanket 30 is wrapped around the tubing 28 that encloses the in-line static mixers 24. However, the heating device could be incorporated at other locations on the apparatus as well. Preferably, the heating device is capable of heating the oxygen delivery agent to close to body temperature, e.g., about 37° C. If a gaseous precursor is utilized, the heating device can be used to convert the gaseous precursor to a gas prior to administration to the patient. Accordingly, the heating device can heat the oxygen delivery agent up to about 80° C. or whatever temperature is necessary to convert any particular gaseous precursor to a gas, as can readily be determined by the skilled artisan in view of the present disclosure. Although a heating blanket is shown in FIG. 3, other types of heating devices, such as fluid heating jackets or immersion heaters could also be utilized. In addition, an ultrasonic pressure wave generating device, discussed below in connection with the mixing device, generates energy that can also effect the desired heating.

The agitation device forms the third mixing stage and comprises a device 22 capable of generating high frequency pressure waves, preferably in the ultrasonic frequency range. As used herein, "ultrasonic" refers to frequencies above the range of human hearing. Application of high frequency pressure waves causes mixing to occur by "sonication." The pressure wave generating device 22 is preferably a transducer that converts electrical energy into acoustic energy. As is well known in the art, ultrasonic transducers may be constructed from piezoelectric elements formed from a variety of materials, such as PZT or zirconate. Suitable transducers are available from Panametrics, of Waltham, Mass.

The ultrasonic transducer 22 can be mounted adjacent the mixture flow path, for example in the heating blanket 30 between the first and second static mixers 24' and 24", respectively, as shown in FIG. 3. This allows the transducer 22 to direct high frequency pressure waves into the tubing 28, thereby agitating the fluid flowing through the mixer.

Figure 3B:
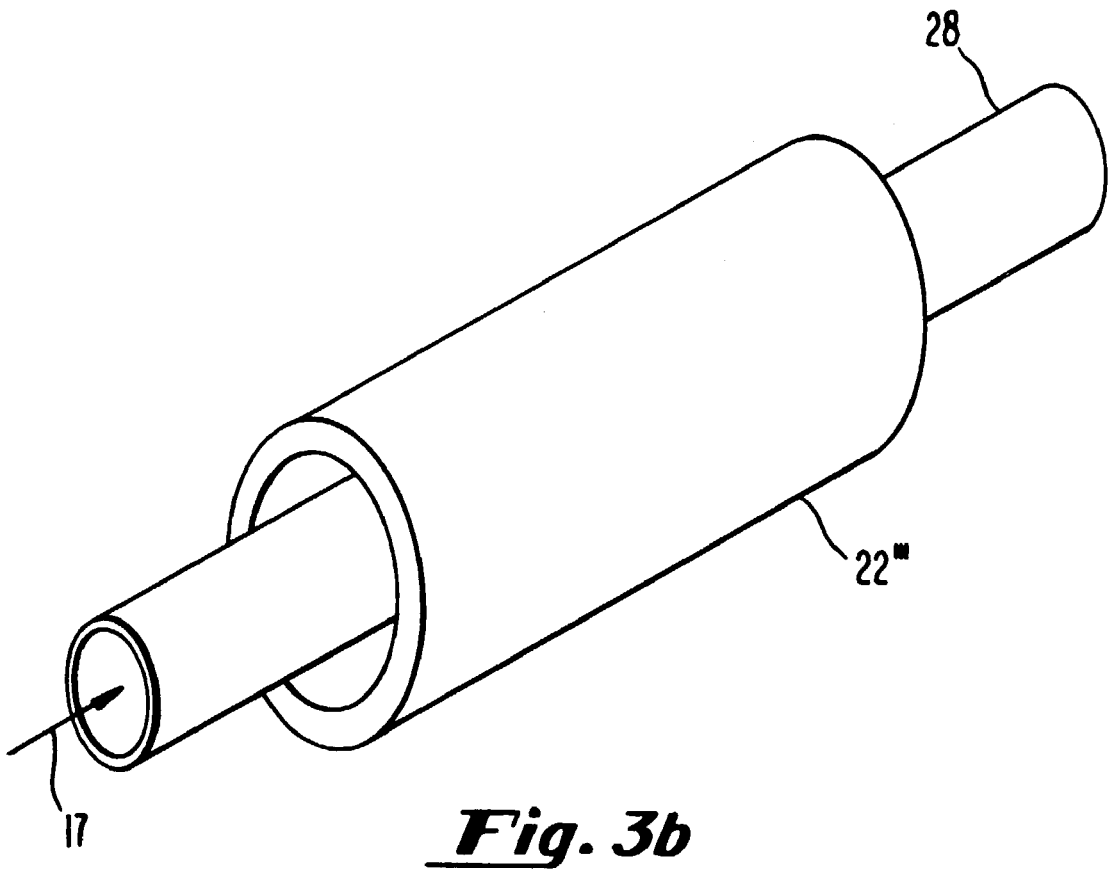
FIG. 3b is an isometric view, partially schematic, of an alternate embodiment of the ultrasonic pressure wave generating device shown in FIG. 3.

FIG. 3b shows an alternate embodiment of the pressure wave generating device, in which an annular transducer 22''' encircles a portion of the conduit through which the mixture 17 flows, for example by encircling the tubing 28 that houses the static mixers 24. Such an arrangement permits the effective transmission of ultrasonic energy into the mixture 17 for the period of time it takes the mixture 17 to travel through the section of encircled tubing 28, therefy resulting in a longer duration of exposure.

Subjecting the stabilizing material 21 and gas/gaseous precursor 23 to ultrasonic energy aids in mixing and, if a gaseous precursor is used, it can also aide in the heating necessary to convert the gaseous precursor to a gas prior to administration to the patient. However, the application of ultrasonic energy has other important benefits as well. For example, in the event that the oxygen delivery agent comprises vesicles, ultrasonic energy causes oscillation of such vesicles. This oscillation, in turn, causes partial cavitation that results in the bursting of larger vesicles. Consequently, the application of ultrasonic energy regulates the size of the vesicles so as to result in a smaller average vesicle size, preferably less than 5 μm, and more uniform sizing. The sizing effect of the application of ultrasonic energy may eliminate the necessity for filtering, discussed further below.

The frequency at which the transducer 22 operates is preferably in the ultrasonic frequency range. Preferably, the frequency is approximately in the 20 KHz to 5 MHz range, more preferably in the 100 KHz to 3 MHz range, more preferably still in the 100 KHz to 1 MHz range, and most preferably approximately 100 KHz. The transducer is preferably operated at a power level of about 10 milliwatts to 5 watts, more preferably from about 20 milliwatts to 2 watts, and most preferably from about 100 milliwatts to 1.5 watts. The transducer 22 can be operated in either the pulsed or continuous mode, but is preferably operated in the continuous mode, and may be of either the focused or non-focused type. Preferably, the focal zone of the transducer 22 encompasses the volume of the tubing 28 through which the mixture 17 of stabilizing material and gas/gaseous precursor flows. If the sonication induced mixing occurs in a chamber or vessel, the focal zone of the transducer 22 should encompasses the volume of the chamber or vessel.

Figure 3C:
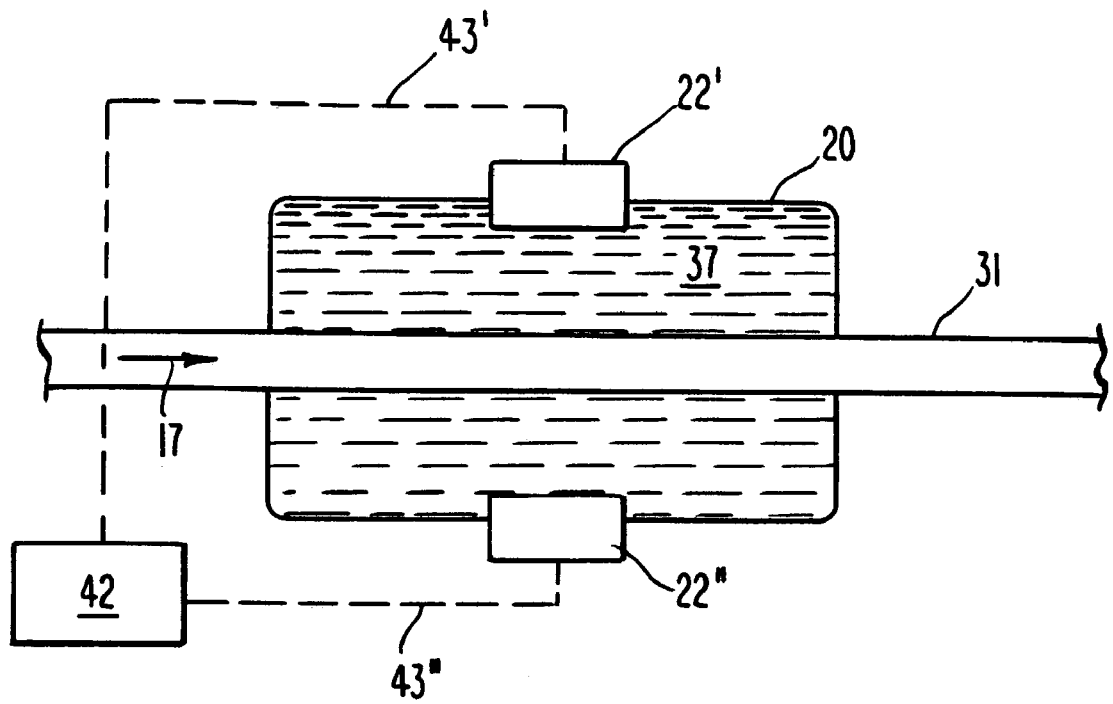
FIGS. 3c and 3d are views, partially schematic, showing two alternate embodiments of the ultrasonic pressure wave generating device shown in FIG. 3.

FIG. 3c shows another embodiment of the transducer arrangement, in which a pair of ultrasonic transducers 22' and 22" are disposed on opposing sides of a chamber 20. The chamber 20 is preferably filled with a medium 37, such as degassed/deionized water or silica gel (sometimes referred to as a "ultrasonic couplant") that facilitates the transmission of ultrasonic energy through the chamber. Tubing 31, through which the mixture 17 of stabilizing material and fluorinated gas/gaseous precursor flows, extends through the insonified chamber 20 so that the mixture is subjected to the ultrasonic energy transmitted by the couplant 37 from the transducers 22' and 22".

Preferably, the temperature of the chamber 20 is controlled to at least about 37° C. so as to facilitate introduction of the oxygen delivery agent into the patient or to further aid in converting the gaseous precursor to a gas prior to administration to the patient. Such temperature control may be effected by a heating blanket, fluid heating jacket, immersion heater, or regulation of the ultrasonic energy. Of course, a higher temperature may be used, depending on the phase transition temperature of the gaseous precursor.

Although a pair of transducers 22' and 22" are shown in FIG. 3c, a single annular transducer, such as transducer 22''' shown in FIG. 3b, could be used to encircle the chamber 20.

As shown in FIG. 3c, the transducers 22' and 22" are preferably regulated by a controller 42, which may be incorporated in the controller 16 of the mechanical injector 12, by means of electrical conduits 43' and 43" that provide control signals from the controller to the transducers. Preferably, the controllers 16 and 42 are integrated or interlinked so that the power output of the transducers depends on the evacuation flow rate set by the mechanical injector 12. Thus, the higher the flow rate, the greater the ultrasonic energy directed to the mixture. In addition, or alternatively, a feedback loop may be provided so that the flow rate set by the injector 12 is regulated based upon the power output of the transducers.

In the FIG. 3c embodiment, more than one transducer is used. In this case, the transducers are preferably constructed and/or controlled so that they operate at different frequencies. Thus, if two transducers are used, one should operate at a higher frequency than the other transducer. Preferably, the first transducer should operate at a frequency that is an integer multiple, for example double, of the frequency at which the second transducer operates. For example, the first transducer operates at 100 KHz and second operates at 200 KHz, or the first operates at 0.5 MHz and the second operates at 1.0 MHz. Preferably, the focal zones of such transducers overlap. In this manner, a harmonic superposition effect is created that enhances mixing.

Figure 3D:
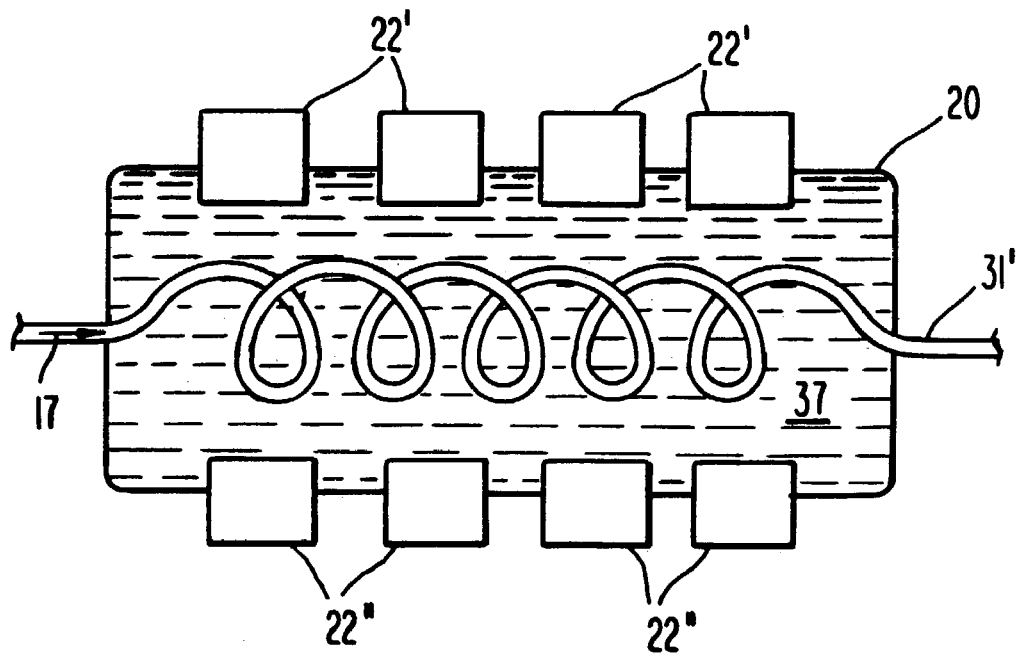

FIG. 3d shows yet another transducer arrangement. In this embodiment, a plurality of opposing pairs of transducers 22' and 22", for example four pairs, are spaced along the chamber 20. In addition, the portion of the tubing 31' that extends through the chamber 20 is coiled so as to maximize the exposure of the mixture 17 to ultrasonic energy. Preferably, the operating frequency of each of the transducers depends on their position along the chamber 20. Most preferably, the frequency is increased from the inlet side to the outlet side of the chamber 20. For example, the left-most transducer pair shown in FIG. 3d may be operated at 100 to 500 Hz, while the right-most pair may be operated at 5 MHz, with intermediate pairs being operated at intermediate, but progressively increasing, frequencies.

The four stages of mixing created by the successive flow of the stabilizing material and fluorinated gas/gaseous precursor mixture through the Y-shaped tubing 18, the first in-line static mixer 24', the agitation device 22, and the second in-line static mixer 24" create vigorous mixing to ensure efficient generation of the oxygen delivery agent.

While the mixing device 15 discussed above is preferred, other types of mixing devices could also be utilized, such as mechanical shakers (e.g., a Wig-L-Bug@, available from Crescent Dental Manufacturing, Inc., 7750 West 47th Street, Lyons, Ill. 60534, or a Capmix, sold by Espe Fabrik Pharmazeutischer Praeparate GMBH & Co., Seefeld, Oberay Germany).

As a result of the mixing produced by the mixing device 15, the stabilizing material 21 and the fluorinated gas/gaseous precursor 23 form a composition 25 capable of receiving and delivering oxygen according to the current invention. For example, if the stabilizing material comprises a aqueous solution containing lipids, and this solution is mixed with a fluorinated gas, the composition 25 discharged from the mixing device 15 will be a solution containing vesicles filled with a fluorinated gas.

The oxygen delivery agent 25 produced by the mixing can be administered directly to the patient, permitting the incorporation of oxygen by the patient's own respiratory processes upon circulation through the patient's lungs. However, oxygen is preferably incorporated into the agent prior to administration, so as to form an oxygen carrying oxygen delivery agent. Accordingly, as shown in FIG. 3, tubing 29 is preferably employed to direct the oxygen delivery agent 25 from the mixing device 15 to the next stage of processing. In the embodiment shown in FIG. 3, tubing 36 connects a supply of oxygen 33, such as from a pressurized cylinder 34, to tubing 29. Opening a valve 35 allows oxygen 33 to mix with the composition 25 flowing through the tubing 29, thereby allowing the oxygen to be introduced into the composition so as to form an oxygen carrying oxygen delivery agent 27. Thus, for example, if the composition from the mixing device 15 comprises fluorinated gas filled vesicles in an aqueous solution, as previously discussed, the oxygen 33 will permeate the walls of the vesicles to form vesicles filled with both fluorinated gas and oxygen.

Alternatively, the oxygen cylinder 34 may be dispensed with and oxygen 33 incorporated into the headspace above the gas/gaseous precursor in syringe 4", as discussed further below in connection with the FIG. 4 embodiment. In this case, the formation of the composition 25 and the introduction of the oxygen 33 to form the oxygen carrying oxygen delivery agent 27 both occur within the mixing device 15.

After the incorporation of the oxygen, the tubing 19 preferably directs the oxygen laden delivery agent 27 to a patient. Preferably, a filter assembly 36, which may comprise a cascaded or stacked set of filters, such as a 10 μm filter followed by an 8 μm filter, is incorporated into tubing 19 in order to size the oxygen delivery agent. From the filter assembly 36, the oxygen delivery agent 27 is preferably directed to a conventional IV bag 38 and thence, via tubing 39, to the patient for introduction into the blood stream, for example, by use of a needle. By programming the controller 16 of the mechanical injection device 12, the rate at which the oxygen carrying oxygen delivery agent 27 is made, and the amount and rate delivered to the patient, can be accurately and variably regulated. Note that although the filter 36 is shown as being located in tubing 19 just upstream of the IV bag 38, the filter could also be located at other locations along the conduits forming the flow path.

FIG. 4 shows another embodiment of an apparatus 1' of the current invention. The FIG. 4 embodiment is similar to the embodiment shown in FIG. 3 except that the vessels for containing the separated portions of stabilizing material 21 and fluorinated gas/gaseous precursor 23 comprise a single syringe 4, which is coupled to the mechanical injection device 12 as before. As shown best in FIG. 4a the barrel 5 of the syringe 4 contains a flexible bag 6 containing the fluorinated gas/gaseous precursor 23. Thus, the bag 6, which is preferably formed from a plastic, forms a second vessel disposed within a first vessel. The syringe barrel 5 also contains the stabilizing material 21, such as an aqueous lipid solution, which preferably surrounds the bag 6.

The bag 6 is preferably only partially filled with the gas/gaseous precursor 23 so as to form a head space 10 above the gas/gaseous precursor into which oxygen 33 is incorporated. The bag 6 is preferably constructed so as to preferentially rupture in a localized area when subjected to pressure. Preferably, this is accomplishing by incorporating into the bag 6 an area 7 that has been weakened—for example, by thinning, scoring, perforating, or otherwise weakening the bag material. The weakened area 7 permits the controlled release of the contents of the bag 6 when pressurized, as discussed further below. Alternatively, a needle or similar member could be incorporated into the syringe 4 so that the actuation of the plunger 15 caused the bag 6 to be pierced.

In use, the mechanical injector 12 urges the plunger 15 of the syringe 4 into the barrel 5, thereby pressurizing the stabilizing material 21. This pressurization, in turn, causes the bag 6 to rupture at the weakened area 7. As a consequence, the stabilizing material 21, the fluorinated gas/gaseous precursor 23, and the oxygen 33 are all intermixed while being ejected from the syringe 4. The contents of the syringe 4 are then directed by tubing 40 to a mixing device 15 as before.

Alternatively, the oxygen 33 could be supplied into the tubing 29 via the supply cylinder 34, as previously discussed in connection with FIG. 3, rather than in the headspace 10 of the bag 6. In this case, the mixing of the stabilizing material 21 and the fluorinated gas/gaseous precursor 23 occurs separately from, and prior to, the introduction of the oxygen 33.

In another alternative, the stabilizing material 21 can be incorporated into the bag 6, and then enclosed within a syringe barrel 5 containing the fluorinated gas/gaseous precursor 23, which surrounds the bag.

Figure 5:
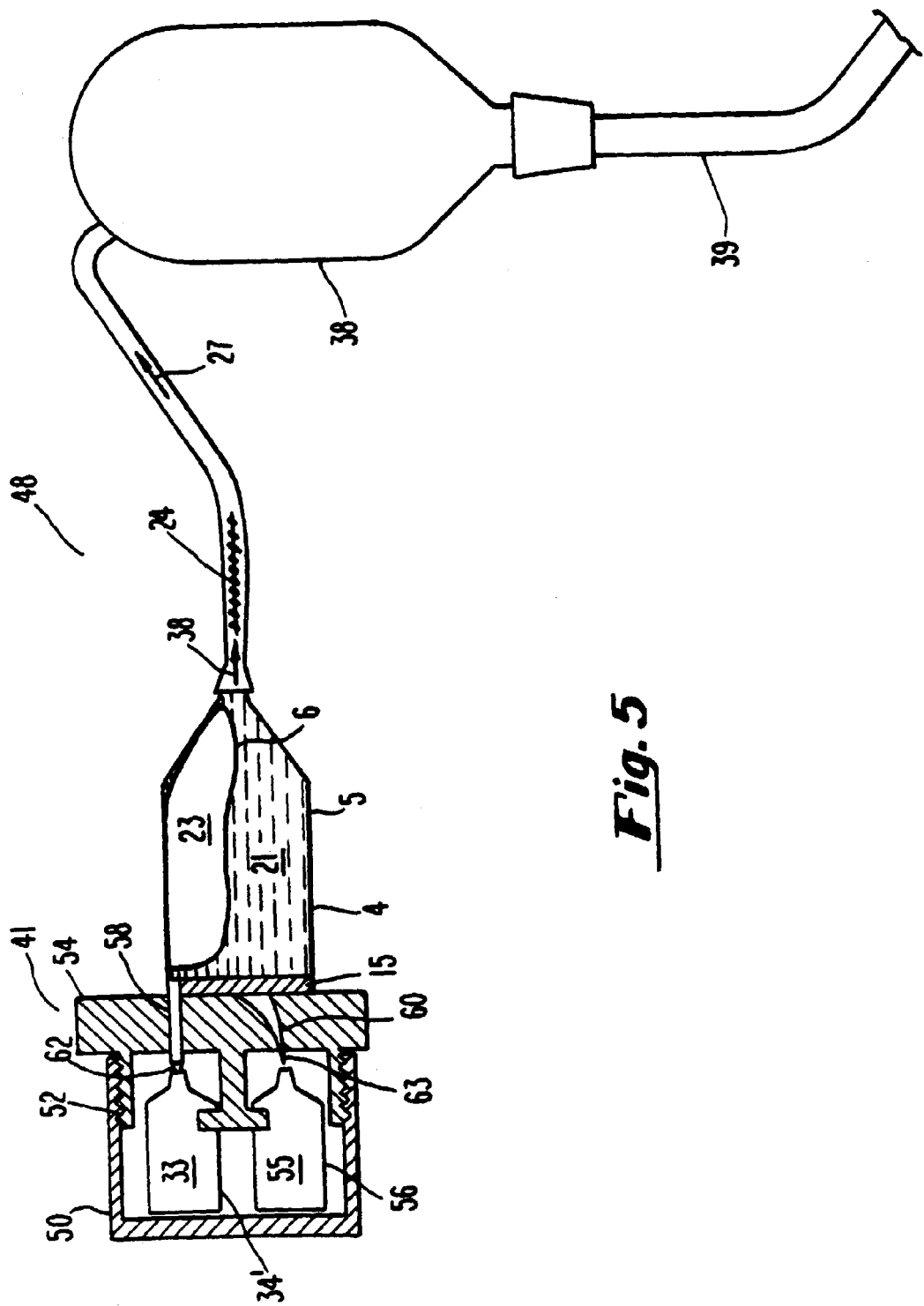
FIG. 5 is a diagram, partially schematic, of third embodiment of the apparatus of the current invention that is especially suitable for mobile use.

FIG. 5 shows another embodiment of the apparatus 48 of the current invention that is especially adapted for mobility, such as for use by emergency response paramedics or in a mobile army surgical hospital (MASH). In this embodiment, the mechanical injector 41 comprises a plate 54 onto which the syringe 4 is mounted. The syringe 4 contains the stabilizing material 21 and the weakened bag 6 contains the fluorinated gas/gaseous precursor 23, as discussed above.

A cap 50 is also mounted, via a threaded joint 52, onto the plate 54. A small, disposal pressurized oxygen cylinder 34' and a cylinder 56 containing a pressurized gas 55, such as carbon dioxide, are enclosed within the cap 50. A tube 58 is mounted within the plate 54. A needle 62 is mounted on one end of the tube 58. The tube 58 forms a passage that extends from the needle 62, through the plate 54 and the plunger 15 of the syringe 4, to the interior of the syringe barrel 5. A second tube 60, on which a second needle 63 is mounted, extends through the plate 54, forming a passage from the needle to the rear face of the plunger 15. Preferably, the needle 62 projects rearwardly slightly further than the needle 63.

Operation of the apparatus is initiated by rotation of the cap 50 so as to tighten it onto the plate 54. The forward motion of the cap 50 drives the needle 62 into the cylinder 34', whose subsequent penetration causes the evacuation of the pressurized oxygen 33. The tube 58 directs the oxygen 33 from the cylinder 34' into the barrel 5 of the syringe 4, where it mixes with the stabilizing material 21. Continued rotation of the cap 50 subsequently drives the second cylinder 56 into the needle 63, causing evacuation of the pressurized gas 55. The gas 55 is directed to the rear face of the plunger 15 by the tube 60, so that the gas drives the plunger forward, thereby pressurizing the contents of the barrel 5. As a result of this pressurization, the bag 6 ruptures, releasing the fluorinated gas/gaseous precursor 23 into the mixture of the oxygen 33 and the stabilizing material 23. Moreover, movement of the plunger 15 also ejects the stabilizing material/fluorinated compound/oxygen mixture 38 from the syringe 4 and drives it through a mixing device, such as an in-line static mixer 24 as previously discussed, so as to form an oxygen carrying oxygen delivery agent 27 according to the current invention. The agent 27 is then directed to the patient, as before.

Figure 6:
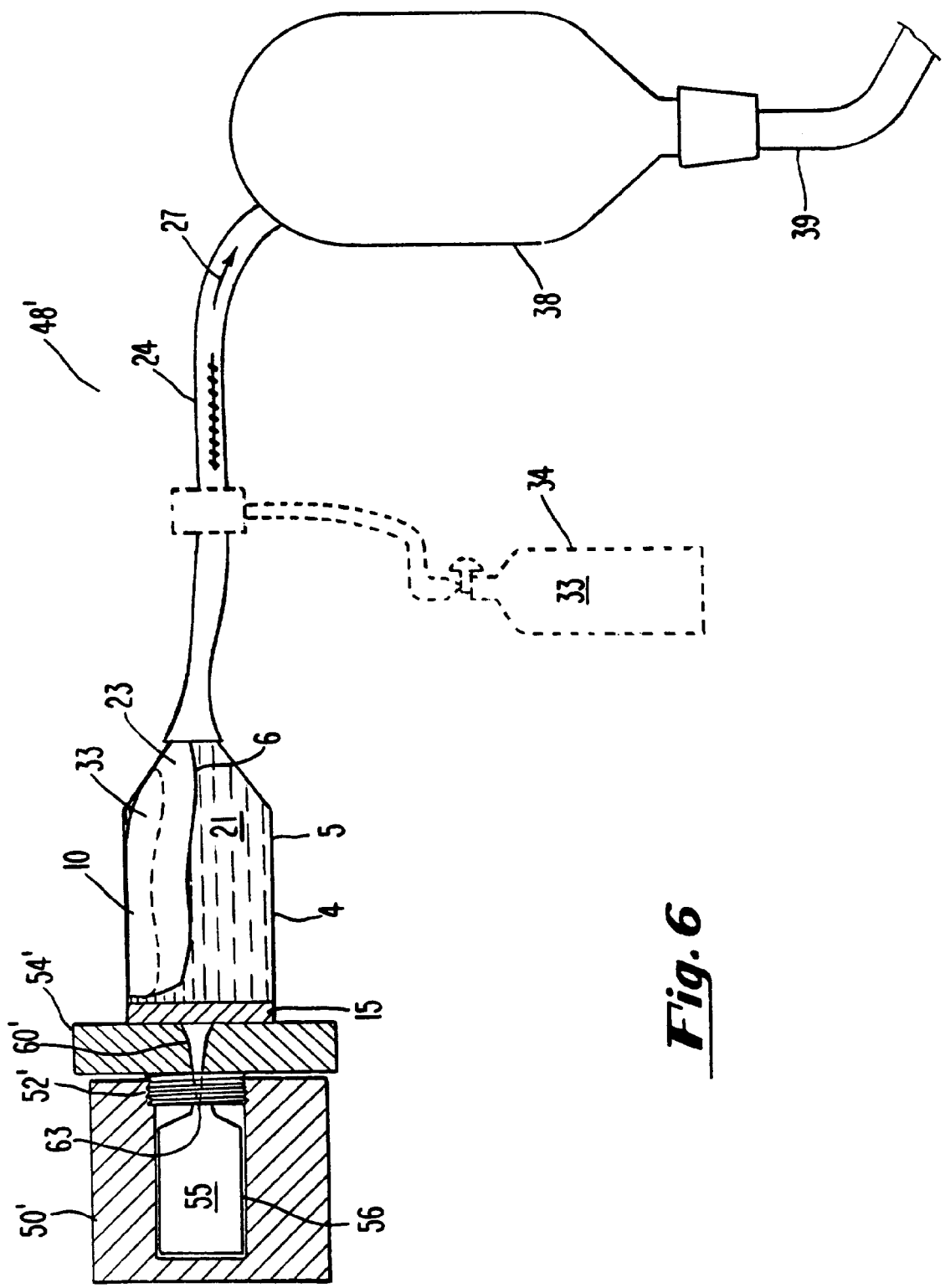
FIG. 6 is a diagram, partially schematic, of a fourth embodiment of the apparatus of the current invention that is especially suitable for mobile use.

Another embodiment of a mobile apparatus 48' according to the current invention is shown in FIG. 6. In this embodiment, the disposable pressurized oxygen cylinder 34' has been dispensed with. Pressurization and evacuation of the barrel 5 of the syringe 4 are accomplished by rotating the cap 50' on a threaded joint 52', thereby impaling the cylinder 56 containing pressurized gas 55, as discussed above. The pressurized gas 55 is directed by a passage 60' to the plunger 15, as also discussed above. Operation of the plunger 15 pressurizes the barrel 5, which causes rupture of the bag 6 and evacuation of the syringe 4, as also discussed above. However, in this embodiment, oxygen 33 has been incorporated into the headspace 10 in the bag 6, as previously discussed in connection with the embodiment shown in FIG. 4. Using this approach, the mixing of the stabilizing material 23, fluorinated gas/gaseous precursor 23, and oxygen 33 will begin simultaneously in the syringe 4 and be subsequently completed in the static in-line mixer 24.

Alternatively, the embodiment of FIG. 6 could be practiced by introducing oxygen 33 from a cylinder 34 connected to the downstream tubing, as previously discussed in connection with the embodiment shown in FIG. 3 and shown in phantom in FIG. 6, rather than being introduced within the syringe barrel 5. In this embodiment, the stabilizing material 21 and the gas/gaseous precursor 23 are mixed prior to the introduction of the oxygen 33. In yet another alternative embodiment, FIG. 6 apparatus could be constructed without any oxygen introducing device, permitting the incorporation of oxygen in vivo.

In all the embodiments shown in FIGS. 3–6, whenever a fluorinated gaseous precursor is used, the gaseous precursor is perferably converted to a gas before it is administered to the patient, as described in detail throughout the present disclosure.

EXAMPLES

The invention is further demonstrated in the following examples. Examples 1–3 and 5 are actual examples. Examples 4 and 6–10 are prophetic examples. The examples are for purposes of illustration of the present invention only, and are not intended to limit the scope thereof.

Example 1

Preparation of Gas Filled Vesicles

To prepare gas filled vesicles, a 5 ml solution of a lipid mixture (5 mg/ml) containing 87 mole % dipalmitoylphosphatidylcholine (DPPC), 8 mole % dipalmitoyl-phosphatidylethanolamine-polyethylene glycol-5000 (DPPE-PEG-5000), 5 mole % dipalmitoylphosphatidic acid (DPPA) (all supplied by Avanti Polar Lipids, Alabaster, Ala.) in 8:1:1:1 normal saline:glycerol:propylene glycol solution, was placed in a 15.8 ml glass bottle with a rubber stopper. Air was evacuated from the bottle using a vacuum pump (Model Welch 2-Stage DirecTorr Pump, VWR Scientific, Cerritos, Calif.) by connecting the hose to the bottle through an 18 gauge needle perforating the rubber stopper. After removing the air, perfluorobutane (Pfaltz and Bauer, Waterbury, Conn.) was placed in the stoppered bottle via another 18 gauge needle connected to tubing attached to a canister of perfluorobutane. This process was repeated 5 times so that any traces of air were removed from the stoppered bottle and the space above the lipid solution was completely filled with perfluorobutane. The pressure inside the glass bottle was equilibrated to ambient pressure by allowing the 18 gauge needle to vent for a moment or two before removing the needle from the stopper.

After filling the bottle with perfluorobutane the bottle was secured to the arms of a Wig-L-Bug™ (Crescent Dental Mfg. Co., Lyons, Ill.) using rubber bands to fasten the bottle. The bottle was then shaken by the Wig-L-Bug™ for 60 seconds. A frothy suspension of foam resulted, and it took several minutes for any appreciable separation of the foam layer from the clear solution at the bottom. After shaking, the volume of the material increased from 5 cc to about 12 cc, suggesting that the liposomes entrapped about 7 cc of the perfluorobutane.

The material was sized using an Accusizer (Model 770, Particle Sizing System, Santa Barbara, Calif.) and also examined by a polarizing light microscope (Nikon TMS, Nikon) at 150× magnification. The liposomes appeared as rather large spherical structures with a mean diameter of about 20–50 µm. A portion of the liposomes were then injected via a syringe through a Costar filter (Syrfil 800938, Costar, Pleasanton, Calif.) with a pore sizes of 8 µm. The liposomes were again examined via light microscopy and the Accusizer System. The mean diameter of the liposomes was about 3 µm and the volume weighted mean was about 7 µm. Greater than 99.9% of the liposomes were under 11 µm in diameter.

Example 2

Methods of Sizing Gas Filled Vesicles

The first method for sizing gas filled vesicles is applicable with diluents with different gas compositions, for example air-saturated saline, nitrogen-saturated saline or degassed saline. A mechanical diffusion pump is throttled to achieve various gas concentrations in the solutions. The level of oxygen is detected with an oxygen sensitive electrode. The "collect data" feature on an optical particle sizer is used with dilute solutions, otherwise the "autodilute" function is used. The accuracy of the particle count is a function of concentration and is more accurate for dilute solutions.

The second method for sizing gas filled microspheres is optical microscopy, which employs an analytical program for averaging several frames of sampling. Size distribution, concentration and statistical analysis of variation can all be determined this way.

A 200 ml lipid solution (i.e., 200 mg of the lipid mixture described in Example 1 in 200 ml normal saline) is flushed with gaseous perfluoropentane for approximately 10 minutes then sealed with a rubber stopper. The flask is shaken on an orbital shaker for one hour at 400 rpm. A 50 µl sample is sized directly without further dilution in an SPOS system 2 accusizer. A representative table of the size data, obtainable by following the above protocol, is shown below.

TABLE 3

| % of Total Particle Number Less than X μm | X μm |
|---|---|
| 5 | 1.03 |
| 10 | 1.08 |
| 15 | 1.14 |
| 20 | 1.18 |
| 25 | 1.24 |
| 30 | 1.29 |
| 35 | 1.35 |
| 40 | 1.40 |
| 45 | 1.46 |
| 50 | 1.54 |
| 55 | 1.63 |
| 60 | 1.77 |
| 65 | 1.98 |
| 70 | 2.29 |
| 75 | 2.74 |
| 80 | 3.35 |
| 85 | 4.01 |
| 90 | 4.66 |
| 95 | 6.21 |

Example 3

In Vivo Administration of Gas Filled Vesicles

Lipid vesicles were prepared following the method in Example 1, except that the gas used was perfluoropropane or a combination of 80% perfluoropropane and 20% air. As would be known to the skilled artisan, air comprises about 21% oxygen, so that 20% air would comprise approximately 4% oxygen.

Ten groups of mice were injected with the lipid vesicles (e.g., the lipid mixture from Example 1) containing perfluoropropane. For Groups 1–5, the lipid vesicles contained 100% perfluoropropane. For Groups 6–10, the lipid vesicles contained 80% perfluoropropane and 20% air.

The deaths of the mice exposed to the lipid vesicles in Groups 1–10 were recorded after one hour. In Groups 1–5, which were exposed to lipid vesicles containing 100% perfluoropropane, only mice receiving over 4.0 cc/kg body weight died. The actual mortality rate was 60% in mice receiving this dose. On the other hand, in Groups 6–10, which were exposed to lipid vesicles containing 80% perfluoropropane and 20% air, all the mice survived doses up to 7.58 cc/kg body weight. The results are shown in the tables below.

TABLE 4

100% Perfluoropropane Filled Vesicles

| weight (kg) | dose (cc) | dose (cc)/kg | response | Group |
|---|---|---|---|---|
| 36 | 0.05 | 1.39 | 1 | 1 |
| 36 | 0.05 | 1.39 | 1 | 1 |
| 36 | 0.05 | 1.39 | 1 | 1 |
| 33 | 0.05 | 1.52 | 1 | 1 |
| 38 | 0.1 | 2.63 | 1 | 2 |
| 35 | 0.1 | 2.86 | 1 | 2 |
| 35 | 0.1 | 2.86 | 1 | 2 |
| 36 | 0.1 | 2.78 | 1 | 2 |
| 36 | 0.15 | 4.17 | 3 | 3 |
| 37 | 0.15 | 4.05 | 3 | 3 |
| 39 | 0.15 | 3.85 | 2 | 3 |
| 36 | 0.15 | 4.17 | 3 | 3 |
| 36 | 0.15 | 4.17 | 3 | 3 |
| 39 | 0.2 | 5.13 | 1 | 4 |
| 38 | 0.2 | 5.26 | 3 | 4 |
| 35 | 0.2 | 5.71 | 3 | 4 |
| 36 | 0.2 | 5.56 | 3 | 4 |

TABLE 4-continued

100% Perfluoropropane Filled Vesicles

| weight (kg) | dose (cc) | dose (cc)/kg | response | Group |
|---|---|---|---|---|
| 38 | 0.25 | 6.58 | 2 | 5 |
| 36 | 0.25 | 6.94 | 1 | 5 |
| 37 | 0.25 | 6.76 | 3 | 5 |
| 36 | 0.25 | 6.94 | 2 | 5 |

Response:
1 = no response
2 = response but survived
3 = death

TABLE 5

80% Perfluoropropane/20% Air Filled Vesicles

| Weight (kg) | Dose (cc) | Dose (cc)/kg | Response | Group |
|---|---|---|---|---|
| 31 | 0.05 | 1.61 | 1 | 6 |
| 35 | 0.05 | 1.43 | 1 | 6 |
| 35 | 0.05 | 1.43 | 1 | 6 |
| 33 | 0.05 | 1.52 | 1 | 6 |
| 35 | 0.05 | 1.43 | 1 | 6 |
| 34 | 0.1 | 2.94 | 1 | 7 |
| 35 | 0.1 | 2.86 | 1 | 7 |
| 35 | 0.1 | 2.86 | 1 | 7 |
| 33 | 0.1 | 3.03 | 1 | 7 |
| 35 | 0.1 | 2.86 | 1 | 7 |
| 38 | 0.15 | 3.95 | 1 | 8 |
| 35 | 0.15 | 4.29 | 1 | 8 |
| 33 | 0.15 | 4.55 | 1 | 8 |
| 37 | 0.15 | 4.05 | 1 | 8 |
| 33 | 0.15 | 4.55 | 1 | 8 |
| 33 | 0.2 | 6.06 | 1 | 9 |
| 35 | 0.2 | 5.71 | 1 | 9 |
| 35 | 0.2 | 5.71 | 1 | 9 |
| 36 | 0.2 | 5.56 | 1 | 9 |
| 37 | 0.2 | 5.41 | 1 | 9 |
| 38 | 0.25 | 6.58 | 1 | 10 |
| 33 | 0.25 | 7.58 | 1 | 10 |
| 33 | 0.25 | 7.58 | 1 | 10 |
| 36 | 0.25 | 6.94 | 1 | 10 |
| 33 | 0.25 | 7.58 | 1 | 10 |

Response:
1 = no response
2 = response but survived
3 = death

Example 4

Comparison of Oxygen Concentrations

The gas headspace was removed from 8 lipid mixture samples (i.e., DPPC+DPPA+DPPE-PEG-5,000, as described in Example 1) using a Sargent-Welch vacuum pump (Skokie, Ill.). The headspace in 4 samples was replaced with 100% oxygen. The headspace in the other 4 samples was replaced with 1.8 ml of $O_2$ and 0.4 ml of perfluorobutane (PFB), which is the equivalent of 80% $O_2$ and 20% perfluorobutane (PFB). A YSI model 55 oxygen meter (Yellow Springs Instrument, inc., Yellow Springs, Ohio) was used to establish the oxygen concentration in a beaker of normal saline at 37° C. To maintain a constant temperature, the beaker was placed in an evaporating dish full of 37° C. water. The saline was stirred throughout the experiment. After the concentration of $O_2$ in the saline had stabilized, 1 cc of each of the samples was added to 150 ml of normal saline and the peak oxygen concentration was measured. The data is shown in the table below. The values in the table are differences of oxygen concentrations determined by subtracting initial oxygen levels from peak oxygen levels. The peak oxygen concentration occurs after the stabilizing materials comprising the fluorinated gas have dissolved/imbibed as much oxygen as possible from the saline.

TABLE 6

Difference From Initial Oxygen Concentration in Saline Caused by Uptake of Oxygen From the Addition of the Gas Filled Stabilizing Material

| | Stabilizing Material comprising 80% $O_2$ & 20% PFB | Stabilizing Material comprising 100% $O_2$ |
|---|---|---|
| First Sampling | 0.17 mg/ml | 0.11 mg/ml |
| Second Sampling | 0.22 mg/ml | 0.11 mg/ml |
| Third Sampling | 0.24 mg/ml | 0.13 mg/ml |
| Mean | 0.21 mg/ml | 0.12 mg/ml |
| Standard Deviation | 0.04 mg/ml | 0.01 mg/ml |

A one-way ANOVA was carried out using the JMP 3.1.5 statistical package for the Macintosh (SAS Institute, Cary, N.C.). This analysis showed that the 80% $O_2$/20% perfluorobutane (PFB) lipid mixture was significantly different from the 100% $O_2$ lipid mixture with a p value less than 0.0130. The results in the table demonstrate that the stabilizing material comprising 80% oxygen and 20% perfluorobutane takes up almost two times more oxygen from the medium than the stabilizing material comprising 100% oxygen.

Example 5

Oxygen Saturation

Anesthetized rats are immobilized and 25 g needles are placed in each tail vein. One needle is connected to a peristaltic pump and heparinized normal saline (100 μl heparin in 100 ml saline) is introduced at a rate of 0.5 ml/minute. The other needle is used to drain blood at approximately the same rate. An oxygen meter is used to measure the expired oxygen in a plastic vial placed over the rat's head. Samples are collected at 2 minute intervals in capillary tubes and the hematocrit is obtained. When the hematocrit drops from 40% to 10%, the oxygen saturation in the expirations drops accordingly. At this point the peristaltic pump is switched to pumping a lipid mixture (e.g., DPPC+DPPA+DPPE-5000 PEG, as described in Example 1) with a gas comprising 80% perfluorobutane and 20% oxygen. The oxygen saturation is measured as the lipid mixture enters and is seen to increase as the proportion of the lipid mixture to saline increases. This experiment demonstrates that the oxygen dissolving/carrying capacity of the perfluorocarbon filled vesicles operates in vivo as well as in vitro, as in Example 4.

Example 6

Emergency Applications

A soldier is hemorrhaging massively from a bomb accident which occurs in a steamy jungle far from base headquarters. Portable tanks of oxygen and perfluoropentane are injected into the injection chamber and phospholipids in an isotonic saline solution are mixed vigorously at 37° C. with the gases to produce perfluoropentane and oxygen gas filled microspheres. The material is injected into the soldier as a bolus using an apparatus shown in FIG. 5 or FIG. 6 and described herein, followed by a sustained drip infusion until the soldier's volume status and oxygenation improve. The soldier receives a total of about 2 liters of material over a period of about an hour. The soldier is finally evacuated by air-lift and survives the massive hemorrhage because of the transfusion therapy.

Example 7

Radiation Therapy Applications

A patient with a hypoxic tumor from metastatic malignant melanoma prepares to undergo radiation therapy. The patient is injected with oxygen and perfluorocarbon gas filled microspheres, as described in Example 6, and radiotherapy is carried out. An improved response to radiation is observed because of the oxygen delivery to the tissue.

Example 8

Radiotherapy Applications

Gas filled vesicles are prepared as in Example 6, except that the vesicles are prepared with relatively impermeable cross-linked lipid materials (such as, for example, cyanomethacrylate cross-linked to polyglutamate). A patient with a hypoxic tumor from metastatic malignant melanoma undergoes radiation therapy. The patient is injected with oxygen and perfluoroethane filled microspheres during radiation therapy. Thereafter, high energy ultrasound is applied to the tumor with a focused transducer at 1 MHz, 1 watt/cm$^2$ with a 20% duty cycle which will result in intratumoral microsphere rupture and the local delivery of oxygen to the tumor. Radiotherapy is performed concomitantly or shortly after this procedure to obtain improved tumor regression.

Example 9

Surgical Applications

A power injector fitted with a static mixer (Cole-Parmer Instrument Co., Vernon Hills, Ill.), as shown in FIGS. 3, 5 and 6 and described herein, injects 1000 ccs of perfluorobutane and oxygen gas filled microspheres into the antecubital vein of a patient undergoing coronary artery bypass graft surgery. Because of this treatment, improved oxygen delivery is obtained in the patient's myocardial and cerebral tissues.

The disclosure of each patent, patent application and publication cited or described in this document is hereby incorporated by reference herein in its entirety.

Various modifications of the invention, in addition to those described herein, will be apparent to one skilled in the art from the foregoing description. Such modifications are also intended to fall within the spirit and scope of the appended claims.

What is claimed is:

1. A method of delivering oxygen to a patient comprising administering to the patient a composition which comprises a fluorinated gas, oxygen, and a stabilizing material, wherein:

(a) the fluorinated gas is selected from the group consisting of bromotrifluoroethane, chlorotrifluoromethane, dichlorodifluoromethane, dibromofluoromethane, chloropentafluoroethane, bromochlorodifluoromethane, dichloro-1,1,2,2-tetrafluoroethane, hexafluoroethane, perfluoromethane, perfluoroethane, perfluoropropylene, perfluoro-2-butyne, perfluoro-2-butene, perfluorobuta-1,3-diene, perfluoro n-propyl ethyl ether, perflouro diethyl ether, perfluoro methyl ethyl ether, perfluoro dimethyl ether, sulfur hexafluoride, selenium hexafluoride and perfluoropropionyl chloride; and (b) the fluorinated gas in the composition is present in an amount of about 15% to about 85% of the total amount of gas in the composition and the oxygen is present in an amount of about 85% to about 15% of the total amount of gas in the composition.

2. The method of claim 1, further comprising imaging the patient with diagnostic ultrasound to monitor the location of the composition.

3. The method of claim 2, further comprising applying therapeutic ultrasound to the patient to facilitate delivery of oxygen in a desired region of the patient.

4. The method of claim 1, wherein the composition further comprises an aqueous carrier.

5. The method of claim 1, wherein the oxygen is $O_2$.

6. The method of claim 1, wherein the fluorinated gas in the composition is present in an amount of about 20% to about 80% of the total amount of gas in the composition and the oxygen is present in an amount of about 80% to about 20% of the total amount of gas in the composition.

7. The method of claim 1, wherein the fluorinated gas is selected from the group consisting of perfluoromethane, perfluoroethane, perfluoro n-propyl ethyl ether, perflouro diethyl ether, perfluoro methyl ethyl ether, perfluoro dimethyl ether and sulfur hexafluoride.

8. The method of claim 7, wherein the fluorinated gas is selected from the group consisting of perfluoromethane, and perfluoroethane.

9. The method of claim 1, wherein the fluorinated gas has been converted to a gas from a gaseous precursor.

10. The method of claim 9, wherein the fluorinated gas that has been converted to a gas from a gaseous precursor is selected from the group consisting of 1-bromo-1,1,2,3,3,3-hexafluoropropane, bromoperfluoropropane, 2-chloro-1,1,1,4,4,4-hexafluoro-2-butene, 2-chloropentafluoro-1,3-butadiene, iodotrifluoroethylene, 1,1,2-trifluoro-2-chloroethane, 1,2-difluorochloroethane, 1,1-difluoro-2-chloroethane, 1,1-dichlorofluoroethane, 1-bromoethane, 1-fluorobutane, perfluorotetrahydropyran, perfluoromethyltetrahydrofuran, perfluoro t-butyl methyl ether, perfluoro n-butyl methyl ether, perfluoro isopropyl methyl ether, 1-bromo-nonafluorobutane, 1-chloro-1-fluoro-1-bromomethane, 1,1,1-trichloro-2,2,2-trifluoroethane, 1,2-dichloro-2,2-difluoroethane, 1,1-dichloro-1,2-difluoroethane, 1,2-dichloro-1,1,3-trifluoropropane, 1-bromoperfluorobutane, 1-bromo-2,4-difluorobenzene, 2-iodo-1,1,1-trifluoroethane, 5-bromovaleryl chloride, 1,3-dichlorotetrafluoroacetone, bromine pentafluoride, heptafluoro-2-iodopropane, 6-bromo-1-hexene, 2-bromo-2-nitropropane, 2-bromo-5-nitrothiophene, 2-bromopropene, 3-chloro-5,5-dimethyl-2-cyclohe-xane, 2-chloro-2-methylpropane, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)-acetophenone, 1,1,2,2,3,3,4,4-octafluorobutane, 1,1,1,3,3-pentafluorobutane, perfluoro-2-methyl-2-pentene, perfluorobutylethyl ether, bis(perfluoroisopropyl) ether and bis(perfluoropropyl) ether.

11. The method of claim 10, wherein the fluorinated gas that has been converted to a gas from a gaseous precursor is selected from the group consisting of bromoperfluoropropane, perfluorobutyl methyl ether, perfluoromethyl n-butyl ether, perfluoromethyl isopropyl ether, perfluoromethyl t-butyl ether, perfluorotetrahydropyran, and perfluoromethyltetrahydrofuran.

12. The method of claim 1, wherein the stabilizing material is in a vesicular form.

13. The method of claim 1, wherein the stabilizing material is non-vesicular.

14. The method of claim 1, wherein the stabilizing material comprises a lipid, a protein or a polymer.

15. The method of claim 14, wherein the stabilizing material comprises a lipid.

16. The method of claim 15, wherein the lipid is a phospholipid or a fluorinated lipid.

17. The method of claim 1, wherein the stabilizing material comprises a surfactant.

18. The method of claim 17, wherein the surfactant is a fluorinated surfactant.

19. The method of claim 1, wherein the composition further comprises a fluorinated liquid compound.

20. The method of claim 19, wherein the fluorinated liquid compound is selected from the group consisting of perfluorohexane, perfluoroheptane, perfluorooctane, perfluorononane, perfluorodecane, perfluorododecane, perfluorodecalin, perfluorooctyliodide, perfluorooctylbromide, perfluorotributylamine, perfluorotripropylamine, perfluorobutyl ethyl ether, bis(perfluoroisopropyl) ether and bis (perfluoropropyl) ether.

21. An oxygen delivery agent comprising a composition which comprises a fluorinated gas, oxygen, and a stabilizing material, wherein:

(a) the fluorinated gas is selected from the group consisting of bromotrifluoroethane, chlorotrifluoromethane, dichlorodifluoromethane, dibromofluoromethane, chloropentafluoroethane, bromochlorodifluoromethane, dichloro-1,1,2,2-tetrafluoroethane, hexafluoroethane, perfluoromethane, perfluoroethane, perfluoropropylene, perfluoro-2-butyne, perfluoro-2-butene, perfluorobuta-1,3-diene, perfluoro n-propyl ethyl ether, perflouro diethyl ether, perfluoro methyl ethyl ether, perfluoro dimethyl ether, sulfur hexafluoride, selenium hexafluoride and perfluoropropionyl chloride; and (b) the fluorinated gas in the composition is present in an amount of about 15% to about 85% of the total amount of gas in the composition and the oxygen is present in an amount of about 85% to about 15% of the total amount of gas in the composition.

22. The oxygen delivery agent of claim 21, further comprising an aqueous carrier.

23. The oxygen delivery agent of claim 21, wherein the oxygen is $O_2$.

24. The oxygen delivery agent of claim 21, wherein the fluorinated gas is present in an amount of about 20% to about 80% of the total amount of gas in the composition and the oxygen is present in an amount of about 80% to about 20% of the total amount of gas in the composition.

25. The oxygen delivery agent of claim 21, wherein the fluorinated gas is selected from the group consisting of perfluoromethane, perfluoroethane, perfluoro n-propyl ethyl ether, perflouro diethyl ether, perfluoro methyl ethyl ether, perfluoro dimethyl ether and sulfur hexafluoride.

26. The oxygen delivery agent of claim 25, wherein the fluorinated gas is selected from the group consisting of perfluoromethane, and perfluoroethane.

27. The oxygen delivery agent of claim 21, wherein the fluorinated gas has been converted to a gas from a gaseous precursor.

28. The oxygen delivery agent of claim 27, wherein the fluorinated gas that has been converted to a gas from a gaseous precursor is selected from the group consisting of 1-bromo-1,1,2,3,3,3-hexafluoropropane, bromoperfluoropropane, 2-chloro-1,1,1,4,4,4-hexafluoro-2-butene, 2-chloropentafluoro-1,3-butadiene, iodotrifluoroethylene, 1,1,2-trifluoro-2-chloroethane, 1,2-difluorochloroethane, 1,1-difluoro-2-chloroethane, 1,1-dichlorofluoroethane, 1-bromoethane, 1-fluorobutane, perfluorotetrahydropyran, perfluoromethyltetrahydrofuran, perfluoro t-butyl methyl ether, perfluoro n-butyl methyl ether, perfluoro isopropyl methyl ether, 1-bromo-nonafluorobutane, 1-chloro-1-fluoro-1-bromomethane, 1,1,1-trichloro-2,2,2-trifluoroethane, 1,2-dichloro-2,2-difluoroethane, 1,1-dichloro-1,2-difluoroethane, 1,2-dichloro-1,1,3-trifluoropropane, 1-bromoperfluorobutane, 1-bromo-2,4-difluorobenzene, 2-iodo-1,1,1-trifluoroethane, 5-bromovaleryl chloride, 1,3-dichlorotetrafluoroacetone, bromine pentafluoride, heptafluoro-2-iodopropane, 6-bromo-1-hexene, 2-bromo-2-nitropropane, 2-bromo-5-nitrothiophene, 2-bromopropene, 3-chloro-5,5-dimethyl-2-cyclohe-xane, 2-chloro-2-methylpropane, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)-acetophenone, 1,1,2,2,3,3,4,4-octafluorobutane, 1,1,1,3,3-pentafluorobutane, perfluoro-2-methyl-2-pentene, perfluorobutylethyl ether, bis(perfluoroisopropyl) ether and bis(perfluoropropyl) ether.

29. The oxygen delivery agent of claim 28 wherein the fluorinated gas that has been converted to a gas from a gaseous precursor is selected from the group consisting of bromoperfluoropropane, perfluorobutyl methyl ether, perfluoromethyl n-butyl ether, perfluoromethyl isopropyl ether, perfluoromethyl t-butyl ether, perfluorotetrahydropyran, and perfluoromethyltetrahydrofuran.

30. The oxygen delivery agent of claim 21, wherein the stabilizing material is in a vesicular form.

31. The oxygen delivery agent of claim 21, wherein the stabilizing material is non-vesicular.

32. The oxygen delivery agent of claim 21, wherein the stabilizing material comprises a lipid, a protein or a polymer.

33. The oxygen delivery agent of claim 32, wherein the stabilizing material comprises a lipid.

34. The oxygen delivery agent of claim 33, wherein the lipid is a phospholipid or a fluorinated lipid.

35. The oxygen delivery agent of claim 21, wherein the stabilizing material comprises a surfactant.

36. The oxygen delivery agent of claim 35, wherein the surfactant is a fluorinated surfactant.

37. The oxygen delivery agent of claim 21, wherein the composition further comprises a fluorinated liquid compound.

38. The oxygen delivery agent of claim 37, wherein the fluorinated liquid compound is selected from the group consisting of perfluorohexane, perfluoroheptane, perfluorooctane, perfluorononane, perfluorodecane, perfluorododecane, perfluorodecalin, perfluorooctyliodide, perfluorooctylbromide, perfluorotributylamine, perfluorotripropylamine, perfluorobutyl ethyl ether, bis(perfluoroisopropyl) ether and bis(perfluoropropyl) ether.

* * * * *